United States Patent
Swart

(10) Patent No.: US 9,724,355 B2
(45) Date of Patent: Aug. 8, 2017

(54) FULVESTRANT COMPOSITIONS AND METHODS OF USE

(75) Inventor: Henk Swart, Plettenberg Bay (ZA)

(73) Assignee: SHIMODA BIOTECH (PTY) LTD, Plettenberg Bay (ZA)

( * ) Notice: Subject to any disclaimer, the term of this patent is extended or adjusted under 35 U.S.C. 154(b) by 275 days.

(21) Appl. No.: 13/823,078

(22) PCT Filed: Sep. 16, 2011

(86) PCT No.: PCT/IB2011/054058
§ 371 (c)(1),
(2), (4) Date: Jun. 7, 2013

(87) PCT Pub. No.: WO2012/035516
PCT Pub. Date: Mar. 22, 2012

(65) Prior Publication Data
US 2013/0274236 A1    Oct. 17, 2013

Related U.S. Application Data

(60) Provisional application No. 61/383,660, filed on Sep. 16, 2010.

(51) Int. Cl.
| | | |
|---|---|---|
| A61K 31/565 | (2006.01) | |
| A61K 9/20 | (2006.01) | |
| A61K 31/566 | (2006.01) | |
| A61K 47/48 | (2006.01) | |
| A61K 47/40 | (2006.01) | |
| B82Y 5/00 | (2011.01) | |
| C08B 37/16 | (2006.01) | |
| A61K 9/00 | (2006.01) | |

(52) U.S. Cl.
CPC .......... *A61K 31/565* (2013.01); *A61K 9/0065* (2013.01); *A61K 9/0095* (2013.01); *A61K 9/2018* (2013.01); *A61K 9/2054* (2013.01); *A61K 31/566* (2013.01); *A61K 47/40* (2013.01); *A61K 47/48969* (2013.01); *B82Y 5/00* (2013.01); *C08B 37/0015* (2013.01); *A61K 9/0043* (2013.01)

(58) Field of Classification Search
CPC ........................ A61K 31/565; A61K 31/566
See application file for complete search history.

(56) References Cited

U.S. PATENT DOCUMENTS

| | | | |
|---|---|---|---|
| 4,383,992 A * | 5/1983 | Lipari | 514/174 |
| 4,596,795 A | 6/1986 | Pitha | |
| 5,571,534 A | 11/1996 | Jalonen et al. | |
| 5,798,338 A * | 8/1998 | Backensfeld et al. | 514/26 |
| 6,413,533 B1 | 7/2002 | Steiner et al. | |
| 6,632,447 B1 | 10/2003 | Steiner et al. | |
| 2004/0024044 A1 | 2/2004 | Di Salle et al. | |
| 2005/0043285 A1 | 2/2005 | Evans et al. | |
| 2006/0030552 A1 * | 2/2006 | MacDonald et al. | 514/182 |
| 2006/0122274 A1 | 6/2006 | Hansen et al. | |
| 2006/0270641 A1 | 11/2006 | Steiner et al. | |
| 2007/0044662 A1 | 3/2007 | Song et al. | |
| 2007/0144968 A1 * | 6/2007 | Fazioni et al. | 210/635 |
| 2009/0099265 A1 | 4/2009 | Van As | |

FOREIGN PATENT DOCUMENTS

| | | |
|---|---|---|
| EP | 1568381 A1 | 8/2005 |
| WO | 9602277 A1 | 2/1996 |
| WO | WO-2005/123130 A2 | 12/2005 |
| WO | WO-2005/123130 A3 | 12/2005 |

OTHER PUBLICATIONS

International Search Report mailed on Dec. 22, 2011, for PCT Patent Application No. PCT/IB2011/054058, filed on Sep. 16, 2011, six pages.
Stirone, C. et al. (2005). "Estrogen Receptor Activation of Phosphoinositide-3 Kinase Akt, and Nitric Oxide Signaling in Cerebral Blood Vessels: Rapid and Long-Term Effects," *Molecular Pharmacology* 67(1):105-113.
Written Opinion of the International Searching Authority mailed on Dec. 22, 2011, for PCT Patent Application No. PCT/IB2011/054058, filed on Sep. 16, 2011, five pages.
Thompson, Mark J., et al.; "Sugar conjugates of fulvestrant (ICI 182,780): efficient general procedures for glycosylation of the fulvestrant core," Tetrahedron Letters, 2004, pp. 1207-1210, vol. 45.
Loftsson, Thorsteinn, et al.; "Evaluation of cyclodextrin solubilization of drugs," International Journal of Pharmaceutics, 2005, pp. 18-28, vol. 302.
Robertson, John F.; "Fulvestrant (Faslodex®)—How to Make a Good Drug Better," The Oncologist, 2007, pp. 774-784, vol. 12.
Journé, Fabrice, et al.; "Hormone therapy for breast cancer, with an emphasis on the pure antiestrogen fulvestrant: mode of action, antitumor efficacy and effects on bone health," Expert Opinion on Drug Safety, 2008, pp. 241-258, vol. 7.
Kabos, Peter, et al.; "Fulvestrant: a unique antiendocrine agent for estrogen-sensitive breast cancer," Expert Opinion on Pharmacotherapy, 2010, pp. 807-816, vol. 11.
European Patent Office; Extended European Search Report for European Patent Application No. 11824680.0 dated Apr. 15, 2016, 11 pages.
Israeli Patent Office; Office Action for Israeli Patent Application No. 225227 dated Dec. 16, 2015, 3 Pages.
Israeli Patent Office; Office Action for Israeli Patent Application No. 225227 dated Feb. 22, 2017, 6 Pages.

* cited by examiner

Primary Examiner — Craig Ricci
Assistant Examiner — Christopher R Stone
(74) *Attorney, Agent, or Firm* — Moore & Van Allen, PLLC

(57) ABSTRACT

Provided are inclusion complexes comprising fulvestrant and a cyclodextrin. The complexes may be useful for treating various conditions, such as cancer and systemic lupus erythematosus. Also provided are methods of producing the inclusion complexes, methods of using the inclusion complexes in therapy, and kits and unit dosages comprising the complexes.

8 Claims, 17 Drawing Sheets

FULVESTRANT COMPOSITIONS AND METHODS OF USE

CROSS-REFERENCE TO RELATED APPLICATION

This patent application is a National Phase application under 35 U.S.C. §371 of International Application No. PCT/IB2011/054,058, filed Sep. 16, 2011, which claims priority from U.S. 61/383,660, filed Sep. 16, 2010, the contents of which are incorporated herein by reference.

FIELD OF THE INVENTION

The present invention relates to inclusion complexes between fulvestrant and a cyclodextrin, and formulations thereof. Methods of preparing fulvestrant inclusion complexes are also provided. Moreover, the present invention relates to the use of inclusion complexes of, and pharmaceutical formulations comprising, fulvestrant and a cyclodextrin in the treatment of a disease or condition that is or is believed to be responsive to anti-estrogen therapy and/or ER-downregulation, such as cancer.

BACKGROUND OF THE INVENTION

Fulvestrant (7-alpha-[9-(4,4,5,5,5-penta fluoropentylsulphinyl)nonyl]estra-1,3,5-(10)-triene-3,17-beta-diol), has the structural formula (I):

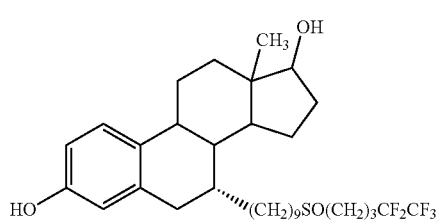

(I)

and is commercially available as an oily parenteral formulation for monthly intramuscular administration under the tradename FASLODEX® (AstraZeneca Pharmaceuticals LP). Fulvestrant contains 6 asymmetric carbon atoms and a stereogenic sulphoxide in the side chain. The active ingredient of FASLODEX® is a mixture of 2 diastereoisomers: fulvestrant sulphoxide A and B, having the same absolute configuration at each of the stereogenic centers in the steroid system but different absolute configurations at the sulphur atom. Commercially available Fulvestrant is a mixture of two diastereoisomers, Fulvestrant Sulphoxide A and Fulvestrant Sulphoxide B. Fulvestrant formulations have been described in, for example, U.S. Pat. Nos. 6,774,122 and 7,456,160.

Fulvestrant acts as an estrogen receptor antagonist without agonist properties, blocking the trophic actions of estrogens without itself having any partial agonist (estrogen-like) activity on the endometrium. Fulvestrant binds to estrogen receptors (ERs) in a competitive manner with affinity comparable with that of estradiol and downregulates the ER protein in human breast cancer cells. Data from pre-clinical studies indicated that fulvestrant is effective against human breast cancer cells and xenografts displaying acquired resistance to tamoxifen or letrozole. See, Osborne et al, *Cancer Chemother. Pharmacol.*, 134(2): 89-95 (1994); Osborne et al, *Journal of the National Cancer Institute*, 87(10) 746-750 (1995); and Long and Jelovac, *Clinical Cancer Research*, 8:2378-2388 (2002). FASLODEX® is currently indicated for use in the treatment of hormone receptor positive metastatic breast cancer in postmenopausal women with disease progression following antiestrogen therapy. Bross et al., *The Oncologist*, 7:477-480 (2002).

Fulvestrant's characteristics, such as having a very high lipophilicity, extremely low aqueous solubility and the fact that it is only ionized at very high pH, present formulation challenges and account for its administration as an oily intramuscular injection. Commercially available FASLODEX® is an intramuscular injection of 250 mg fulvestrant in a sterile oily solution in either a single 5 ml pro-filled syringe or two 2.5 ml pre-filled syringes, as long acting injection(s). The long acting FASLODEX® intramuscular depot formulation contains benzyl alcohol and castor oil as solvents and is designed to deliver the dose of 250 mg of fulvestrant over a 1 month period from a single 5 ml intramuscular injection in the buttock or two 2.5 ml intramuscular injection into the buttocks. Bross et al., *The Oncologist*, 7:477-480 (2002). While this required monthly dose of 250 mg or bi-monthly dose of 125 mg of fulvestrant is effective, it takes approximately 3-6 months to achieve steady-state plasma levels of fulvestrant. See, e.g., Chia and Gradishar, *The Breast*, 17:S16-S21 (2008); and William et al., *Clinical Breast Cancer*, 6(1):S23-S29 (2005). Decreasing the time in which steady-state plasma levels are reached following administration of fulvestrant may reduce the time taken to achieve a therapeutic response, which can be particularly beneficial for patients who would otherwise experience disease progression early during endocrine treatment. Robertson, J. F. R, *The Oncologist*, 12:744-784 (2007). In addition, increasing ER downregulation with higher doses of fulvestrant may provide a better treatment response. Id.

Alternative dosing regimens of FASLODEX® have been suggested as a way to enhance the efficacy of fulvestrant therapy. However, even if alternative dosing regimens of FASLODEX® were to provide a therapeutic benefit, administration of fulvestrant as an intramuscular injection still has various disadvantages. For example, injection-site reaction, including transient pain and inflammation, is one of the most common drug-related events reported for FASLODEX®. Bross, *The Oncologist*, 7:477-480 (2002). Other disadvantages associated with intramuscular administration include nerve/bone damage during needle insertion, pain and tissue damage, accidental injection of air into artery or vein, extreme pain and/or tissue damage. Such events would only increase if new dosing regimens require more frequent injections. Intramuscular injections may also be inconvenient to the patient and be a source of anxiety, which can adversely impact patient compliance. In one study of patient preference for administration of endocrine therapy by injection or oral tablets, the majority of respondants generally preferred administration via daily tablets. L. Fallowfield, et ah, *Annals of Oncology*, 17: 205-210 (2006). Given the importance of patient compliance to therapeutic outcome, patient preference is an important consideration. In addition, intramuscular injections are not suitable for all patients. For example, patients with certain blood disorders {e.g., bleeding diatheses, thrombocytopenia) or receiving anticoagulants may not be suitable candidates for administration of fulvestrant by intramuscular injection.

Delivery of fulvestrant via non-invasive formulations, such as oral delivery, have been explored, but adequate bioavailability, aqueous solubility, and target formulation concentration could not be achieved, presumably due to the high lipophilicity and low aqueous solubility of fiulvestrant. See, e.g., Harrison M., et al., (2003) *Proc. ASCO*, 22: 45, abstract 311.

There therefore remains a need for additional fulvestrant formulations, such as formulations that render fulvestrant suitable for oral, intranasal and/or sublingual administration.

BRIEF SUMMARY OF THE INVENTION

The present invention provides inclusion complexes, kits, formulations, and unit dosages comprising fulvestrant and a cyclodextrin. Also provided are methods of producing fulvestrant inclusion complexes and methods of treating a disease or indication that is responsive to fulvestrant therapy comprising administering a fulvestrant inclusion complex or formulation thereof to an individual.

In one aspect, an inclusion complex comprising a) a cyclodextrin; and b) a compound of the formula (I):

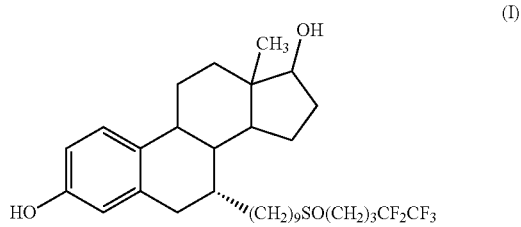

or a salt thereof or a solvate of the foregoing, is provided. The compound of formula (I) is also referred to herein as "fulvestrant". In some embodiments of any of the aspects of the invention, the compound of the formula (I) is fulvestrant sulphoxide A, fulvestrant sulphoxide B, or a mixture of fulvestrant sulphoxide A and fulvestrant sulphoxide B. It is understood that fulvestrant salts, such as pharmaceutically acceptable salts, and solvates thereof are also intended by the descriptions provided herein. Thus, all salt and non-salt forms of fulvestrant and solvates of the foregoing are embraced by the invention and descriptions of fulvestrant provided herein. In some embodiments, the cyclodextrin is hydroxypropyl beta-cyclodextrin (HPBCD) or methyl beta-cyclodextrin (MBCD).

In some embodiments of any of the aspects of the invention, the cyclodextrin for use in the inclusion complexes and formulations herein is a water soluble unsubstituted or substituted alpha-cyclodextrin (ACD), beta-cyclodextrin (BCD), or gamma-cyclodextrin (GCD). In some embodiments, the beta-cyclodextrin is selected from the group consisting of methyl beta-cyclodextrin (MBCD), hydroxypropyl beta-cyclodextrin (HPBCD), and sulfobutylether beta-cyclodextrin (SBEBCD). In some embodiments, the beta-cyclodextrin is methyl beta-cyclodextrin or hydroxypropyl beta-cyclodextrin. In some embodiments, the gamma-cyclodextrin is hydroxypropyl gamma-cyclodextrin (HPGCD). In one preferred embodiment, the cyclodextrin is hydroxypropyl beta-cyclodextrin (HPBCD) or methyl beta-cyclodextrin (MBCD).

In one aspect, provided are methods for improving the solubility of a compound of the formula (I) in water comprising combining the compound of the formula (I) with a cyclodextrin. In another aspect, a method of increasing the water solubility of a compound of formula (I) is provided, wherein the method comprises forming an inclusion complex of a cyclodextrin and a compound of the formula (I). In some embodiments, the solubility of the compound of the formula (I), when present as an inclusion complex with a cyclodextrin in deionized water at 20° C., is increased by at least about or about 1.5-fold or 2-fold, when compared to the solubility of the compound of formula (I) in uncomplexed form under the same conditions. In other embodiments, the solubility, such as the aqueous solubility, of fulvestrant in an inclusion complex may be increased by at least about or about any of 3, 4, 5, 10, 15, 20, 30, 40, 50, 60, 70, 80, 90, 100, 200, 300, 400, 500, 1,000, 2,000-fold or more over uncomplexed fulvestrant. Solubility comparisons may be assessed by methods known to the skilled artisan, such as any of the specific methods and conditions detailed herein. In one preferred embodiment, the cyclodextrin is hydroxypropyl beta-cyclodextrin (HPBCD) or methyl beta-cyclodextrin (MBCD).

A method of increasing the oral bioavailability of a compound of formula (I) is provided, wherein the method comprises forming an inclusion complex of a cyclodextrin and a compound of the formula (I). In some embodiments, the oral bioavailability of the compound of the formula (I), when present as an inclusion complex with a cyclodextrin, is at least about 50% greater than the oral bioavailability of the compound of the formula (I) in uncomplexed form. Oral bioavailability, and comparisons thereof; may be assessed by methods known in the art, including any of the specific methods described herein. In one preferred embodiment, the cyclodextrin is hydroxypropyl beta-cyclodextrin (HPBCD) or methyl beta-cyclodextrin (MBCD).

In some embodiments, an inclusion complex of a compound of formula (I) and a cyclodextrin are provided, wherein the inclusion complex is capable of inducing a greater maximum concentration ($C_{max}$) of the compound systemically than what is achievable when the compound is administered alone in the same amount and under the same conditions. In one aspect, an inclusion complex of the compound of formula (I) is capable of inducing at least about or about 1.5 or 2 or more times greater $C_{max}$ for the compound systemically than what is achievable when the compound is administered alone in the same amount and under the same conditions. In some embodiments, the $C_{max}$ of fulvestrant, when administered to an individual as an inclusion complex with a cyclodextrin, is at least about 2 times greater than the $C_{max}$ of fulvestrant administered alone under the same conditions. In one preferred embodiment, the cyclodextrin is hydroxypropyl beta-cyclodextrin (HPBCD) or methyl beta-cyclodextrin (MBCD).

In some embodiments, an inclusion complex of a compound of formula (I) and a cyclodextrin is provided, wherein the inclusion complex is capable of inducing a greater area under the plasma concentration vs. time curve (AUC) of the compound than what is achievable when the compound is administered alone (in the absence of a cyclodextrin) in the same amount and under the same conditions. In one aspect, an inclusion complex of the compound of formula (I) is capable of inducing at least about or about 1 or 2 or more times greater AUC of compound than what is achievable when the compound is administered alone in the same amount and under the same conditions. In some embodiments, the AUC of fulvestrant, when administered to an individual as an inclusion complex with a cyclodextrin, is at least about 2 times greater than the AUC of fulvestrant administered alone in the same amount and under the same conditions. In one preferred embodiment, the cyclodextrin is hydroxypropyl beta-cyclodextrin (HPBCD) or methyl beta-cyclodextrin (MBCD).

In some embodiments, an inclusion complex of a compound of formula (I) and a cyclodextrin is provided, wherein the inclusion complex is capable of inducing a change in the time to reach the maximum plasma level ($T_{max}$) of the compound than what is achievable when the compound is administered alone (in the absence of a cyclodextrin) in the same amount and under the same conditions. In one aspect, $T_{max}$ is shorter with a fulvestrant inclusion complex. In one aspect, an inclusion complex of the compound of formula (I) is capable of reducing $T_{max}$ by about 0.5 or 1 or 2 fold over what is achievable when the compound is administered alone in the same amount and under the same conditions. In some embodiments, the $T_{max}$ of fulvestrant, when administered to an individual as an inclusion complex with a cyclodextrin, is at least about 2 times lower than the $T_{max}$ of fulvestrant administered alone in the same amount and under the same conditions. In one aspect, a fulvestrant inclusion complex reduces $T_{max}$ by at least about or about any of 1, 2, 3, 5, 10 and 12 hours or more. In one preferred embodiment, the cyclodextrin is hydroxypropyl beta-cyclodextrin (HPBCD) or methyl beta-cyclodextrin (MBCD).

In some embodiments, an orally, intranasally, sublingually, rectally, or vaginally administered inclusion complex of a compound of formula (I) and a cyclodextrin is provided, wherein the inclusion complex may be administered together with a long acting intramuscular fulvestrant formulation (e.g., FASLODEX®), compensating for the time required for the long acting intramuscular fulvestrant formulation alone to reach steady state fulvestrant plasma concentrations. In one preferred embodiment, the cyclodextrin is hydroxypropyl beta-cyclodextrin (HPBCD) or methyl beta-cyclodextrin (MBCD).

In some embodiments, a composition comprising a cyclodextrin and a compound of the formula (I) are provided, wherein the molar ratio of the compound of formula (I) to the cyclodextrin is from about 1:1 to about 1:300. In one aspect, the composition comprises an inclusion complex of a cyclodextrin and a compound of the formula (I). In another aspect, the composition comprises a physical mixture of a cyclodextrin and a compound of the formula (I), wherein the physical mixture does not comprise or is substantially free of an inclusion complex of a cyclodextrin and a compound of the formula (I). In one preferred embodiment, the cyclodextrin is hydroxypropyl beta-cyclodextrin (HPBCD) or methyl beta-cyclodextrin (MBCD).

In another aspect, a formulation comprising a) a cyclodextrin; b) a compound of the formula (I), or a salt thereof or solvate of the foregoing; and c) a carrier, are provided. In one aspect, the formulation comprises an inclusion complex of the compound and a cyclodextrin. In one variation, the carrier is a pharmaceutically acceptable carrier. The carrier may be in liquid, solid or semi-solid form. When the carrier is a liquid, it may be aqueous or an organic solvent, or a combination thereof in any amount. In one aspect, the carrier is selected from the group consisting of a solvent, a complexing agent, a filler, a diluent, a granulating agent, a disintegrant, a lubricant, a glidant, a pH-modifier, a tonicity modifier, an adjuvant, a dye, a polymer-based film coating, and a binder. In some embodiments, the carrier is one or more of water for injection, microcrystalline cellulose, glucose, sodium lauryl sulphate, crosscarmellose sodium, colloidal silica, talc, magnesium stearate, sodium benzoate, aluminum magnesium silicate, lactose, methanol, ethanol, propanol, and acetone. More than one carrier may be employed and combinations of carriers provided herein are intended. In one preferred embodiment, the cyclodextrin is hydroxypropyl beta-cyclodextrin (HPBCD) or methyl beta-cyclodextrin (MBCD).

Formulations comprising a cyclodextrin and fulvestrant may further comprise additional formulation components, also referred to herein as additional agents. In some embodiments of the formulations described herein, the formulation further comprises an antioxidant. In one aspect, the antioxidant is a water-soluble antioxidant. In another aspect, the antioxidant is fully or partially water-insoluble. When a water-insoluble antioxidant is employed, care may be taken to reduce or avoid displacement of fulvestrant in the inclusion complex by the antioxidant. For example, formulations comprising a fulvestrant inclusion complex and a water-insoluble antioxidant may contain a relatively small amount of the antioxidant or take other precautions to reduce or avoid adverse consequences of the antioxidant on an inclusion complex of fulvestrant and a cyclodextrin. In some embodiments, the formulation may include combinations of two or more of the antioxidants as described herein. In some embodiments, the antioxidant is selected from the group consisting of ascorbyl palmitate, butylated hydroxyanisole, butylated hydroxytoluene, malic acid, propyl gallate, sodium bisulfite, sodium sulfite, sodium metabisulfite, potassium metabisulfite, potassium bisulfite, sodium thiosulfate, sodium formaldehyde sulfoxylate, L-ascorbic acid, D-ascorbic acid, acetylcysteine, cysteine, thioglycerol, thioglycolic acid, thiolactic acid, thiourea, dithiothreitol, dithioerythreitol, glutathione, nordihydroguaiaretic acid, tocopherol, sodium ascorbate, hypophosphorous acid, and fumaric acid. In some embodiments, the antioxidant is selected from the group consisting of butylated hydroxyanisole, malic acid, sodium bisulfite, sodium sulfite, sodium metabisulfite, potassium metabisulfite, potassium bisulfite, sodium thiosulfate, sodium formaldehyde sulfoxylate, L-ascorbic acid, D-ascorbic acid, cysteine, thiolactic acid, glutathione, nordihydroguaiaretic acid, sodium ascorbate, hypophosphorous acid and fumaric acid. In some embodiments, the antioxidant is a dietary antioxidant, including, but not limited to, vitamin E, vitamin C, beta-carotene, and selenium. Other additional agents may be employed in the formulations. In one preferred embodiment, the cyclodextrin is hydroxypropyl beta-cyclodextrin (HPBCD) or methyl beta-cyclodextrin (MBCD).

In some embodiments, a formulation comprising (a) a cyclodextrin; (b) a compound of the formula (I), or a salt thereof, or solvate of the foregoing; and (c) a carrier, is a solid formulation. In some embodiments, the formulation is a semi-solid. In some embodiments, the formulation is a liquid. In one preferred embodiment, the cyclodextrin is hydroxypropyl beta-cyclodextrin (HPBCD) or methyl beta-cyclodextrin (MBCD).

Unit dosage forms of fulvestrant inclusion complexes and formulations comprising fulvestrant and a cyclodextrin are also provided. In some embodiments, the compound of the formula (I) is present in an amount of between about 0.1 mg and about 500 mg per unit solid or semi-solid dosage form or between about 0.1 mg/mL and about 50 mg/mL in a liquid dosage form. In some embodiments, the compound of the formula (I) is present in an amount of about 250 mg per unit solid or semi-solid dosage form or about 25 mg/mL in a liquid dosage form. In one preferred embodiment, the cyclodextrin is hydroxypropyl beta-cyclodextrin (HPBCD) or methyl beta-cyclodextrin (MBCD).

In another aspect, an inclusion complex described herein is in a substantially pure form.

Methods of administering fulvestrant inclusion complexes and formulations to an individual are also provided, as are methods of using such complexes and formulations in therapy. For example, methods of treating a disease or condition that is or is believed to be responsive to anti-estrogen therapy and/or ER-downregulation are provided, wherein the methods comprise administering to an individual in need thereof a fulvestrant inclusion complex or formulation comprising fulvestrant and a cyclodextrin, wherein fulvestrant is not complexed with the cyclodextrin. In one aspect, the disease or condition is cancer. The cancer may be early stage cancer, non-metastatic cancer, primary cancer, advanced cancer, locally advanced cancer, metastatic cancer, cancer in remission, recurrent cancer, cancer in an adjuvant setting, cancer in a neoadjuvant setting, or cancer substantially refractory to hormone therapy. In some embodiments, the cancer is selected from the group consisting of breast cancer, endometrial cancer, prostate cancer, and lung cancer. In one variation, the cancer is breast cancer, such as hormone receptor positive metastatic breast cancer. In another aspect, the disease or condition is systemic lupus erythematosus. In one preferred embodiment, the cyclodextrin is hydroxypropyl beta-cyclodextrin (HPBCD) or methyl beta-cyclodextrin (MBCD).

In a particular aspect, a method of treating a cancer in an individual in need thereof is provided, wherein the method comprises administering to the individual an effective amount of an inclusion complex of a) a cyclodextrin; and b) a compound of the formula (I), or a salt thereof, or solvate of the foregoing. The method may also employ a fulvestrant formulation described herein, such as a formulation comprising a) a cyclodextrin; b) a compound of the formula (I), or a salt thereof, or solvate of the foregoing; and c) a carrier (e.g., a pharmaceutically acceptable carrier). In one preferred embodiment, the cyclodextrin is hydroxypropyl beta-cyclodextrin (HPBCD) or methyl beta-cyclodextrin (MBCD).

In some embodiments, the individual of the methods provided herein is a human, and may be male or female. In some embodiments the human has or is suspected of having a disease or condition that is or is believed to be responsive to anti-estrogen therapy and/or ER-downregulation, such as cancer. In some embodiments, the individual is a post-menopausal woman who has or is suspected of having hormone receptor positive metastatic breast cancer. In some embodiments, the individual is a post-menopausal woman who has or is suspected of having hormone receptor positive metastatic breast cancer with disease progression following hormone (e.g., anti-estrogen) therapy. In some embodiments the human has or is suspected of having systemic lupus erythematosus.

In one aspect of the methods, the fulvestrant inclusion complex, or a fulvestrant formulation provided herein, is intranasally, orally, sublingually, rectally, and/or vaginally administered to the individual in need thereof. In some embodiments, the dosage of fulvestrant in the administered dose is between about 0.1 mg and about 500 mg per unit solid or semi-solid dosage form or between about 0.1 mg/mL and about 50 mg/mL in a liquid dosage form.

In another aspect of the therapeutic methods, such as a method of treating a cancer in an individual in need thereof, the individual is administered a combination of an effective amount of a fulvestrant inclusion complex or formulation and one other pharmaceutical agent. In some embodiments, the other pharmaceutical agent is an anti-cancer agent. In some embodiments, the other pharmaceutical agent is selected from the group consisting of anastrozole (e.g., ARIMIDEX®), letrozole (e.g., FEMARA®), exemestane (e.g., AROMASIN®), aminoglutethimide (e.g., Cytadren®), vorozole (e.g., RIVIZOR®), formestane (e.g., LENTARON®), fadrozole (e.g., AFEMA®), testolactone (e.g., TESLAC®), gefitinib (e.g., IRESSA®), trastuzumab (e.g., HERCEPTIN®), erlotinib (e.g., TARCEVA®), tipifanib (e.g., ZARNESTRA®), uncomplexed fulvestrant (e.g., FASLODEX® (AstraZeneca Pharmaceuticals LP)), and an antioxidant. It is understood that in some variations of the methods provided herein, two or more other pharmaceutical agents are intended for use in the methods, such as two or more of the anti-cancer agents provided herein. In some embodiments, the inclusion complex and the other pharmaceutical agent are administered simultaneously or sequentially. In some embodiments, the inclusion complex and the other pharmaceutical agent are administered concurrently. The inclusion complex and the other pharmaceutical agent may be administered, whether simultaneously, sequentially or otherwise, via the same or different routes.

In one variation, the methods comprise administering a) a composition comprising and/or an inclusion complex of a cyclodextrin and a compound of the formula (I), or a salt thereof, or solvate of the foregoing, and b) a compound of the formula (I) in uncomplexed form. In a particular variation, a composition comprising and/or an inclusion complex of a cyclodextrin and a compound of the formula (I), or a salt thereof, or solvate of the foregoing, is administered orally, intranasally, sublingually, rectally, and/or vaginally and a compound of the formula (I) is administered intramuscularly. In one preferred embodiment, the cyclodextrin is hydroxypropyl beta-cyclodextrin (HPBCD) or methyl beta-cyclodextrin (MBCD).

In another aspect, provided is the use of an inclusion complex of a) a cyclodextrin; and b) a compound of the formula (I), or a salt thereof, or solvate of the foregoing, for the manufacture of a medicament for use in a method provided herein, such as a method of treating a cancer, such as breast cancer, in an individual. In one preferred embodiment, the cyclodextrin is hydroxypropyl beta-cyclodextrin (HPBCD) or methyl beta-cyclodextrin (MBCD).

In another aspect, provided is a kit comprising an inclusion complex of a) a cyclodextrin; and b) a compound of the formula (I), or a salt thereof or solvate of the foregoing, or a formulation thereof. The kit may further comprise instructions for use, such as for use in the treatment of a disease or condition that is or is believed to be responsive to anti-estrogen therapy and/or ER-downregulation. In a particular variation, a kit comprises instructions for use in the treatment of cancer or systemic lupus erythematosus. The kit may also comprise another pharmaceutical agent. In one such aspect, a kit is provided comprising a) a cyclodextrin; b) a compound of the formula (I), or a salt thereof, or solvate of the foregoing, or a formulation thereof, and c) an additional pharmaceutical agent selected from anastrozole (e.g., ARIMIDEX®), letrozole (e.g., FEMARA®), exemestane (e.g., AROMASIN®), aminoglutethimide (e.g., Cytadren®), vorozole (e.g., RIVIZOR®), formestane (e.g., LENTARON®), fadrozole (e.g., AFEMA®), testolactone (e.g., TESLAC®), gefitinib (e.g., IRESSA®), trastuzumab (e.g., HERCEPTIN®), erlotinib (e.g., TARCEVA®), tipifarnib (e.g., ZARNESTRA®), uncomplexed fulvestrant (e.g., FASLODEX® (AstraZeneca Pharmaceuticals LP)), and an antioxidant. When uncomplexed fulvestrant is employed, in one aspect it is formulated in an oil-based carrier (e.g., arachis oil, sesame oil, castor oil, or neutral oil (e.g., MIGLYOL® 810 or MIGLYOL® 812)), or in a non-aqueous ester solvent (e.g., benzyl benzoate, ethyl oleate, isopropyl myristate, isopropyl palmitate, or a mixture or combination of any thereof) and an alcohol (e.g., ethanol, benzyl alcohol, or a mixture or combination of any thereof). In one preferred embodiment, the cyclodextrin is hydroxypropyl beta-cyclodextrin (HPBCD) or methyl beta-cyclodextrin (MBCD).

In another aspect, provided are methods of producing an inclusion complex of a compound of the formula (I) and a cyclodextrin, comprising admixing a compound of the formula (I), or salt thereof, or solvate of the foregoing, with a cyclodextrin. In some embodiments, the method further comprises adding a solvent, mixed solvent, or buffer to the compound of the formula (I), the cyclodextrin, and/or a mixture thereof. If a solvent, mixed solvent or buffer is employed to form an inclusion complex, in one aspect the solvent, mixed solvent or buffer is removed after formulation of the inclusion complex to provide an inclusion complex free of or substantially free of solvent, mixed solvent or buffer. In one preferred embodiment, the cyclodextrin is hydroxypropyl beta-cyclodextrin (HPBCD) or methyl beta-cyclodextrin (MBCD).

In another aspect, provided are methods of producing an inclusion complex of a cyclodextrin and a compound of the formula (I), or a salt thereof, or solvate of the foregoing, comprising the steps of: a) admixing the compound of the formula (I) and the cyclodextrin; and b) adding a suitable amount of solvent, mixed solvent, or buffer to the mixture of step (a) and mixing until a suspension or solution is formed. In some embodiments, the step (a) further comprises admixing a suitable polymer. In some embodiments, the method utilizes a suitable amount of solvent, such as water for injection (WFI). In some embodiments, the method utilizes a suitable amount of a buffer, which in one aspect is a phosphate-citrate buffer. In some embodiments, the method utilizes a suitable polymer, which in one aspect is selected from polyvinylpyrrolidone, hydroxypropyl methylcellulose, carboxymethylcellulose, and PLASDONE® Povidone. In one preferred embodiment, the cyclodextrin is hydroxypropyl beta-cyclodextrin (HPBCD) or methyl beta-cyclodextrin (MBCD).

DETAILED DESCRIPTION OF THE INVENTION

Figure 1:
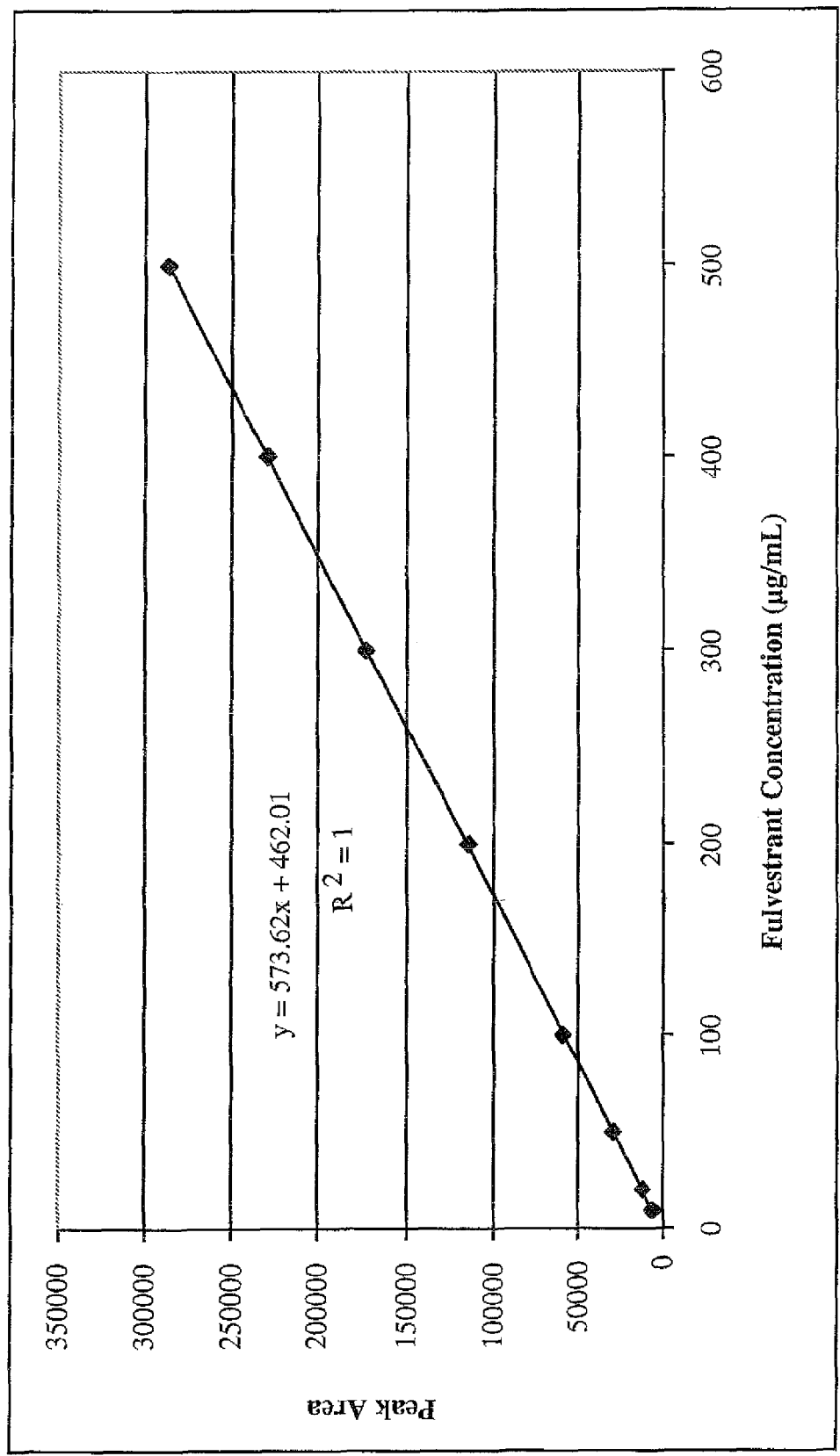
FIG. 1 shows a fulvestrant HPLC calibration data plot.

The present invention provides inclusion complexes, kits, formulations, and unit dosages comprising fulvestrant and a cyclodextrin. Also provided are methods of producing the inclusion complexes as well as methods of treatment.

The inventors have discovered that inclusion complexes comprising fulvestrant and a cyclodextrin strikingly enhance the aqueous solubility of fulvestrant as compared to fulvestrant in an uncomplexed form, suggesting that such inclusion complexes enhance the oral, intranasal and/or sublingual bioavailability of fulvestrant and may find particular use in administration of fulvestrant via these dosage routes. Fulvestrant inclusion complexes may also provide superior or complimentary pharmacokinetics as compared to uncomplexed fulvestrant delivered in the same amount and under the same conditions, including greater $C_{max}$ and AUC values and a reduction in $T_{max}$. In addition, therapeutic plasma levels of fulvestrant may be achieved sooner with a fulvestrant inclusion complex as compared to long acting intramuscular injectable formulations of uncomplexed fulvestrant, which can have a particular benefit to patients.

Abbreviations and Definitions

Unless defined otherwise or clearly indicated by context, all technical and scientific terms and abbreviations used herein have the same meaning as commonly understood by one of ordinary skill in the art to which this invention belongs.

As used herein, the term "inclusion complex" or "IC" is intended a complex wherein a moiety of a compound (e.g., a moiety of fulvestrant) is inserted, at least partially, into the cavity of a cyclodextrin (e.g., methyl beta-cyclodextrin (MBCD) or hydroxypropyl beta-cyclodextrin (HPBCD)). The inserted compound of the inclusion complex is considered "complexed" with the cyclodextrin. A compound that is not part of an inclusion complex is considered "alone" or "uncomplexed."

As used herein, the term "solubility" intends the solubility with reference to the total amount of compound (e.g., including the amount of compound in both complexed and uncomplexed form).

As used herein, "treatment", "treating", or "treat" is an approach for obtaining beneficial or desired results, including clinical results.

With respect to a disease or condition, "delaying" means to defer, hinder, slow, retard, stabilize, and/or postpone development of one or more symptoms of the disease or condition (e.g., cancer or systemic lupus erythematosus). This delay can be of varying lengths of time, depending on the history of the disease and/or individual being treated. As is evident to one skilled in the art, a sufficient or significant delay can, in effect, encompass prevention, in that the individual does not develop the condition (e.g., cancer or systemic lupus erythematosus).

As used herein, "pharmaceutically acceptable" with respect to a material, refers to a material that is not biologically or otherwise unsuitable, e.g., the material may be incorporated (e.g., at the time of manufacturing or administration) into a pharmaceutical composition administered to an individual without causing significant undesirable biological effects. Pharmaceutically acceptable carriers or excipients have preferably met the required standards of toxicological and manufacturing testing and/or are included on the Inactive Ingredient Guide prepared by the U.S. Food and Drug administration.

The term "effective amount" intends such amount of a compound (e.g., fulvestrant) or an inclusion complex (e.g., an inclusion complex comprising fulvestrant and a cyclodextrin), or a combination therapy comprising at least one of the foregoing, which should be effective in a given therapeutic form. As is understood in the art, an effective amount may be in one or more doses, i.e., a single dose or multiple doses may be required to achieve the desired treatment endpoint. An effective amount may be considered in the context of administering one or more additional pharmaceutical agents in a combination therapy, and an inclusion complex may be considered to be given in an effective amount if, when administered sequentially, simultaneously, or continuously with one or more additional pharmaceutical agents, one or more desirable or beneficial result(s) may be or are achieved.

"Combination therapy" intends a first therapy (e.g., fulvestrant or an inclusion complex thereof) used in conjunction with a second therapy (e.g., surgery and/or an additional pharmaceutical agent) for treating, stabilizing, preventing, and/or delaying a disease or condition. Administration in "conjunction with" another compound includes administration in the same or different composition(s), either sequentially, simultaneously, or continuously, through the same or different routes within a given time period. In some embodiments, the combination therapy optionally includes one or more pharmaceutically acceptable carriers or excipients, non-pharmaceutically active compounds, and/or inert substances.

The term "simultaneous administration," as used herein, means that a first therapy and second therapy in a combination therapy are administered with a time separation of no more than about 15 minutes, such as no more than about any of 10, 5, or 1 minutes. When the first and second therapies are administered simultaneously, the first and second therapies may be contained in the same composition (e.g., a composition comprising both a first and second therapy) or in separate compositions (e.g., a first therapy in one composition and a second therapy is contained in another composition). When there is a time separation in the context of simultaneous administration (e.g., 5 minutes), either the first therapy or the second therapy may be administered first.

As used herein, the term "sequential administration" means that the first therapy and second therapy in a combination therapy are administered with a time separation of more than about 15 minutes, such as more than about any of 20, 30, 40, 50, 60, or more minutes. Either the first therapy or the second therapy may be administered first. The first and second therapies are contained in separate compositions, which may be contained in the same or different packages or kits.

As used herein, the term "concurrent administration" means that the administration of the first therapy and that of a second therapy in a combination therapy overlap with each other.

Unless otherwise stated, "substantially pure" in reference to an inclusion complex intends a preparation of the inclusion complex that contains about or less than about 15% impurity, wherein the impurity intends a compound other than an inclusion complex of fulvestrant and a cyclodextrin. Substantially pure preparations include preparations that contain less than about 15% impurity, such as preparations that contain less than about any one of 15%, 12%, 10%, 8%, 5%, 3%, 2%, 1% and 0.5% impurity.

Reference to "about" a value or parameter herein includes (and describes) variations that are directed to that value or parameter per se. For example, a description referring to "about X" includes the description of "X".

As used herein, the singular forms "a," "or," and "the" include plural referents unless the context clearly dictates otherwise.

It is understood that wherever embodiments are described herein with the language "comprising," otherwise analogous embodiments described in terms of "consisting of and/or" consisting essentially of are also provided.

Where aspects or embodiments of the invention are described in terms of a Markush group or other grouping of alternatives, the present invention encompasses not only the entire group listed as a whole, but each member of the group individually and all possible subgroups of the main group, such as the main group absent one or more of the group members. The present invention also envisages the explicit exclusion of one or more of any of the group members.

Inclusion Complexes

Cyclodextrins ("CDs") are cyclic oligosaccharide structures composed of various glucopyranose units, such as 6, 7 and 8 units (alpha-, beta- and gamma-cyclodextrin, respectively) bound together to form a ring. Cyclodextrins characterized by a cone-like molecular shape and comprising a relatively hydrophobic central cavity and hydrophilic outer surface. The hydrophobic nature of the central cavity, in certain cases, endows the cyclodextrin with the ability to form inclusion complexes with a hydrophobic "guest" molecule. Polar and ionic groups are generally less likely to be included within the hydrophobic cavity than less-polar and non-ionic groups. In these complexes, a guest molecule is held within the hydrophobic cavity of the cyclodextrin "host" molecule. The inclusion complex may be stabilized by a number of forces, such as van der Waals attractive forces, electrostatics and hydrogen bonding.

Although many factors affect the stability of an inclusion complex, the ability of a cyclodextrin molecule to form an inclusion complex with a guest molecule is a function of two key factors. The first is steric and depends on the relative size of the cyclodextrin to the size of the guest molecule or certain key functional groups within the guest. The second factor is the thermodynamic interactions among different components of the system, such as the cyclodextrin, the guest, and the solvent, where present.

The binding of guest molecules within host cyclodextrins is not fixed or permanent but rather is a dynamic equilibrium. See, e.g., Valle, *Process Biochemistry*, 2004, 39(9): 1033-46 and Loftsson et al., *Journal of Pharmaceutical Sciences*, 1996, 85(10): 1017-25. Inclusion of a guest molecule in a cyclodextrin host may exert a profound effect on the physicochemical properties of the guest molecule that is temporarily locked or caged within the host cavity. Inclusion complexes may give rise to beneficial properties, which are not achievable otherwise, such as: solubility enhancement of highly insoluble guests; stabilization of labile guests against the degradative effects of oxidation, visible or UV light and heat; control of volatility and sublimation; physical isolation of incompatible compounds; chromatographic separations; taste modification by masking off flavors, unpleasant odors, and controlled release of drugs. Cyclodextrin inclusion complexes, in some cases, may provide favorable flow, binding, and compaction properties to aid in drug formulation (e.g., in facilitating tablet compression).

Importantly, however, the effect of inclusion of a guest molecule in a cyclodextrin host remains unpredictable. For example, although various cyclodextrin complexes have been reported to enhance the bioavailability of small molecule drugs, cyclodextrin inclusion complexes have also been reported to have either no effect on host bioavailability or in fact decrease the bioavailability of certain guest compounds. R. Carrier, et al., *Journal of Controlled Release*, 123(2):78-99. The interaction of cyclodextrins with labile compounds can also result in several outcomes: cyclodextrins can retard degradation, can have no effect on reactivity, or can accelerate drug degradation. Loftsson et ah, supra. In addition, the unpredictability of thermodynamic quantities related to inclusion complex formation have also been reported. A. Steffen et al., *Chemistry Central Journal*, 2007, 1:29.

Inclusion complexes of fulvestrant as provided herein were discovered to notably enhance the aqueous solubility of fulvestrant as compared to fulvestrant in an uncomplexed form, suggesting that such inclusion complexes enhance the bioavailability of fulvestrant and may be used in the oral, intranasal, and/or sublingual administration of fulvestrant. Administration of fulvestrant via non-parenteral routes is significant and may offer patients more convenient, non-invasive treatment options, reducing the incidence of adverse side effects associated with parenteral fulvestrant therapy, and enhancing overall patient compliance. Non-parenteral fulvestrant formulations may also have a positive effect on overall therapeutic outcome. For example, such formulations may be used alone, or together with parenteral administration of fulvestrant, to achieve steady-state drug levels sooner than with presently available fulvestrant parenteral formulations. In addition, higher dosing levels of fulvestrant may be achievable with such formulations, which can enhance ER downregulation and may provide an additional therapeutic benefit.

Inclusion complexes provided herein comprise fulvestrant and a cyclodextrin, or a salt thereof, or a solvate (e.g., hydrate) of the foregoing. The inclusion complexes may be used alone, or together with an additional pharmaceutical agent, in the treatment of a disease or condition provided herein, such as cancer. Other agents may also be incorporated with the inclusion complex, where applicable. For example, an inclusion complex may comprise a cyclodextrin and fulvestrant, with an antioxidant that is not itself a pharmaceutical agent but provides other benefits, such as stabilizing the complex over time, and which does not adversely effect the fulvestrant inclusion complex. Formulations comprising a fulvestrant inclusion complex, and optional additional pharmaceutical or other agents, together with a carrier, such as a pharmaceutically acceptable aqueous carrier, are also provided.

In some embodiments, an inclusion complex is an inclusion complex of a cyclodextrin and fulvestrant sulphoxide A, fulvestrant sulphoxide B, or a mixture of fulvestrant sulphoxide A and fulvestrant sulphoxide B. In a particular variation, a preparation of an inclusion complex is a preparation of a cyclodextrin and substantially pure fulvestrant sulphoxide A or substantially pure fulvestrant sulphoxide B. In another variation, a preparation of an inclusion complex is a preparation of a cyclodextrin and a mixture of fulvestrant sulphoxide A and fulvestrant sulphoxide B.

Examples of a cyclodextrin for use in the inclusion complex include, but are not limited to, water soluble unsubstituted or substituted alpha-cyclodextrin (ACD), beta-cyclodextrin (BCD), and gamma-cyclodextrin (GCD). Examples of substituted beta-cyclodoxtrins that may be employed in the inclusion complexes herein include, but are not limited to, methyl beta-cyclodextrin (MBCD), hydroxypropyl beta-cyclodextrin (HPBCD), and sulfobutylether beta-cyclodextrin (SBEBCD).). Examples of substituted gamma-cyclodextrins that may be employed in the inclusion complexes herein include, but are not limited to, hydroxypropyl gamma-cyclodextrin (HPGCD). Mixtures of cyclodextrins may also be employed. For example, a formulation comprising fulvestrant and a mixture of two or three or four or more cyclodextrins is also provided. Where a more than one cyclodextrin is employed, it may be of the same cyclodextrin class (e.g., two alpha-cyclodextrins) or different chemical classes (e.g., one alpha-cyclodextrin and one beta- or gamma-cyclodextrin). In one preferred embodiment, the cyclodextrin is hydroxypropyl beta-cyclodextrin (HPBCD) or methyl beta-cyclodextrin (MBCD).

In some embodiments, a cyclodextrin is obtained from a commercial source, including, but not limited to cyclodextrins sold under the following tradenames CAVASOL® W6 HP (Wacker Chemic AG, Munich, Germany), CAVASOL® W6 HP TL (Wacker Chemie AG, Munich, Germany), CAVAMAX® W6 Pharma (Wacker Chemie AG, Munich, Germany), CAVASOL® W7 HP (Wacker Chemie AG, Munich, Germany), CAVASOL® W7 HP Pharma (Wacker Chemic AG, Munich, Germany), CAVASOL® W7 HP TL (Wacker Chemie AG, Munich, Germany), CAVASOL W7 M (Wacker Chemie AG, Munich, Germany), CAVASOL® W7 M Pharma (Wacker Chemie AG, Munich, Germany), CAVASOL® W7 M TL (Wacker Chemie AG, Munich, Germany), CAVASOL® W8 HP (Wacker Chemie AG, Munich, Germany), CAVASOL®W8 HP Pharma (Wacker Chemie AG, Munich, Germany), KLEPTOSE® HPB (Roquette Pharma, Geneva, Ill.), and CAPTISOL® (Cyclex Pharmaceuticals, Inc. Lenexa, Kans.). In some embodiments, the cyclodextrin is CAVASOL® W7 M Pharma. In some embodiments, the cyclodextrin is KLEPTOSE® HPB.

The inclusion complex may comprise fulvestrant or a salt thereof, or a solvate (e.g., a hydrate or alcoholate) of the foregoing that is partially or completely included into the cavity of a cyclodextrin molecule. Accordingly, one or more cyclodextrin molecules may be associated with each fulvestrant molecule. The complex may exist in a variety of molar ratios, which may be dependent on a variety of physical factors during the formation of the complex, and be transitional and vary during formation.

In some embodiments, fulvestrant is fully included into the cavity of a cyclodextrin molecule. In some embodiments, fulvestrant is partially included into the cavity of a cyclodextrin molecule. In some embodiments of the inclusion complex, the molar ratio of the fulvestrant to cyclodextrin is from any of about 1:1 to about 1:300; about 1:1 to about 1:150; about 1:1 to about 1:100; about 1:1 to about 1:50; about 1:1 to about 1.25; about 1:1 to about 1:10; about 1:1 to about 1:5; about 1:1 to about 1:4; about 1:1 to about 1:3; about 1:1 to about 1:2.5; and about 1:1 to about 1:2, or is about any of 1:1, 1:2, and 1:3.

The inclusion complexes described herein may increase the solubility of fulvestrant. In one aspect, are provided methods for improving the solubility of fulvestrant in water comprising complexing fulvestrant with a cyclodextrin. In some embodiments, the solubility of fulvestrant in a fulvestrant inclusion complex, in deionized water at 20° C., is at least about 10-fold greater than the solubility of fulvestrant in uncomplexed form. In some embodiments, a fulvestrant inclusion complex increases the solubility of fulvestrant by at least any of about or by about 10-, 25-, 50-, 75-, 100-, 250-, 500-, 750-, 1000-, 1500-, 2000-, 3000-, or 4000-fold compared to the solubility of fulvestrant in uncomplexed form.

In some embodiments, the uncomplexed fulvestrant is present in an oil-based carrier (e.g., arachis oil, sesame oil, castor oil, or neutral oil (e.g., MIGLYOL® 810 or MIGLYOL® 812)), or in a non-aqueous ester solvent (e.g., benzyl benzoate, ethyl oleate, isopropyl myristate, isopropyl palmitate, or a mixture or combination of any thereof) and an alcohol (e.g., ethanol, benzyl alcohol, or a mixture or combination of any thereof). In some embodiments, an uncomplexed fulvestrant is obtained from a commercial source, including, but not limited to, the fulvestrant formulation sold as the tradename FASLODEX®.

The inclusion complexes described herein may provide improved pharmacokinetic properties for fulvestrant. Such changes in pharmacokinetic properties may result in desired therapeutic effects, such as a more rapid onset of therapeutic effect and/or less prolonged and/or reduced effects of a disease or condition for which fulvestrant treatment is obtained (e.g., cancer or systemic lupus erythematosus).

The inclusion complexes described herein may result in increased oral bioavailability of fulvestrant. In some embodiments, the oral bioavailability of fulvestrant from an inclusion complex comprising fulvestrant and a cyclodextrin is at least any of about or about 2%, 5%, 10%, 15%, 20%, 25%, 30%, 35%, 40%, 45%, 50%, 60%, 70%, 80%, or 90% greater than the oral bioavailability of fulvestrant alone under the same conditions. Methods of increasing oral bioavailability of fulvestrant by at least any of about or by about any of 2%, 5%, 10%, 15%, 20%, 25%, 30%, 35%, 40%, 45%, 50%, 60%, 70%, 80%, or 90% as compared to administration of uncomplexed fulvestrant under the same conditions are provided, such methods comprising administering fulvestrant in the form of an inclusion complex comprising fulvestrant and a cyclodextrin.

Bioavailability assessments and comparisons may be determined using standard techniques known in the art (e.g., measuring AUC(fulvestrant inclusion complex)/AUC(uncomplexed fulvestrant)×100). In some of these embodiments, the conditions for assessing the amount of increase in bioavailability of an inclusion complex of fulvestrant as compared to fulvestrant in uncomplexed form include orally or intranasally administering any of about 5 mg/mL, about 10 mg/mL, about 15 mg/mL, about 20 mg/mL, about 25 mg/mL, about 30 mg/mL, about 35 mg/mL, about 40 mg/mL, or about 50 mg/mL of fulvestrant (in the appropriate complexed or uncomplexed form) in a carrier and at room temperature. In some embodiments, the fulvestrant can be administered at room temperature in an aqueous solution (e.g., WFI) in the presence or absence of a buffer.

The inclusion complexes described herein may result in an increased $C_{max}$ of fulvestrant following administration of an amount of fulvestrant as an inclusion complex when compared to administering the same amount of fulvestrant, via the same route and under the same conditions, in uncomplexed form. The inclusion complexes described herein may also result in an increased $C_{max}$ of fulvestrant following administration of an amount of fulvestrant as an inclusion complex when compared to administering the same amount of fulvestrant via a different administration route, in uncomplexed form. For example, $C_{max}$ of fulvestrant may be increased upon oral and/or intranasal administration of an amount of fulvestrant as an inclusion complex with a cyclodextrin when compared to administration of the same amount of uncomplexed fulvestrant as an intramuscular injection. In some embodiments, the inclusion complexes described herein may result in an increased $C_{max}$ for fulvestrant within about 3 hours after oral administration of a fulvestrant inclusion complex to an individual. In some embodiments, the $C_{max}$ of fulvestrant from an inclusion complex comprising fulvestrant and a cyclodextrin is at least about or about any of 4, 5, 6, 7, 8, 9, 10, 11, 12, 13, 15, 17, 19, 21, 23, 25, 27, 29, 31, 33, 35, 37, 40, 50, 60, 70, 80, 90, or 100 times greater than the $C_{max}$ of uncomplexed fulvestrant administered in the same amount and under the same conditions as the inclusion complex. In some of these embodiments, the conditions comprise orally or intranasally administering any of about 5 mg/mL, about 10 mg/mL, about 15 mg/mL, about 20 mg/mL, about 25 mg/mL, about 30 mg/mL, about 35 mg/mL, about 40 mg/mL, or about 50 mg/mL of fulvestrant (in the appropriate complexed or uncomplexed form) at room temperature in an aqueous solution (e.g., WFI). Methods of increasing $C_{max}$ in accordance with the descriptions herein are also provided.

The inclusion complexes described herein may result in a decreased $T_{max}$ for fulvestrant following administration. In some embodiments, the $T_{max}$ of fulvestrant from an inclusion complex comprising fulvestrant and a cyclodextrin is at least about or about any of 2%, 5%, 10%, 15%, 20%, 25%, 30%, 35%, 40%, 45%, 50%, 60%, 70%, 80%, or 90% lower than the $T_{max}$ of fulvestrant administered alone under the same conditions. The inclusion complexes described herein may also result in a decrease in $T_{max}$ following administration of an amount of fulvestrant as an inclusion complex when compared to administering the same amount of fulvestrant via a different administration route, in uncomplexed form. For example, $T_{max}$ of fulvestrant may be decreased upon oral and/or intranasal administration of an amount of fulvestrant as an inclusion complex with a cyclodextrin when compared to administration of the same amount of fulvestrant as an intramuscular injection. The value of $T_{max}$ upon oral and/or intranasal administration of an amount of fulvestrant as an inclusion complex may be at least about or about any of 2%, 5%, 10%, 15%, 20%, 25%, 30%, 35%, 40%, 45%, 50%, 60%, 70%, 80%, or 90% lower than the $T_{max}$ obtained by administration of the same amount of uncomplexed fulvestrant as an intramuscular injection. In some of these embodiments, the conditions comprise orally or intranasally administering any of about 5 mg/mL, about 10 mg/mL, about 15 mg/mL, about 20 mg/mL, about 25 mg/mL, about 30 mg/mL, about 35 mg/mL, about 40 mg/mL, or about 50 mg/mL of fulvestrant (in the appropriate complexed or uncomplexed form) at room temperature in an aqueous solution (e.g., WFI). Methods of decreasing $T_{max}$ in accordance with the descriptions herein are also provided.

The inclusion complexes described herein may result in decreasing the therapeutic time of onset for fulvestrant such that the therapeutic effect occurs sooner with a fulvestrant inclusion complex as compared to fulvestrant administered in an uncomplexed form. In one embodiment, the therapeutic time of onset of fulvestrant from an inclusion complex comprising fulvestrant and a cyclodextrin is decreased by at least about or about any of 2%, 5%, 10%, 15%, 20%, 25%, 30%, 35%, 40%, 45%, 50%, 60%, 70%, 80%, or 90% than the therapeutic time of onset of uncomplexed fulvestrant administered in the same amount and under the same conditions. In other embodiments an inclusion complex of fulvestrant decreases the therapeutic time of onset for fulvestrant by at least about or about any of 2%, 5%, 10%, 15%, 20%, 25%, 30%, 35%, 40%, 45%, 50%, 60%, 70%, 80%, or 90% as compared to the therapeutic time of onset of uncomplexed fulvestrant administered in the same amount as an intramuscular injection. In one aspect, the fulvestrant inclusion complex is provided by oral or intranasal administration. In some of these embodiments, the conditions comprise orally or intranasally administering any of about 5 mg/mL, about 10 mg/mL, about 15 mg/mL, about 20 mg/mL, about 25 mg/mL, about 30 mg/mL, about 35 mg/mL, about 40 mg/mL, or about 50 mg/mL of fulvestrant (in the appropriate complexed or uncomplexed form) at room temperature in an aqueous solution (e.g., WFI). Methods of decreasing therapeutic time of onset for fulvestrant in accordance with the descriptions herein are also provided.

In some embodiments, the inclusion complex comprising fulvestrant and a cyclodextrin is in substantially pure form. In one variation, a preparation of substantially pure inclusion complex is provided wherein the preparation contains about or less than about any one of 15%, 12%, 10%, 8%, 5%, 3%, 2%, 1% and 0.5% impurity.

The inclusion complexes described herein, formulations thereof, and methods include all salt and solvate forms. For example, an inclusion complex may comprise a compound of formula (I) and/or a salt thereof. An inclusion complex may also comprise a solvate of a compound of formula (I) or a salt thereof. Solvates may contain either stoichiometric or non-stoichiometric amounts of a solvent, and are often formed during the process of crystallization. In one aspect, a solvent is water and the solvate is a hydrate. In another aspect, a solvent is an alcohol and the solvate is an alcoholate. In some embodiments, the inclusion complexes described herein can exist in unsolvated forms as well as solvated forms. The inclusion complexes may also include hydrated forms or salt forms.

Methods of Preparation

Also provided are methods of preparing the inclusion complexes described herein. In some instances inclusion complexes may be prepared on the basis of liquid state, solid state or semi-solid state reaction between the components. This may be accomplished by dissolving the cyclodextrin and fulvestrant in a suitable solvent or mixture of solvents. If desired, an inclusion complex so obtained may be subsequently isolated by crystallization, evaporation, spray drying or freeze drying. In a solid state method, the two components may be screened to uniform particle size and thoroughly mixed, at which point they may be ground in a high energy mill with optional heating, screening and homogenization. In a semi-solid state, the two components may be kneaded in the presence of small amounts of a suitable solvent, and the complex so-formed, is oven dried, screened and homogenized. The liquid state reaction generally provides optimum conditions for completeness of reaction.

In one aspect is provided a method of producing an inclusion complex comprising fulvestrant and a cyclodextrin by admixing fulvestrant with a cyclodextrin. In some embodiments, the method further comprises adding a solvent, mixed solvent, or buffer to fulvestrant, the cyclodextrin, and/or mixture thereof.

In the preparation of a fulvestrant inclusion complex, the suitable amount of solvent, mixed solvent, or buffer may be added directly to a solid mixture of fulvestrant and the cyclodextrin. Alternatively, the solvent, mixed solvent, or buffer may be added to either fulvestrant or the cyclodextrin, and then added to the other of fulvestrant and the cyclodextrin. In some embodiments, the solvent, mixed solvent, or buffer may be added independently to each of fulvestrant and cyclodextrin, followed by combining fulvestrant and the cyclodextrin.

In one aspect, the method of producing an inclusion complex of fulvestrant and a cyclodextrin comprises the steps of: (a) admixing fulvestrant and a cyclodextrin; and (b) adding a suitable amount of solvent, mixed solvent, or buffer to the mixture of step (a) and mixing until a suspension or solution is formed.

In some embodiments, a buffer is employed. For example, a formulation comprising a fulvestrant inclusion complex for intranasal administration in one aspect further comprises a buffer as detailed herein. Suitable buffers include, without limitation, phosphate buffers (e.g., phosphate-citrate), potassium hydrogen phthalate buffers, and acetate buffers. In some embodiments, the buffer is a phosphate-citrate buffer. In some embodiments, the added buffer and/or resulting suspension or solution has a pH between any of about 1.0, 2.0, and 3.0 and about 8.0, 9.0 or 10.0; about 3.0 and about 8.0, about 4.0 and about 6.0, about 4.5 and about 5.5; or a pH of greater than, less than, or about any of 1.0, 2.0, 3.0, 3.5, 4.0, 4.5, 5.0, 5.5, 6.0, 7.0, 7.5, 8.0, 9.0, or 10.0. In one aspect, a formulation comprising a fulvestrant inclusion complex for intranasal administration comprises a buffer and the formulation has a pH of between about 5.0 and about 8.0. In some embodiments, a solvent is employed. A solvent in one aspect is an organic solvent or water. Suitable organic solvents are known to those of skill in the art and include, but are not limited to, low chain alcohols (e.g. methanol; ethanol; i-propanol) and acetone. In some embodiments, the solvent is a polar solvent, such as water (e.g., $ddH_2O$), methanol, ethanol, and i-propanol. In some embodiments, a mixed solvent is employed. A mixed solvent in one aspect comprises an organic solvent or water. In one aspect, a mixed solvent is a mixture of water and an organic solvent. Suitable solvents, mixed solvents, or buffers include 100% of $ddH_0O$, or $ddH_2O$ or buffer together with ethanol or methanol (1-99%). Various combinations of solvent, mixed solvent, or buffer for optimizing the production of an inclusion complex of fulvestrant and a cyclodextrin can be determined by persons skilled in the art in view of the methods described herein.

For the methods of producing an inclusion complex of fulvestrant and a cyclodextrin, fulvestrant may be admixed with the cyclodextrin at a molar ratio from about 0.2:1 to about 1:300. In some embodiments, the molar ratio is about 0.5:1 to about 1:150, or about 1:1 to about 1:75, or about 1:1 to about 1:50, or about 1:1 to about 1:25, or about 1:1 to about 1:10, or about 1:1 to about 1:5, or about 1:1 to about 1:3, or about 1:1 to about 1:2, or any of about 1:1, 1:2, 1:3, 1:4, 1:5, 1:6, and 1:7.

In some embodiments of the methods of producing an inclusion complex, the solvent, mixed solvent, or buffer is heated to less than, greater than, or about any of 25° C., 30° C., 35° C., 40° C., 45° C., 50° C., 55° C., 60° C., 65° C., 75° C., or 80° C. (e.g., before, during and/or after mixing). The solvent, mixed solvent, or buffer may be heated prior to and/or after being added to fulvestrant and/or cyclodextrin. In some embodiments, the solvent, mixed solvent, or buffer is heated greater than the preferred temperature for less than, greater than, or about any of 0.1 hr, 0.2 hr, 0.3 hr, 0.5 hr, 0.75 hr, 1 hr, 2 hr, 3 hr, 4 hr, 5 hr, 7 hr, 10 hr, 15 hr, 24 hr, 36 hr, or 48 hr.

During the formation of the inclusion complex between fulvestrant and a cyclodextrin, a suitable polymer may be added which may enhance the solubility and/or complexation ability of fulvestrant and cyclodextrin inclusion complex. Accordingly, in some embodiments of the methods of producing an inclusion complex, a step of admixing fulvestrant and a cyclodextrin further comprises admixing a suitable polymer. Suitable polymers include, for example, polyvinylpyrrolidone, hydroxypropyl methylcellulose, carboxymethylcellulose, and PLASDONE® Povidone, and derivatives thereof. In some embodiments, the suitable polymer is a water-soluble polymer.

In some embodiments of the methods of producing an inclusion complex, the mixing is continued for at least any of about 0.1 hr, 0.2 hr, 0.3 hr, 0.5 hr, 0.75 hr, 1 hr, 2 hr, 4 hr, 10 hr, 24 hr, 36 hr, or 48 hr following formation of the suspension or solution. If heat is applied to the solvent, mixed solvent, or buffer during a method of producing an inclusion complex, the described mixing of the components may occur prior to, simultaneously with, and/or after the application of said heat.

In some embodiments, the method of producing an inclusion complex further comprises a step for drying the product obtained from the steps of a) admixing fulvestrant and a cyclodextrin and b) adding a suitable amount of a solvent, mixed solvent or buffer to the mixture. In some embodiments, the drying comprises evaporation. In some embodiments, the evaporation occurs for greater than, less than, or about any of 0.1 hr, 0.25 hr, 0.5 hr, 1 hr, 2 hr, 5 hr, 10 hr, 1 day, or 5 days. In some embodiments, the evaporation is conducted under vacuum (e.g., less than any of about 0.75 atm, 0.5 atm, or 0.25 atm). In some embodiments, the evaporation is conducted under atmospheric pressure. In some embodiments, the drying comprises dry heat. In some embodiments, the drying comprises spray-drying. In some embodiments, the drying comprises freeze-drying. In some embodiments, the drying comprises spray-granulation.

In one aspect, is provided a method of producing an inclusion complex between fulvestrant and a cyclodextrin comprising the steps of: (a) mixing the appropriate amount of fulvestrant and cyclodextrin with or without a suitable polymer; (b) adding a suitable amount of solvent, mixed solvent, and/or buffer to the mixture of step (a) with vigorous mixing until a paste or a slurry is formed; (c) continuing the mixing with further addition of solvent (e.g., water), mixed solvent, or buffer if necessary to maintain the paste or the slurry consistency, for a suitable period of time to form the inclusion complex; and (d) drying the product of step (c). In some embodiments of step (b), the buffer is a phosphate-citrate buffer and the pH is about 5. In some embodiments, the solvent added during steps (b) and (c) is heated. In some embodiments, wherein the solvent, mixed solvent, or buffer is deionized water and/or a buffer, the deionized water and/or a buffer is heated to about 60° C. In some embodiments, the mixing is preferably continued for a period of time greater than 0.2 hours. In some embodiments, the vigorous mixing until a paste or a slurry is formed is conducted at about 60° C.

In another aspect, is provided a method of producing an inclusion complex between fulvestrant and a cyclodextrin comprising the steps of: (a) mixing suitable amounts of fulvestrant and a cyclodextrin with or without a suitable polymer; (b) adding of a suitable solvent, mixed solvent, and/or buffer to the mixture of step (a) with mixing until a slurry, suspension or solution is formed; and (c) allowing the formation of the inclusion complex by evaporation of the water over a period of time. In some embodiments of step (b), the buffer is a phosphate-citrate buffer and the buffer pH is about 5. In some embodiments, the solvent added during step (b) is heated. In some embodiments, wherein the solvent, mixed solvent, or buffer is deionized water and/or a buffer, the deionized water and/or a buffer is heated to about 60° C. In some embodiments of step (c), heat is applied to increase the evaporation rate. In some embodiments, the evaporation is conducted at 40° C. In some embodiment, evaporation in step (c) occurs for greater than about 1 hour. In some embodiments, the evaporation is conducted under vacuum.

In another aspect, is provided a method of producing an inclusion complex between fulvestrant and a cyclodextrin comprising the steps of: (a) mixing suitable amounts of fulvestrant and a cyclodextrin with or without a suitable polymer; (b) adding of a suitable solvent, mixed solvent, and/or buffer to the mixture of step (a) with mixing until a slurry, suspension or solution is formed; and (c) spray-drying the slurry, suspension or solution to obtain a solid drug-cyclodextrin inclusion complex. In some embodiments, the buffer is a phosphate-citrate and the buffer pH is about 5. In some embodiments, the suitable solvent, mixed solvent, and/or buffer added during step (b) is heated. In some embodiments, wherein the solvent, mixed solvent, or buffer is deionized water and/or a buffer, the deionized water and/or a buffer is heated to about 60° C.

In another aspect, is provided a method of producing an inclusion complex between fulvestrant and a cyclodextrin comprising the steps of: (a) mixing suitable amounts of fulvestrant and a cyclodextrin with or without a suitable polymer; (b) adding of a suitable solvent, mixed solvent, and/or buffer to the mixture of step (a) with mixing until a solution is formed; and (c) freeze-drying the solution to obtain a solid drug-cyclodextrin inclusion complex. In some embodiments, the buffer is a phosphate-citrate buffer and the buffer pH is about 5. In some embodiments, the solvent, mixed solvent, and/or buffer added during step (b) is heated. In some embodiments, wherein the solvent, mixed solvent, or buffer is deionized water and/or a buffer, the deionized water and/or a buffer is heated to about 60° C.

In another aspect, is provided a method of producing an inclusion complex between fulvestrant and a cyclodextrin comprising the steps of: (a) mixing suitable amounts of fulvestrant and a cyclodextrin with or without a suitable polymer; (b) adding of a suitable solvent, mixed solvent, and/or buffer to the mixture of step (a) with mixing until a slurry, suspension or solution is formed; (c) adding inactive pharmaceutical excipients to the slurry, suspension or solution, with continued mixing and (d) spray-granulating the slurry, suspension or solution to obtain solid particles, suitable for formulation into an oral formulation, containing a solid drug-cyclodextrin inclusion complex. In some embodiments, the buffer is a phosphate-citrate buffer and the buffer pH is about 5. In some embodiments, the solvent, mixed solvent, or buffer added during step (b) may be heated. In some embodiments, wherein the solvent, mixed solvent, or buffer is deionized water and/or a buffer, the deionized water and/or a buffer is heated to about 60° C. The inactive pharmaceutical excipients included to produce an oral formulation according to step (c) may include commonly used pharmaceutical excipients commonly used in the art, and/or those described herein.

In another aspect, is provided a method of producing an inclusion complex between fulvestrant and a cyclodextrin comprising the steps of: (a) mixing suitable amounts of fulvestrant and cyclodextrin with or without a suitable polymer; (b) adding a suitable solvent, mixed solvent, and/or buffer to the mixture of step (a) with mixing until a solution is formed; (c) producing a liquid oral or intranasal formulation. Inactive pharmaceutical excipients may be added to the solution, containing the liquid drug-cyclodextrin inclusion complex. In some embodiments, the buffer is a phosphate-citrate buffer and the buffer pH is about 5. In some embodiments, the solvent, mixed solvent, and/or buffer added during step (d) is heated. In some embodiments, wherein the solvent, mixed solvent, or buffer is deionized water and/or a buffer, the deionized water and/or a buffer is heated to about 60° C. The inactive pharmaceutical excipients included to produce a liquid oral or intranasal formulation according to step (c) may include commonly used pharmaceutical excipients commonly used in the art, and/or those described herein.

In some embodiments of the methods for producing an inclusion complex between fulvestrant and a cyclodextrin described above, greater than any of about 10%, 15%, 20%, 30%, 40%, 50%, 60%, 70%, 80%, 85%, 90%, 95%, 97%, 98%, or 99% of fulvestrant is in complexed form.

A product obtained by any of the preceding processes is also provided for herein.

Formulations

The inclusion complexes described herein (e.g., an inclusion complex of fulvestrant with a cyclodextrin) may be used in the preparation of a composition or formulation, such as a pharmaceutical composition or formulation, by combining an inclusion complex described with at least one or any combination of more than one of a pharmaceutical acceptable carrier, excipient, stabilizing agent and/or other agent, which are known in the art, for use in the methods of treatment, methods of administration, and dosage regimes described herein. A pharmaceutically acceptable carrier may include, for example, solvents, mixed solvents, complexing agents, fillers, stabilizers, diluents, granulating agents, disintegrants, lubricants, glidants, pH-modifiers, tonicity modifiers, adjuvants, binders, etc., known to the skilled artisan that are suitable for administration to an individual (e.g., a human). Combinations of two or more carriers are also contemplated.

The pharmaceutically acceptable carrier(s) and any additional components, as described herein, should be compatible for use in the intended route of administration (e.g., oral, parenteral, intranasal, or sublingual) for a particular dosage form. Such suitability will be recognized by the skilled artisan, particularly in view of the teaching provided herein. The formulations may vary or be tailored according to the condition to be treated, the amount of compound to be administered, the condition of the individual, and other variables that will readily be apparent to one of ordinary skill in the art in view of the teachings provided herein. The inclusion complexes may be formulated, for example, as solid, semi-solid, and liquid dosage forms, such as tablets, pills, powders, liquid solutions or suspensions, suppositories, injectable and infusible solutions, and sprays. The preferred form depends on the intended mode of administration and therapeutic application. The following formulations, additives, and methods are merely exemplary and are in no way limiting.

Fulvestrant described herein may be formulated with a cyclodextrin and may comprise one or more of the favorable properties described for the inclusion complexes herein (e.g., increased solubility). In some embodiments, fulvestrant is in the uncomplexed form in the presence of a cyclodextrin. In some embodiments, is provided a mixture of fulvestrant in both complexed and uncomplexed form with a cyclodextrin (e.g., a molar ratio mixture of greater than, less than, or any of about 1:300, 1:150, 1:75, 1:50, 1:25, 1:20, 1:15 1:10, 1:7.5, 1:5, 1:3, 1:2, 1:1, 2:1, 3:1, 4:1, 5:1, 7.5:1, 10:1, 15:1, 25:1, 50:1, 100:1, 150:1 or 300:1 of complexed fulvestrant to uncomplexed fulvestrant, respectively). Accordingly, in one aspect is provided a formulation comprising fulvestrant, a cyclodextrin, and a carrier. In some embodiments, the formulation comprises an effective amount of fulvestrant, cyclodextrin, and a carrier. The formulation may comprise a molar ratio of cyclodextrin to fulvestrant that is greater than, less than, or any of about 1:1, 2:1, 3:1, 4:1, 5:1, 7.5:1, 10:1, 15:1, 25:1, 50:1, 75:1, 100:1, 150:1 or 300:1. Additionally, the formulation comprising the fulvestrant, a cyclodextrin, and a carrier may be further formulated in any manner described herein for the inclusion complex formulations, and may be used in any of the methods described herein, as well as at any dosage described herein, for the inclusion complexes and/or inclusion complex formulations (e.g., to treat a condition, such as cancer or systemic lupus erythematosus). These formulations also may provide improved pharmacokinetic properties as described herein (e.g., bioavailability, $C_{max}$, $T_{max}$, and time of onset) when compared to uncomplexed fulvestrant administered under the same conditions.

In some embodiments, the formulation comprising fulvestrant and a cyclodextrin, a complex of fulvestrant with a cyclodextrin, or a mixture thereof, is a sterile formulation.

Additives used with the inclusion complexes described herein (e.g., an inclusion complex of fulvestrant with a cyclodextrin) include, for example, one or more excipients (e.g., one or more excipients), antioxidants (e.g., one or more antioxidants), stabilizers (e.g., one or more stabilizers), preservatives (e.g., one or more preservatives, including antimicrobial preservatives), pH adjusting and buffering agents (e.g., one or more pH adjusting and/or buffering agents), tonicity adjusting agents (e.g., one or more tonicity adjusting agents), thickening agents (e.g., one or more thickening agents), suspending agents (e.g., one or more suspending agents), binding agents (e.g., one or more binding agents), viscosity enhancing agents (e.g., one or more viscosity enhancing agents), sweetening agent (e.g., one or more sweetening agent) and the like, either alone or together with one or more additional pharmaceutical agents, provided that the additional components are pharmaceutically acceptable. In some embodiments, the formulation may include combinations of two or more of the additional components as described herein (e.g., any of 2, 3, 4, 5, 6, 7, 8, or more additional components).

In some embodiments, antioxidants include, but are not limited to, ascorbyl palmitate, butylated hydroxyanisole, butylated hydroxytoluene, malic acid, propyl gallate, sodium bisulfite, sodium sulfite, sodium metabisulfite, potassium metabisulfite, potassium bisulfite, sodium thiosulfate, sodium formaldehyde sulfoxylate, L-ascorbic acid, D-ascorbic acid, acetylcysteine, cysteine, thioglycerol, thioglycoUic acid, thiolactic acid, thiourea, dithiothreitol, dithiocrythreitol, glutathione, nordihydroguaiaretic acid, tocopherol, sodium ascorbate, hypophosphorous acid, and fumaric acid. In some embodiments, the antioxidant is selected from the group consisting of sodium bisulfite, sodium sulfite, sodium metabisulfite, potassium metabisulfite, potassium bisulfite, sodium thiosulfate, sodium formaldehyde sulfoxylate, L-ascorbic acid, D-ascorbic acid, acetylcysteine, thioglycerol, thioglycoUic acid, thiolactic acid, thiourea, dithiothreitol, dithiorythreitol, glutathione, nordihydroguaiarctic acid, sodium ascorbate and hypophosphorous acid.

In some embodiments, the antioxidant is a dietary antioxidant, including, but not limited to, vitamin E, vitamin C, beta-carotene, and selenium.

In some embodiments, the additives include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, polyvinylpyrrolidinone, low melting waxes, ion exchange resins, and the like, as well as combinations of any two or more thereof. Other suitable pharmaceutically acceptable excipients are described in REMINGTON'S PHARMACEUTICAL SCIENCES, Mack Pub. Co., New Jersey 18$^{th}$ edition (1996), HANDBOOK OF PHARMACEUTICAL EXCIPIENTS, Pharmaceutical Press and American Pharmacists Association, 5 edition (2006), and REMINGTON: THE SCIENCE AND PRACTICE OF PHARMACY, Lippincott Williams & Wilkins, Philadelphia, 20 edition (2003) and 21$^{st}$ edition (2005).

Formulations suitable for oral administration may comprise, for example, (a) liquid solutions, such as an effective amount of fulvestrant or cyclodextrin inclusion complex thereof dissolved in diluents, such as water, saline, or other ingestable liquid such as orange juice, (b) capsules, sachets or tablets, each containing a predetermined amount of fulvestrant or inclusion complex thereof, as solids or granules, (c) suspensions in an appropriate liquid, (d) suitable emulsions, and (e) powders. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise fulvestrant or an inclusion complex thereof in a flavor, usually sucrose and acacia or tragacanth, as well as pastilles comprising fulvestrant or an inclusion complex thereof in an inert base, such as gelatin and glycerin, or sucrose and acacia, emulsions, gels, and the like containing, in addition to the active ingredient, such excipients as are known in the art. Oral formulations may include any suitable dosage, including those described herein, such as any of about 0.1 mg, 1 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 25 mg, 30 mg, 35 mg, 40 mg, 45 mg, 50 mg, 75 mg, 100 mg, 150 mg, 200 mg, 250 mg, 275 mg, 300 mg, 350 mg, 400 mg, 450 mg, or 500 mg of fulvestrant per unit dose. As described below, the formulations may be used for the treatment of a condition (e.g., cancer or systemic lupus erythematosus). Solid dosage forms for oral administration may be particularly useful for the treatment of cancer.

The inclusion complexes can be enclosed in a hard or soft capsule, can be compressed into tablets, or can be incorporated with beverages or food or otherwise incorporated into the diet. Capsules can be formulated by mixing the inclusion complex with an inert pharmaceutical diluent and inserting the mixture into a hard gelatin capsule of the appropriate size. If soft capsules are desired, a slurry, suspension or solution of the inclusion complex may be encapsulated by machine into a gelatin capsule.

Liquid dosage forms for oral administration may include pharmaceutically acceptable solutions, suspensions, syrups, and elixirs containing inert diluents commonly used in the art, such as water or buffers. Such formulations may also comprise adjuvants, such as wetting, emulsifying, suspending, antioxidants, preservatives (e.g., antimicrobial preservative), enhancing (e.g., viscosity-enhancing), sweetening, flavoring, and perfuming agents. Liquid dosage forms of the inclusion complexes for oral administration may be particularly useful for the treatment of cancer.

It is understood that when a formulation comprising a fulvestrant cyclodextrin inclusion complex is employed, wherein the formulation further comprises an additional agent, which may be an additional pharmaceutical or other agent, that the additional agent may be employed in a manner that reduces the number or severity of adverse effects that the additional agent may have on the fulvestrant cyclodextrin inclusion complex. For example, although an additional agent may confer a benefit on a formulation comprising a fulvestrant cyclodextrin inclusion complex, such an agent may also have the potential to displace fulvestrant in the inclusion complex or otherwise prevent or reduce the quality of fulvestrant inclusion. Such agents may still confer a benefit but their adverse consequences may be reduced or avoided if used in reduced amounts. Alternatively, additional agents may be selected such that the additional agent or combination thereof is less likely to adversely affect the inclusion complex.

Formulations suitable for parenteral administration include aqueous and non-aqueous, isotonic sterile injection solutions, which can contain anti-oxidants, buffers, bacteriostats, and solutes that render the formulation compatible with the blood of the intended recipient, and aqueous and non-aqueous sterile suspensions that can include suspending agents, solubilizers, thickening agents, stabilizing agents, and preservatives. The formulations can be presented in unit-dose or multi-dose sealed containers, such as ampules and vials, and can be stored in a freeze-dried (lyophilized) condition requiring only the addition of the sterile liquid for reconstitution (e.g., water for injection), immediately prior to use. Extemporaneous injection solutions and suspensions can be prepared from sterile powders, granules, and tablets of the kind previously described.

Injectable preparations (for example, sterile injectable aqueous or oleaginous suspensions) may be formulated according to the known art using suitable dispersing or wetting agents and suspending agents. The sterile injectable preparation may also be a sterile injectable solution or suspension in a nonioxic parenterally acceptable diluent or solvent, for example, as a solution in propylene glycol. The sterile injectable preparation may also be a sterile powder to be reconstituted using acceptable vehicles prior to administration. Among the acceptable vehicles and solvents that may be employed are water, Ringer's solution, and isotonic sodium chloride solution. In addition, sterile, fixed oils may be employed as a solvent or suspending medium. For this purpose any bland fixed oil may be employed including synthetic mono- or diglycerides. In addition, fatty acids such as oleic acid may be used in the preparation of injectables.

Formulation of the inclusion complex in liquid form (for oral administration, parenteral administration, intranasal administration, or otherwise) may have a pH in the range of about 1.0 to about 10.0, including for example pH ranges of any of about 5.0 to about 8.0, about 5.0 to about 7.0, about 5.0 to about 6.0, about 6.5 to about 7.5, and about 6.5 to about 7.0. In some embodiments, the pH of the composition is formulated to no less than about 6, 5, or 4, including for example a pH of any of about 8, 7.5, 7, 6.5, 6, 5.5, 5, 4.5, or 4. The formulation can also be made to be isotonic with blood by the addition of a suitable tonicity modifier, such as glycerol.

The inclusion complexes may also be formulated for administration by inhalation. Formulations suitable for aerosol administration which comprise the inclusion complex may include, for example, aqueous and non-aqueous, isotonic sterile solutions, which can contain anti-oxidants, buffers, bacteriostats, and solutes, as well as aqueous and non-aqueous sterile suspensions that can include suspending agents, solubilizers, thickening agents, stabilizing agents, and preservatives, alone or in combination with other suitable components, which can be made into aerosol formulations to be administered via inhalation. These aerosol formulations can be placed into pressurized acceptable propellants, such as dichlorodifluoromethane, propane, nitrogen, and the like. They also can be formulated as pharmaceuticals for non-pressured preparations, such as in a nebulizer or an atomizer.

The inclusion complexes may also be formulated in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The inclusion complexes may also be formulated for topical administration, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-applied transdermal patches may also be used.

Also provided are unit dosage forms comprising the inclusion complexes and formulations described herein. These unit dosage forms can be stored in a suitable packaging in single or multiple unit dosages and may also be further sterilized and sealed. For example, the pharmaceutical formulation (e.g., a dosage or unit dosage form of a pharmaceutical formulation) may include (i) a mixture of fulvestrant with a cyclodextrin, and/or an inclusion complex thereof, and (ii) a pharmaceutically acceptable carrier. In some variations, the amount of fulvestrant within the formulation is in any of the following ranges: about 0.1 to about 50 mg, about 1 to about 50 mg, about 5 to about 50 mg, about 20 to about 50 mg, about 50 to about 100 mg, about 100 to about 125 mg, about 125 to about 150 mg, about 150 to about 175 mg, about 175 to about 200 mg, about 200 to about 225 mg, about 225 to about 250 mg, about 250 to about 300 mg, about 300 to about 350 mg, about 350 to about 400 mg, about 400 to about 450 mg, about 450 to about 500 mg, about 500 mg to about 550 mg, about 550 mg to about 600 mg, about 600 mg to about 650 mg, about 650 mg to about 700 mg, about 700 mg to about 750 mg, about 750 mg to about 800 mg. In some embodiments, the amount of fulvestrant within the formulation (e.g., a dosage or unit dosage form) is in the range of about 1 mg to about 500 mg, such as any of about 5 mg to about 250 mg, about 20 mg to about 400 mg, or about 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, or 800 mg. In some of these embodiments, the formulation may comprise a molar ratio of a cyclodextrin to fulvestrant that is greater than, less than, or any of about 1:1, 2:1, 3:1, 4:1, 5:1, 7.5:1, 10:1, 15:1, 25:1, 50:1, 75:1, 100:1, 150:1 or 300:1. For example, in some embodiments wherein the amount of the amount of fulvestrant within the formulation is in the range of about 1 mg to about 800 mg, such as any of about 5 mg to about 700 mg, 20 mg to about 500 mg, or about 20 mg, 25 mg, 50 mg, 75 mg, 100 mg, 150 mg, 200 mg, 250 mg, 300, 350 mg, 400 mg, 450 mg, 500 mg, 550 mg, 600 mg, 650 mg, 700 mg, 750 mg, or 800 mg, the amount of a cyclodextrin in the formulation may be any of about 5 mg to about 2500 mg, such as any of about 15 mg to about 1500 mg, about 30 mg to about 750 mg, about 60 mg to about 300 mg, about 100 mg to about 200 mg, or about 60 mg, 75 mg, 100 mg, 125 mg, 150 mg, 200 mg, 225 mg, 250 mg, 275 mg or 300 mg. In some embodiments, the carrier is suitable for parental administration (e.g., intravenous administration). In some embodiments, the carrier is suitable for intramuscular administration. In some embodiments, the carrier is suitable for oral administration. In some embodiments, the carrier is suitable for intranasal administration. In some embodiments, the carrier is suitable for sublingual, rectal or vaginal administration. In some embodiments, fulvestrant of the inclusion complex is the only pharmaceutically active agent for the treatment of the condition (e.g., cancer or systemic lupus erythematosus) that is contained in the formulation.

In some embodiments, are provided dosage forms (e.g., a unit dosage form) for the treatment of cancer or systemic lupus erythematosus, comprising (i) a mixture of a fulvestrant with a cyclodextrin, and/or an inclusion complex thereof wherein the amount of fulvestrant is in the range of about 0.1 mg to about 500 mg per unit dose, and (ii) a pharmaceutically acceptable carrier. In some embodiments, the amount of fulvestrant in the unit dosage form includes any of about 0.1 mg, 1 mg, 5 mg, 6 mg, 7 mg, 8 mg, 9 mg, 10 mg, 11 mg, 12 mg, 13 mg, 14 mg, 14 mg, 15 mg, 16 mg, 17 mg, 18 mg, 19 mg, 20 mg, 25 mg, 30 mg, 35 mg, 40 mg, 45 mg, 50 mg, 75 mg, 100 mg, 150 mg, 200 mg, 250 mg, 275 mg, 300 mg, 350 mg, 400 mg, 450 mg, 500 mg, 550 mg, 600 mg, 650 mg, 700 mg, 750 mg, or 800 mg of fulvestrant.

In some embodiments, are provided formulations of the inclusion complexes described herein comprising one or more of a complexing agent, a filler, a diluent, a granulating agent, a disintegrant, a lubricant, or a glidant. The complexing agent, filler, diluent, granulating agent, disintegrant, lubricant, or glidant may be chosen from among the ingredients listed in Table 1. In some embodiments, formulations may contain zero, one, or more than one ingredient from each use category in Table 1. Formulations may additionally contain other complexing agents, fillers, diluents, granulating agents, disintegrants, lubricants, or glidants not listed in Table 1. Formulations may also contain additional ingredients that are not complexing agents, fillers, diluents, granulating agents, disintegrants, lubricants, or glidants.

TABLE 1

| Use | Ingredients |
| --- | --- |
| Complexing agent | Sodium hydrogen carbonate; ethanol; methanol |
| Filler/diluent | Microcrystalline cellulose; calcium carbonate; glucose; calcium hydrogen phosphate; lactose; mannitol; sodium chloride; sucrose; dextrates; microfine cellulose; modified starch; sucrose-dextrin co-precipitate |
| Granulating agent | *Acacia* mucilage; glucose; gelatine; povidone (PVP); starch mucilage; sucrose; tragacanth mucilage |
| Disintegrant | Sodium hydroxymethylcellulose; alginic acid; sodium alginate; aluminium magnesium silicate; carbon dioxide; carmellose sodium; cationic exchange resins; croscarmellose sodium; microcrystalline cellulose; modified starch; sodium lauryl sulphate; sodium glycine carbonate; sodium starch glycollate; starch |
| Lubricant | Magnesium stearate; calcium stearate; stearic acid; fumaric acid; hydrogenated vegetable oil; liquid paraffin; magnesium lauryl sulphate; macrogol 4000 and 6000; sodium benzoate; sodium lauryl sulphate; sodium stearyl fumarate |
| Glidant | Colloidal silica; talc |

Exemplary formulations are shown in Table 2.

TABLE 2

| | Formulation 1 | Formulation 2 | Formulation 3 | Formulation 4 | Formulation 5 |
| --- | --- | --- | --- | --- | --- |
| Complexing agent | Sodium hydrogen carbonate | Ethanol | None | Methanol | None |
| Filler/diluent | Glucose | Mannitol; modified starch | Microcrystalline cellulose; lactose | Sodium chloride; dextrates | Glucose; sucrose |
| Granulating agent | None | *Acacia* mucilage | None | Starch mucilage | Tragacanth mucilage |
| Disintegrant | Alginic acid; carbon dioxide | Aluminum magnesium silicate | Crosscarmellose sodium | Microcrystalline cellulose | Sodium lauryl sulphate |
| Lubricant | Calcium stearate | Fumaric acid | Magnesium stearate | Liquid paraffin | Sodium benzoate |
| Glidant | Colloidal silica | Talc | Colloidal silica | Talc | Talc |
| Other ingredients | Dye | Dye | Dye; PVA-based film coating | PVA-based film coating | None |

In some embodiments, the complexing agent, filler, diluent, granulating agent, disintegrant, lubricant, or glidant is present in the amount per tablet indicated in Table 3.

TABLE 3

| Ingredient | Amount per tablet |
| --- | --- |
| Complexing agent | 1-200 mg |
| Filler/diluent | 100-200 mg |
| Granulating agent | 1-50 mg |
| Disintegrant | 1-50 mg |
| Lubricant | 1-10 mg |
| Glidant | 5-30 mg |

In some embodiments, the inclusion complex is formulated as a tablet comprising fulvestrant and a cyclodextrin in amounts per tablet as indicated in Table 4 and one or more additional ingredients listed in Table 4 in an amount per tablet as indicated in Table 4.

TABLE 4

| Ingredient | Amount Per Tablet |
| --- | --- |
| fulvestrant | 0.1 mg, 1 mg, 5 mg, 6 mg, 7 mg, 8 mg, 9 mg, 10 mg, 11 mg, 12 mg, 13 mg, 14 mg, 14 mg, 15 mg, 16 mg, 17 mg, 18 mg, 19 mg, 20 mg, 25 mg, 30 mg, 35 mg, 40 mg, 45 mg, 50 mg, 75 mg, 100 mg, 150 mg, 200 mg, 250 mg, 275 mg, 300 mg, 350 mg, 400 mg, 450 mg, 500 mg, 550 mg, 600 mg, 650 mg, 700 mg, 750 mg, or 800 mg |
| cyclodextrin | 150, 160, 170, 180, 190, 200, 210, 220, 230, 240, 250, 275, 300, 350, 400, 450, 500, 550, 600, 650, 700, 750, or 800 mg |
| Microcrystalline cellulose, glucose, mannitol, or sucrose | 150, 160, 165, 170, 180, 185, 190, 195, or 200 mg |
| Aluminum magnesium silicate, carmellose sodium, crosscarmellose, or modified starch | 5, 10, 15, 20, 25, 30, 35, 40, 45, 50, 55, or 60 mg |

TABLE 4-continued

| Ingredient | Amount Per Tablet |
| --- | --- |
| Colloidal silica or talc | 1, 2, 3, 4, 5, 6, 7, 8, 9, 10, 11, 12, 13, 14, 15, 16, 17, 18, 19, or 20 mg |
| Dextrates, lactose, or sodium chloride | 0.5, 1.0, 1.5, 2.0, 2.5, 3.0, 3.5, 4.0, 4.5, or 5.0 mg |
| Dye | 0.5, 1.0, 1.5, 2.0, 2.5, 3.0, 3.5, 4.0, 4.5, or 5.0 mg |
| Polymer-based film coating | 1, 2, 3, 4, 5, 6, 7, 8, 9, 10, 11, 12, 13, 14, 15, 16, 17, 18, 19, or 20 mg |

In some embodiments, are provided formulations of the inclusion complexes described herein comprising one or more of a vehicle, a suspending agent, antimicrobial preservatives, antioxidants, viscosity enhancing agents, sweetening agents, flavoring agents or coloring agents. The vehicle, suspending agent, antimicrobial preservatives, antioxidants, viscosity enhancing agents, sweetening agents, flavoring agents or coloring agents may be chosen from among the ingredients listed in Table 5. In some embodiments, formulations may contain zero, one, or more than one ingredient from each use category in Table 5. Formulations may additionally contain another vehicle, a suspending agent, antimicrobial preservatives, antioxidants, viscosity enhancing agents, sweetening agents, flavoring agents or coloring agents not listed in Table 5. Formulations may also contain additional ingredients that are not vehicles, suspending agents, antimicrobial preservatives, antioxidants, viscosity enhancing agents, sweetening agents, flavoring agents, or coloring agents. In some embodiments, the formulations described herein are oral formulations.

TABLE 5

| Use | Ingredients |
| --- | --- |
| Vehicle | Water, distilled water, purified water, water for injection, aromatic water, juices, syrups, spirits |
| Suspending agent | Agar, alginic acid, bentonite, calcium stearate, carbomers, carboxymethylcellulose calcium, carboxymethylcellulose sodium, carrageenan, cellulose, ceratonia, colloidal silicon dioxide, dextrin, gelatin, guar gum, hydroxyethyl cellulose, hydroxyethylmethyl cellulose, hydroxypropyl cellulose, hypromellose, kaolin, magnesium aluminum silicate, maltitol, medium-chain triglycerides, methylcellulose, microcrystalline cellulose, polycarbophil, polyethylene glycol, potassium alginate, povidone, propylene glycol alginate, sesame oil, sodium alginate, sodium starch glycolate, sorbitan esters, sucrose, tragacanth, xanthan gum. |
| Antimicrobial preservative | Alcohol, benzalkonium chloride, benzethonium chloride, benzoic acid, benzyl alcohol, boric acid, bronopol, butylated hydroxyanisole, butylparaben, cetrimide, cetylpyridinium chloride, chlorbutanol, chlorhexidine, chlorobutanol, chlorocresol, chloroform, chloroxylenol, cresol, dimethyl ether, ethylparaben, glycerin, hexetidine, imidurea, isopropyl alcohol, lactic acid, methylparaben, monothioglycerol, parabens, alkyl chain length, phenol, phenoxyethanol, phenylethyl alcohol, phenylmercuric acetate, phenylmercuric borate, phenylmercuric nitrate, potassium benzoate, potassium metabisulfite, potassium sorbate, propionic acid, propyl gallate, propylene glycol, propylparaben, sodium acetate, sodium benzoate, sodium borate, sodium lactate, sodium metabisulfite, sodium propionate, sodium sulfite, sorbic acid, thimerosal, xylitol. |
| Antioxidant | Ascorbyl palmitate, butylated hydroxyanisole, butylated hydroxytoluene, malic acid, propyl gallate, sodium bisulfite, sodium sulfite, sodium metabisulfite, potassium metabisulfite, potassium bisulfite, sodium thiosulfate, sodium formaldehyde sulfoxylate, L-ascorbic acid, D-ascorbic acid, acetylcysteine, cysteine, thioglycerol, thioglycoUic acid, thiolactic acid, thiourea, dithiothreitol, dithioerythreitol, glutathione, nordihydroguaiaretic acid, tocopherol, sodium ascorbate, hypophophorous acid, fumaric acid. |
| Viscosity enhancing agent | *Acacia*, agar, alginic acid, bentonite, carbomers, carboxymethylcellulose calcium, carboxymethylcellulose sodium, carrageenan, ceratonia, cetostearyl alcohol, chitosan, colloidal silicon dioxide, cyclomethicone, ethylcellulose, gelatin, glycerin, glyceryl behenate, guar gum, hectorite, hydrogenated vegetable oil type I, hydroxyethyl cellulose, hydroxyethylmethyl cellulose, hydroxypropyl cellulose, hydroxypropyl starch, hypromellose, magnesium aluminum silicate, maltodextrin, methylcellulose, polydextrose, polyethylene glycol, poly(methylvinyl ether/maleic anhydride), polyvinyl acetate phthalate, polyvinyl alcohol, potassium chloride, povidone, propylene glycol alginate, saponite, sodium alginate, sodium chloride, stearyl alcohol, sucrose, tragacanth, xanthan gum |
| Sweetening agent | Acesulfame potassium, alitame, aspartame, dextrose, erythritol, fructose, glycerin, inulin, isomalt, lactitol, glucose, maltitol, maltitol, maltose, mannitol, neohesperidin dihydrochalcone, polydextrose, saccharin, saccharin sodium, sodium cyclamate, sorbitol, sucralose, sucrose, syrups, honey, thaumatin, trehalose, xylitol. |

Exemplary formulations (e.g., oral formulation) are shown in Table 6.

TABLE 6

|  | Formulation 1 | Formulation 2 | Formulation 3 | Formulation 4 | Formulation 5 |
| --- | --- | --- | --- | --- | --- |
| Vehicle | Water for injection | Aromatic water | Syrup | Water for injection | Water for injection |
| Suspending agent | None | None | None | None | Microcrystalline cellulose |
| Antimicrobial preservative | None | Benzoic acid | Chloroform | Benzoic acid | Benzoic acid |
| Antioxidant | None | Thioglycerol | Acetyl cysteine | Thioglycerol | Ascorbic acid |
| Viscosity enhancing agent | None | None | None | None | Carboxymethyl cellulose |
| Sweetening agent | Aspartame | Acesulfame potassium | Fructose | Saccharin | Aspartame |
| Other ingredients | Flavouring & coloring agent | Flavouring & coloring agent | Flavouring & coloring agent | Flavouring & coloring agent | Flavouring & coloring agent |

In some embodiments, are provided formulations of the inclusion complexes described herein comprising one or more of a vehicle, suspending agents, antimicrobial preservatives, antioxidants, viscosity enhancing agents. The vehicle, suspending agents, antimicrobial preservatives, antioxidants, viscosity enhancing agents may be chosen from among the ingredients listed in Table 7. In some embodiments, formulations may contain zero, one, or more than one ingredient from each use category in Table 7. Formulations may additionally contain other vehicles, suspending agents, antimicrobial preservatives, antioxidants and viscosity enhancing agents not listed in Table 7. Formulations may also contain additional ingredients that are not vehicles, suspending agents, antimicrobial preservatives, antioxidants or viscosity enhancing agents. In some embodiments, the formulations described herein are intranasal formulations.

TABLE 7

| Use | Ingredients |
| --- | --- |
| Vehicle | Water, distilled water, purified water, water for injection, ethanol, buffers |
| Suspending agent | Alginic acid, bentonite, calcium stearate, carbomers, carboxymethylcellulose calcium, carboxymethylcellulose sodium, carrageenan, cellulose, ceratonia, colloidal silicon dioxide, dextrin, gelatin, guar gum, hydroxyethyl cellulose, hydroxyethylmethyl cellulose, hydroxypropyl cellulose, hypromellose, kaolin, magnesium aluminum silicate, maltitol, medium-chain triglycerides, methylcellulose, microcrystalline cellulose, polycarbophil, polyethylene glycol, potassium alginate, povidone, propylene glycol alginate, sesame oil, sodium alginate, sodium starch glycolate, sorbitan esters, sucrose, tragacanth, xanthan gum |
| Antimicrobial preservative | Alcohol, benzalkonium chloride, benzethonium chloride, benzoic acid, benzyl alcohol, boric acid, bronopol, butylated hydroxyanisole, butylparaben, cetrimide, cetylpyridinium chloride, chlorbutanol, chlorhexidine, chlorobutanol, chlorocresol, chloroform, chloroxylenol, cresol, dimethyl ether, ethylparaben, glycerin, hexetidine, imidurea, isopropyl alcohol, lactic acid, methylparaben, monothioglycerol, parabens, alkyl chain length, phenol, phenoxyethanol, phenylethyl alcohol, phenylmercuric acetate, phenylmercuric borate, phenylmercuric nitrate, potassium benzoate, potassium metabisulfite, potassium sorbate, propionic acid, propyl gallate, propylene glycol, propylparaben, sodium acetate, sodium benzoate, sodium borate, sodium lactate, sodium metabisulfite, sodium propionate, sodium sulfite, sorbic acid, thimerosal, xylitol |
| Antioxidant | Ascorbyl palmitate, butylated hydroxyanisole, butylated hydroxytoluene, malic acid, propyl gallate, sodium bisulfite, sodium sulfite, sodium metabisulfite, potassium metabisulfite, potassium bisulfite, sodium thiosulfate, sodium formaldehyde sulfoxylate, L-ascorbic acid, D-ascorbic acid, acetylcysteine, cysteine, thioglycerol, thioglycoUic acid, thiolactic acid, thiourea, dithiothreitol, dithioerythreitol, glutathione, nordihydroguaiaretic acid, tocopherol, sodium ascorbate, hypophophorous acid, fumaric acid |
| Viscosity enhancing agent | *Acacia*, agar, alginic acid, bentonite, carbomers, carboxymethylcellulose calcium, carboxymethylcellulose sodium, carrageenan, ceratonia, cetostearyl alcohol, chitosan, colloidal silicon dioxide, cyclomethicone, ethylcellulose, gelatin, glycerin, glyceryl behenate, guar gum, hectorite, hydrogenated vegetable oil type I, hydroxyethyl cellulose, hydroxyethylmethyl cellulose, hydroxypropyl cellulose, hydroxypropyl starch, hypromellose, magnesium aluminum silicate, maltodextrin, methylcellulose, polydextrose, polyethylene glycol, poly(methylvinyl ether/maleic anhydride), polyvinyl acetate phthalate, polyvinyl alcohol, potassium chloride, povidone, propylene glycol alginate, saponite, sodium alginate, sodium chloride, stearyl alcohol, sucrose, tragacanth, xanthan gum |

Exemplary formulations (e.g., intranasal formulation) are shown in Table 8.

TABLE 8

|  | Formulation 1 | Formulation 2 | Formulation 3 | Formulation 4 | Formulation 5 |
|---|---|---|---|---|---|
| Vehicle | Water for injection | Water for injection | Water for injection | pH 6 Buffered water for injection | Water for injection |
| Suspending agent | None | None | None | None | Microcrystalline cellulose |
| Antimicrobial preservative | None | Benzoic acid | Benzalkonium chloride | Benzoic acid | Benzoic acid |
| Antioxidant | None | Thioglycerol | Acetyl cysteine | Thioglycerol | Ascorbic acid |
| Viscosity enhancing agent | None | None | None | None | Carboxymethyl cellulose |
| Other ingredients | pH modifying agents | pH modifying agents | None | pH modifying agents | pH modifying agents |

Kits

Also provided are kits containing materials useful for the treatment of a condition that is responsive to fulvestrant (e.g., cancer or systemic lupus erythematosus). The kits may contain an inclusion complex of fulvestrant and a cyclodextrin, and optionally contain instructions for use (e.g., instructions for preparation and/or administration of a formulation comprising the complex). Information detailing possible side effects of the formulation, and any other relevant information may also be enclosed. The instructions may be in any suitable format, including, but not limited to, printed matter, videotape, computer readable disk, optical disc or directions to internet-based instructions.

In one aspect, is provided a kit for treating an individual who suffers from or is susceptible to one or more of the conditions described herein, comprising a first container comprising a dosage amount of a formulation containing an inclusion complex as disclosed herein, and instructions for use. The container may be any of those known in the art and appropriate for storage and delivery of intravenous, intranasal or oral formulations. In certain embodiments the kit further comprises a second container comprising a pharmaceutically acceptable carrier, diluent, adjuvant, etc. for preparation of the formulation to be administered to the individual.

In some embodiments, the kits comprise a container with a label. Suitable containers include, for example, bottles, vials, and test tubes. The containers may be formed from a variety of materials such as glass or plastic. The containers may hold an inclusion complex comprising fulvestrant and a cyclodextrin. In some embodiments, the containers may further comprise one or more additional pharmaceutical agents (e.g., an anti-cancer agent). The label on the container may indicate that the inclusion complex or the formulation is used for treating or suppressing a condition that is responsive to fulvestrant (e.g., cancer or systemic lupus erythematosus), and may also indicate directions for in vivo use, such as those described herein.

The kit may further include other materials desirable from a commercial and user standpoint, including other buffers, diluents, filters, needles, syringes, and package inserts with instructions for performing any methods described herein. In some embodiments, the kit comprises the container described above and a second container comprising a buffer.

The kits may include additional pharmaceutical agents for use in conjunction with the formulation described herein. In one aspect, the additional pharmaceutical agent is fulvestrant in uncomplexed form, such as in the product FASLODEX® (AstraZeneca Pharmaceuticals LP). In some variations, the additional pharmaceutical agent(s) may be one or more drug(s) for the treatment of conditions responsive to fulvestrant (e.g., cancer or systemic lupus erythematosus). In some variations, the additional pharmaceutical agent(s) may be one or more drug(s) for the treatment of one or more side effects from the use of the inclusion complexes described herein. These agents may be provided in a separate form, or mixed with the complexes described herein, provided such mixing does not reduce the effectiveness of either the pharmaceutical agent or formulation described herein and is compatible with the route of administration. Similarly the kits may include additional agents for adjunctive therapy or other agents known to the skilled artisan as effective in the treatment or prevention of the conditions described herein.

In some embodiments, the additional pharmaceutical agent is an anti-cancer agent. In some embodiments, the anti-cancer agent is an aromatase inhibitor (AI), including, but not limited to, anastrozole (e.g., ARIMIDEX®), letrozole (e.g., FEMARA®), exemestane (e.g., AROMASIN®), aminoglutethimide (Cytadren®), vorozole (e.g., RIVIZOR®), formestane (e.g., LENTARON®), fadrozole (e.g., AFEMA®), or testolactone (e.g., TESLAC®). In some embodiments, the anti-cancer agent is an epidermal growth factor receptor (EGFR) inhibitor, including, but not limited to, gefitinib (e.g., IRESSA®), trastuzumab (e.g., HERCEPTIN®), or erlotinib (e.g., TARCEVA®). In some embodiments, the anti-cancer agent is a farnesyl transferase inhibitor, including, but not limited to tipifarnib (e.g., ZARNESTRA®). In some embodiments, the anti-cancer agent is uncomplexed fulvestrant, such as uncomplexed fulvestrant administered as an intramuscular injection (e.g., FASLODEX®). In some embodiments, the anti-cancer agent is an antioxidant, including, but not limited to vitamin E, vitamin C, beta-carotene, and selenium.

In some embodiments, the anti-cancer agent is selected from the group consisting of anastrozole (e.g., ARIMIDEX®), letrozole (e.g., FEMARA®), exemestane (e.g., AROMASIN®), aminoglutethimide (e.g., Cytadren®), vorozole (e.g., RIVIZOR®), formestane (e.g., LENTARON®), fadrozole (e.g., AFEMA®), testolactone (e.g., TESLAC®), gefitinib (e.g., IRESSA®), trastuzumab (e.g., HERCEPTIN®), erlotinib (e.g., TARCEVA®), tipifarnib (e.g., ZARNESTRA®), uncomplexed fulvestrant (e.g., FASLODEX®), and an antioxidant (e.g., vitamin E, vitamin C, beta-carotene, and selenium).

Kits may also be provided that contain sufficient dosages of the compounds described herein (including formulations thereof) to provide effective treatment for an individual, such as a human in need of such treatment, for an extended period, such as any of 1-3 days, 1-5 days, a week, 2 weeks, 3, weeks, 4 weeks, 6 weeks, 8 we 3 months, 4 months, 5 months, 6 months, 7 months, 8 months, 9 months or more.

The kits may include the composition as described herein packaged in either a unit dosage form or in a multi-use form. The kits may also include multiple units of the unit dose form. The kits may be used for any of the methods described herein, including, for example, to treat an individual with a condition described herein, or to delay a condition described herein. In certain embodiments the kits may include a dosage amount of at least one formulation as disclosed herein. Kits may also comprise a means for the delivery of the formulation thereof, such as a syringe, inhaler, intranasal spray, patch or other such device.

Methods of Use

The inclusion complexes described herein comprising fulvestrant and a cyclodextrin, formulations thereof, and formulations comprising an uncomplexed fulvestrant and a cyclodextrin, or mixtures thereof, may be used for the treatment of indications that are believed to be or are responsive to fulvestrant therapy (e.g., cancer and systemic lupus erythematosus). In some embodiments, provided is a method of treating a cancer in an individual in need thereof comprising administering to the individual an effective amount of an inclusion complex comprising fulvestrant and a cyclodextrin, or a formulation thereof.

For purposes herein, beneficial or desired results in a treatment include, but are not limited to, one or more of the following: decreasing one or more symptoms resulting from the condition (e.g., cancer or systemic lupus erythematosus), diminishing the extent of the disease, stabilizing the condition, delaying or slowing the progression of the condition, reversing the progression or severity of the condition, ameliorating the condition, decreasing the dose of one or more other medications required to treat the condition, and/or increasing the quality of life of an individual who has been or is suspected of having the condition. The methods described herein contemplate any one or more of these aspects of treatment. In one aspect, a method of delaying the development of a condition is provided, wherein the method reduces the probability of developing the condition in a given time frame and/or reduces the extent of the condition in a given time frame, when compared to not using the method. Such comparisons may be based on clinical studies, using a statistically significant number of subjects. In a particular aspect, a method of delaying the development of a condition is provided, wherein the method encompasses preventing a recurrence of the condition in a given time frame, such as 3 months, 6 months, 1 year, 2 years, 3 years, 5 years, 10 years or more.

In some embodiments, the methods and/or inclusion complex formulations used herein reduce the severity of one or more symptoms associated with the condition (e.g., cancer or systemic lupus erythematosus) by at least any of about 10%, 20%, 30%, 40%, 50%, 60%, 70%, 80%, 90%, 95%, or 100% compared to the corresponding symptom in the same individual prior to treatment or compared to the corresponding symptom in other individuals not receiving the methods and/or inclusion complex formulations.

In some variations, the individual being treated for a condition described herein (e.g., cancer or systemic lupus erythematosus) has been identified as having one or more of the symptoms described herein. Identification of the conditions as described herein by a skilled physician is routine in the art such as routine physical exams or clinical detection.

In some embodiments of a method directed to cancer, the cancer is early stage cancer, non-metastatic cancer, primary cancer, advanced cancer, locally advanced cancer, metastatic cancer, cancer in remission, recurrent cancer, cancer in an adjuvant setting, cancer in a neoadjuvant setting, or cancer substantially refractory to hormone therapy. In some embodiments, the cancer includes, but is not limited to, breast cancer, endometrial cancer, prostate cancer, and lung cancer.

The methods detailed herein may be applicable to an individual in need thereof, which may be an individual who has been diagnosed with, previously treated for, and/or suspected of having the condition to be treated (e.g., cancer or systemic lupus erythematosus). With respect to prevention, the individual in need thereof may also be an individual who is at risk for a condition (e.g., age, a family or self history of the condition, life-style factors indicative of risk for the condition, etc.). In a particular variation, an individual is an individual who has previously had the condition and is at risk for recurrence of the condition.

In some embodiments, the individual is a mammal, including, but not limited to human, bovine, horse, feline, rabbit, canine, rodent, or primate. In some embodiments, the mammal is a primate. In some embodiments, the primate is a human. In some embodiments, the individual is human, including adults and children. The human may be of either sex and the methods may be applicable to either a man or a woman. In one aspect, the individual is a human who is believed to be or is in need of treatment. In some embodiments, the individual is a pre-menopausal, per-menopausal or post-menopausal woman. In some embodiments, the individual is a post-menopausal woman with disease (e.g., breast cancer) progression following hormone (e.g., antiestrogen) therapy. In some embodiments, the individual is a pre-menopausal woman with disease (e.g., breast cancer) progression following hormone (e.g., anti-estrogen) therapy. In some embodiments, the individual is a non-mammal. In some variations, the primate is a non-human primate such as chimpanzees and other apes and monkey species. In some embodiments, the mammal is a farm animal such as cattle, horses, sheep, goats, and swine; pets such as rabbits, dogs, and cats; laboratory animals including rodents, such as rats, mice, and guinea pigs; and the like. In some embodiments, the individual is a non-mammal, including, but not limited to, birds, and the like. The term "individual" does not denote a particular age or sex.

In some embodiments, provided is a method of treating breast cancer in an individual in need thereof, comprising administering to the individual an effective amount of an inclusion complex comprising fulvestrant and a cyclodextrin (e.g., MBCD or HPBCD), or a formulation thereof. In some embodiments, the individual is a pre- or peri-menopausal individual with breast cancer progression following anti-estrogen therapy. In some embodiments, the individual is a post-menopausal individual with breast cancer progression following anti-estrogen therapy. In some embodiments, the breast cancer is early stage breast cancer, non-metastatic breast cancer, advanced breast cancer, stage IV breast cancer, locally advanced breast cancer, metastatic breast cancer, hormone receptor positive metastatic breast cancer, advanced breast cancer, breast cancer in remission, breast cancer in an adjuvant setting, ductal carcinoma in situ (DCIS), invasive ductal carcinoma (IDC), or breast cancer in a neoadjuvant setting. In some specific embodiments, the breast cancer is hormone receptor positive metastatic breast cancer. In some embodiments, the breast cancer is advanced breast cancer. In some embodiments, the breast cancer is ductal carcinoma in situ. In some embodiments, there are provided methods of treating breast cancer (which may be HER2 positive or HER2 negative), including, for example, advanced breast cancer, stage IV breast cancer, locally advanced breast cancer, and metastatic breast cancer. In some embodiments, the individual may be a human who has a gene, genetic mutation, or polymorphism associated with breast cancer (e.g., BRCA1, BRCA2, ATM, CHEK2, RAD51, AR, DIRAS3, ERBB2, TP53, AKT, PTEN, and/or PI3K) or has one or more extra copies of a gene (e.g., one or more extra copies of the HER2 gene) associated with breast cancer. In some embodiments, the method further comprises identifying a cancer patient population (e.g., breast cancer population) based on a hormone receptor status of patients having tumor tissue not expressing both ER and PgR and administering to the patient population an effective amount of the inclusion complex comprising fulvestrant and a cyclodextrin.

In some embodiments, provided is a method of treating endometrial cancer (or uterine cancer) in an individual in need thereof, comprising administering to the individual an effective amount of an inclusion complex comprising fulvestrant and a cyclodextrin (e.g., MBCD or HPBCD), or a formulation thereof. In some embodiments, the individual is a pro- or peri-menopausal woman. In some embodiments, the individual is a post-menopausal woman. In some embodiments, the endometrial cancer is endometrial stromal sarcoma, uterine carcinosarcoma, endometrial adenocarcinoma, Type I endometrial carcinoma, or Type II endometrial carcinoma. In some embodiments, the endometrial carcinoma is stage IA, stage IB, stage IC, stage IIA, stage IIB, stage IIIA, stage IIIB, stage IIIC, stage IVA, or stage IVB endometrial carcinoma.

In some embodiments, provided is a method of treating prostate cancer in an individual in need thereof, comprising administering to the individual an effective amount of an inclusion complex comprising fulvestrant and a cyclodextrin (e.g., MBCD or HPBCD), or a formulation thereof. In some embodiments, the prostate cancer is an adenocarcinoma. In some embodiments, the prostate cancer is a sarcoma, neuroendocrine tumor, small cell cancer, ductal cancer, or a lymphoma. There are provided methods of treating prostate cancer at any of the four stages, A, B, C, or D, according to the Jewett staging system. In some embodiments, the prostate cancer is stage A prostate cancer (the cancer cannot be felt during a rectal exam.). In some embodiments, the prostate cancer is stage B prostate cancer (the tumor involves more tissue within the prostate, it can be felt during a rectal exam, or it is found with a biopsy that is done because of a high PSA level.). In some embodiments, the prostate cancer is stage C prostate cancer (the cancer has spread outside the prostate to nearby tissues.). In some embodiments, the prostate cancer is stage D prostate cancer. In some embodiments, the prostate cancer may be androgen independent prostate cancer (AIPC). In some embodiments, the prostate cancer may be androgen dependent prostate cancer. In some embodiments, the prostate cancer may be refractory to hormone therapy. In some embodiments, the prostate cancer may be substantially refractory to hormone therapy. In some embodiments, the individual may be a human who has a gene, genetic mutation, or polymorphism associated with prostate cancer (e.g., RNASEL/HPC1, ELAC2/HPC2, SR-A/MSR1, CHEK2, BRCA2, PON1, OGG1, MIC-1, TLR4, and/orPTEN) or has one or more extra copies of a gene associated with prostate cancer.

In some embodiments, provided is a method of treating lung cancer in an individual in need thereof, comprising administering to the individual an effective amount of an inclusion complex comprising fulvestrant and a cyclodextrin (e.g., MBCD or HPBCD), or a formulation thereof. In some embodiments, the lung cancer is a non-small cell lung cancer (NSCLC). Examples of NSCLC include, but are not limited to, large-cell carcinoma (e.g., large-cell neuroendocrine carcinoma, combined large-cell neuroendocrine carcinoma, basaloid carcinoma, lymphoepithelioma-like carcinoma, clear cell carcinoma, and large-cell carcinoma with rhabdoid phenotype), adenocarcinoma (e.g., acinar, papillary (e.g., bronchioloalveolar carcinoma, nonmucinous, mucinous, mixed mucinous and nonmucinous and indeterminate cell type), solid adenocarcinoma with mucin, adenocarcinoma with mixed subtypes, well-differentiated fetal adenocarcinoma, mucinous (colloid) adenocarcinoma, mucinous cystadenocarcinoma, signet ring adenocarcinoma, and clear cell adenocarcinoma), neuroendocrine lung tumors, and squamous cell carcinoma (e.g., papillary, clear cell, small cell, and basaloid). In some embodiments, the NSCLC may be, according to TNM classifications, a stage T tumor (primary tumor), a stage N tumor (regional lymph nodes), or a stage M tumor (distant metastasis). In some embodiments, the lung cancer is a carcinoid (typical or atypical), adenosquamous carcinoma, cylindroma, or carcinoma of the salivary gland (e.g., adenoid cystic carcinoma or mucoepidermoid carcinoma). In some embodiments, the lung cancer is a carcinoma with pleomorphic, sarcomatoid, or sarcomatous elements (e.g., carcinomas with spindle and/or giant cells, spindle cell carcinoma, giant cell carcinoma, carcinosarcoma, or pulmonary blastoma). In some embodiments, the cancer is small cell lung cancer (SCLC; also called oat cell carcinoma). The small cell lung cancer may be limited-stage, extensive stage or recurrent small cell lung cancer. In some embodiments, the individual may be a human who has a gene, genetic mutation, or polymorphism suspected or shown to be associated with lung cancer (e.g., SASH1, LATS1, IGF2R, PARK2, KRAS, PTEN, Kras2, Krag, Pas1, ERCC1, XPD, IL8RA, EGFR, a,AD, EPHX, MMP1, MMP2, MMP3, MMP12, ILlp\RAS, and/or AKT) or has one or more extra copies of a gene associated with lung cancer.

In another aspect, the inclusion complexes described herein (e.g., an inclusion complex comprising fulvestrant and a cyclodextrin) may be used for the treatment of systemic lupus erythematosus. In some embodiments is provided a method of treating systemic lupus erythematosus in an individual, comprising administering to the individual an effective amount of an inclusion complex comprising fulvestrant and a cyclodextrin, or a formulation thereof.

The method detailed herein may use any inclusion complex or composition detailed herein. As described below, the inclusion complex may be administered via any route (e.g., orally, intranasally, sublingually, parenterally, such as intravenously, rectally, intravaginally).

In another aspect, provided is a method of treating a cancer in an individual in need thereof; comprising administering to the individual an effective amount of an inclusion complex comprising fulvestrant and a cyclodextrin, or a formulation thereof, and one other pharmaceutical agent.

In another aspect, provided is a method of treating systemic lupus erythematosus in an individual in need thereof, comprising administering to the individual an effective amount of an inclusion complex comprising fulvestrant and a cyclodextrin, or a formulation thereof, and one other pharmaceutical agent.

In the context of an inclusion complex of fulvestrant, the additional pharmaceutical agent in one aspect refers to an active agent other than complexed fulvestrant, for example, an anti-cancer agent other than fulvestrant, which is administered to elicit a therapeutic effect or fulvestrant in an uncomplexed form. In one aspect, the additional pharmaceutical agent is an anti-cancer agent other than fulvestrant. More than one additional pharmaceutical agent may be employed. An additional pharmaceutical agent may be directed to a therapeutic effect related to one or more conditions that fulvestrant is intended to treat or prevent (e.g., cancer or systemic lupus erythematosus) or the pharmaceutical agent may be intended to treat or prevent a symptom of the underlying condition (e.g., pain, swelling, warmth and redness throughout the breast, Paget's disease of the breast, malar rash, fatigue, loss of appetite, inflammation (e.g., pericarditis, myocarditis, or endocarditis), bone or joint pain, arthritis, anemia and iron deficiency, pleuritis, pleural effusion, lupus pneumonitis, pulmonary hypertension, pulmonary emboli, pulmonary hemorrhage, chronic diffuse interstitial lung disease, hematuria, headache, or proteinuria, etc.) or to further reduce the appearance or severity of side effects of fulvestrant (e.g., asthenia, pain, headache, back pain, vasodilatation, nausea, vomiting, constipation, anemia, bone pain, arthritis, dizziness, insomnia, rash, or urinary tract infection).

In some embodiments, the pharmaceutical agent is an anti-cancer agent. In some embodiments, the anti-cancer agent is an aromatase inhibitor (AI), including, but not limited to, anastrozole (e.g., ARIMIDEX®), letrozole (e.g., FEMARA®), exemestane (e.g., AROMASIN®), aminoglutethimide (Cytadrene®), vorozole (e.g., RIVIZOR®), formestane (e.g., LENTARON®), fadrozole (e.g., AFEMA®), or testolactone (e.g., TESLAC®). In some embodiments, the anti-cancer agent is an epidermal growth factor receptor (EGFR) inhibitor, including, but not limited to, gefitinib (e.g., IRESSA®), trastuzumab (e.g., HERCEPTIN®), or erlotinib (e.g., TARCEVA®). In some embodiments, the anti-cancer agent is a farnesyl transferase inhibitor, including, but not limited to tipifarnib (e.g., ZARNESTRA®). In some embodiments, the anti-cancer agent is fulvestrant in uncomplexed form (e.g., FASLODEX®). In some embodiments, the anti-cancer agent is an antioxidant, including, but not limited to vitamin E, vitamin C, beta-carotene, and selenium. In some embodiments, the formulation may include combinations of two or more of the anti-cancer agents as described herein (e.g., any of 2, 3, or more anti-cancer agents).

In some embodiments, the antioxidant includes, but is not limited to, ascorbyl palmitate, butylated hydroxyanisole, butylated hydroxytoluene, malic acid, propyl gallate, sodium bisulfite, sodium sulfite, sodium metabisulfite, potassium metabisulfite, potassium bisulfite, sodium thiosulfate, sodium formaldehyde sulfoxylate, L-ascorbic acid, D-ascorbic acid, acetylcysteine, cysteine, thioglycerol, thioglycoUic acid, thiolactic acid, thiourea, dithiothreitol, dithioerythritol, glutathione, nordihydroguaiaretic acid, tocopherol, sodium ascorbate, hypophosphorous acid, and fumaric acid.

In some embodiments, the anti-cancer agent is selected from the group consisting of anastrozole (e.g., ARIMIDEX®), letrozole (e.g., FEMARA®), exemestane (e.g., AROMASIN®), aminoglutethimide (Cytadren®), vorozole (e.g., RIVIZOR®), formestane (e.g., LENTARON®), fadrozole (e.g., AFEMA®), testolactone (e.g., TESLAC®), gefitinib (e.g., IRESSA®), trastuzumab (e.g., HERCEPTIN®), erlotinib (e.g., TARCEVA®), tipifarnib (e.g., ZARNESTRA®), fulvestrant in uncomplexed form (e.g., FASLODEX®), and an antioxidant (e.g., vitamin E, vitamin C, beta-carotene, and selenium).

In some embodiments, provided is a method of treating a hormone receptor positive metastatic breast cancer in an individual in need thereof, comprising administering to the individual an effective amount of an inclusion complex comprising fulvestrant and a cyclodextrin, or a formulation thereof and anastrozole.

In some embodiments, provided is a method of treating a hormone receptor positive metastatic breast cancer in an individual in need thereof, comprising administering to the individual an effective amount of an inclusion complex comprising fulvestrant and a cyclodextrin, or a formulation thereof, and exemestane.

In some embodiments, provided is a method of treating a hormone receptor positive metastatic breast cancer in an individual in need thereof, comprising administering to the individual an effective amount of an inclusion complex comprising fulvestrant and a cyclodextrin, or a formulation thereof, and uncomplexed fulvestrant (e.g., FASLODEX®).

In some embodiments, provided is a method of treating a hormone receptor positive metastatic breast cancer in an individual in need thereof, comprising administering to the individual an effective amount of an inclusion complex comprising fulvestrant and a cyclodextrin, or a formulation thereof, and gefitinib.

In some embodiments, provided is a method of treating a hormone receptor positive metastatic breast cancer in an individual in need thereof, comprising administering to the individual an effective amount of an inclusion complex comprising fulvestrant and a cyclodextrin, or a formulation thereof, and lapatinib.

In some embodiments, provided is a method of treating a hormone receptor positive metastatic breast cancer in an individual in need thereof, comprising administering to the individual an effective amount of an inclusion complex comprising fulvestrant and a cyclodextrin, or a formulation thereof, and tipifarnib.

In some embodiments, the inclusion complex comprising fulvestrant and a cyclodextrin, or a formulation thereof, and the other pharmaceutical agent are administered simultaneously. In some embodiments, the inclusion complex comprising fulvestrant and a cyclodextrin, or a formulation thereof, and the other pharmaceutical agent are administered sequentially. Either the inclusion complex or the other pharmaceutical agent may be administered first. The inclusion complex and the other pharmaceutical agent may be contained in the same or different packages or compositions.

Dosing and Methods of Administration

The amount of the inclusion complex administered to an individual (such as a human) and/or the amount administered in order to achieve an effective amount may vary based on a variety of factors, including, for example, the particular condition being treated, the frequency of administration, the particular formulation being administered, the severity of the condition being treated and the age, weight and general health of the individual, the adverse effects experienced by the individual being treated, etc. A pharmaceutical unit dosage chosen may be fabricated and administered to provide a defined final concentration of drug in the blood, tissues, organs, or other targeted region of the body. Determination of an effective amount for a given situation can be readily determined by routine experimentation (e.g., using in vivo animal models) and is within the skill and judgment of the ordinary clinician, particularly in view of the teachings provided herein.

In various embodiments, an effective amount of the inclusion complex or therapy may do any one or more of the following: (i) reduce the number of cancer cells; (ii) reduce tumor size; (iii) inhibit, retard, slow to some extent, and preferably stop cancer cell infiltration into peripheral organs; (iv) inhibit (e.g., slow to some extent and preferably stop) tumor metastasis; (v) inhibit tumor growth; (vi) prevent or delay occurrence and/or recurrence of a tumor, and (vii) relieve to some extent one or more of the symptoms associated with the cancer. In various embodiments, the amount is sufficient to ameliorate, palliate, lessen, and/or delay one or more of symptoms of cancer. In various embodiments, an effective amount of the inclusion complex or therapy may inhibit, retard, slow to some extent, prevent, delay occurrence and/or recurrence of; or relieve to some extent one or more of the symptoms associated with systemic lupus erythematosus.

The effective amount may vary depending on the composition being administered, the condition being treated/prevented, the severity of the condition being treated/prevented, the age, body size, weight, and relative health of the individual, the route and form of administration, the judgement of the attending medical or veterinary practitioner (if applicable), and other factors appreciated by the skilled artisan in view of the teaching provided herein. An effective amount may be assessed, for example, by using data from one or more clinical, physiological, biochemical, histological, electrophysiological, and/or behavioral evaluations.

In some embodiments, the amount of the inclusion complex comprising fulvestrant and a cyclodextrin is effective to result in an objective response (such as a partial response or a complete response). In some embodiments, the amount of inclusion complex is sufficient to result in a complete response in the individual. In some embodiments, the amount of the inclusion complex is sufficient to result in a partial response in the individual. In some embodiments, the amount of the inclusion complex administered alone is sufficient to produce an overall response rate of more than about any of about 10%, 20%, 30%, 40%, 50%, 60%, 70%, 80%, 90%, or 95% among a population of individuals treated with the complex. Responses of an individual to treatment can be determined by the skilled artisan using, for example, routine physical exams and/or clinical detection known in the art and/or described herein.

In some embodiments, the amount of the inclusion complex is below the level that induces a toxicological effect (where the toxicological effect in one aspect is an effect above a clinically acceptable level of toxicity) or is at a level where a potential side effect can be controlled or tolerated when the complex is administered to the individual. In some embodiments, the amount of the inclusion complex is close to a maximum tolerated dose (MTD) of the complex following the same dosing regime. In some embodiments, the amount of the inclusion complex is more than any of about 80%, 90%, 95%, or 98% of the MTD.

In some embodiments, the amount of fulvestrant from an inclusion complex comprising fulvestrant and a cyclodextrin is included in any of the following ranges: about 0.1 to about 5 mg, about 1 to about 10 mg, about 5 to about 10 mg, about 10 to about 15 mg, about 15 to about 20 mg, about 20 to about 25 mg, about 20 to about 50 mg, about 25 to about 50 mg, about 50 to about 75 mg, about 50 to about 100 mg, about 75 to about 100 mg, about 100 to about 125 mg, about 125 to about 150 mg, about 150 to about 175 mg, about 175 to about 200 mg, about 200 to about 225 mg, about 225 to about 250 mg, about 250 to about 300 mg, about 300 to about 350 mg, about 350 to about 400 mg, about 400 to about 450 mg, about 450 to about 500 mg, about 550 to about 600 mg, about 650 to about 700 mg, or about 750 to about 800 mg. In some embodiments, the amount of fulvestrant from an inclusion complex is in the range of about 1 mg to about 800 mg, such as about 5 mg to about 700 mg, 10 mg to about 500 mg, 20 mg to about 250 mg, or about 25 mg, 50 mg, 75 mg, 100 mg, 125 mg, 150 mg, 175 mg, 200 mg, 250 mg, 300 mg, 350 mg, 400 mg, 500 mg, 600 mg, 700 mg, or 800 mg. In some embodiments of the liquid formulations, the concentration of fulvestrant from an inclusion complex comprising fulvestrant and cyclodextrin as inclusion complex is dilute (about 0.1 mg/ml) or concentrated (about 200 mg/ml), including for example any of about 0.1 to about 200 mg/ml, about 0.1 to about 100 mg/ml, about 1 to about 50 mg/ml, about 2 mg/ml to about 25 mg/ml, about 4 to about 10 mg/ml, about 5 mg/ml. In some embodiments, the concentration of fulvestrant of the inclusion complex is at least about any of 0.5 mg/ml, 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, 50 mg/ml, 60 mg/ml, 70 mg/ml, 80 mg/ml, 90 mg/ml, 100 mg/ml, 150 mg/ml, or 200 mg/ml.

Exemplary effective amounts of fulvestrant from an inclusion complex comprising fulvestrant and a cyclodextrin include, but are not limited to, any of about 2.5 mg/m$^2$, 5 mg/m$^2$, 10 mg/m$^2$, 15 mg/m$^2$, 20 mg/m$^2$, 25 mg/m$^2$, 30 mg/m$^2$, 50 mg/m$^2$, 60 mg/m$^2$, 75 mg/m$^2$, 80 mg/m$^2$, 90 mg/m$^2$, 100 mg/m$^2$, 120 mg/m$^2$, 160 mg/m$^2$, 175 mg/m$^2$, 180 mg/m$^2$, 200 mg/m$^2$, 210 mg/m$^2$, 220 mg/m$^2$, 250 mg/m$^2$, 260 mg/m$^2$, 300 mg/m$^2$, 350 mg/m$^2$, 400 mg/m$^2$, 500 mg/m$^2$, 540 mg/m$^2$, 750 mg/m$^2$, 1000 mg/m$^2$, or 1080 mg/m$^2$. In various variations, a formulation includes less than about any of 350 mg/m$^2$, 300 mg/m$^2$, 250 mg/m$^2$, 200 mg/m$^2$, 150 mg/m$^2$, 120 mg/m$^2$, 100 mg/m$^2$, 90 mg/m$^2$, 50 mg/m$^2$, or 30 mg/m$^2$ of fulvestrant. In some embodiments, the amount of fulvestrant within the inclusion complex per administration is less than any of about 25 mg/m$^2$, 22 mg/m$^2$, 20 mg/m$^2$, 18 mg/m$^2$, 15 mg/m$^2$, 14 mg/m$^2$, 13 mg/m$^2$, 12 mg/m$^2$, 11 mg/m$^2$, 10 mg/m$^2$, 9 mg/m$^2$, 8 mg/m$^2$, 7 mg/m$^2$, 6 mg/m$^2$, 5 mg/m$^2$, 4 mg/m$^2$, 3 mg/m$^2$, 2 mg/m$^2$, or 1 mg/m. In some embodiments, the effective amount of fulvestrant from the inclusion complex is included in any of the following ranges: about 1 to about 5 mg/m, about 5 to about 10 mg/m$^2$, about 10 to about 25 mg/m$^2$, about 25 to about 50 mg/m$^2$, about 50 to about 75 mg/m$^2$, about 75 to about 100 mg/m$^2$, about 100 to about 125 mg/m$^2$, about 125 to about 150 mg/m$^2$, about 150 to about 175 mg/m$^2$, about 175 to about 200 mg/m$^2$, about 200 to about 225 mg/m$^2$, about 225 to about 250 mg/m$^2$, about 250 to about 300 mg/m$^2$, about 300 to about 350 mg/m$^2$, or about 350 to about 400 mg/m$^2$.

In some embodiments of any of the above aspects, the effective amount of fulvestrant from an inclusion complex comprising fulvestrant and a cyclodextrin includes at least any of about 0.01 mg/kg, 0.05 mg/kg, 0.1 mg/kg, 0.25 mg/kg, 0.5 mg/kg, 1 mg/kg, 1.5 mg/kg, 2 mg/kg, 2.5 mg/kg, 3.5 mg/kg, 5 mg/kg, 6.5 mg/kg, 7.5 mg/kg, 10 mg/kg, 15 mg/kg, or 20 mg/kg. In various variations, the effective amount of fulvestrant includes less than any of about 350 mg/kg, 300 mg/kg, 250 mg/kg, 200 mg/kg, 150 mg/kg, 100 mg/kg, 50 mg/kg, 25 mg/kg, 20 mg/kg, 10 mg/kg, 7.5 mg/kg, 6.5 mg/kg, 5 mg/kg, 3.5 mg/kg, 2.5 mg/kg, 2 mg/kg, 1.5 mg/kg, 1 mg/kg, 0.75 mg/kg, 0.5 mg/kg, 0.25 mg/kg, 0.1 mg/kg, 0.05 mg/kg.

Exemplary dosing frequencies include, but are not limited to, weekly without break; weekly, three out of four weeks; once every three weeks; once every two weeks; weekly, two out of three weeks. In some embodiments, the inclusion complex is administered any of about once every 2 weeks, once every 3 weeks, once every 4 weeks, once every 6 weeks, or once every 8 weeks. In some embodiments, the composition is administered at least any of about 1×, 2×, 3×, 4×, 5×, 6×, or 7× (i.e., daily) a week. In some embodiments, the intervals between each administration are less than any of about 6 months, 3 months, 1 month, 20 days, 15, days, 12 days, 10 days, 9 days, 8 days, 7 days, 6 days, 5 days, 4 days, 3 days, 2 days, or 1 day. In some embodiments, the intervals between each administration are more than any of about 1 month, 2 months, 3 months, 4 months, 5 months, 6 months, 8 months, or 12 months. In some embodiments, there is no break in the dosing schedule. In some embodiments, the interval between each administration is no more than about a week. The administration of the inclusion complex can be extended over an extended period of time, such as from about a month up to about seven years. In some embodiments, the composition is administered over a period of at least any of about 2, 3, 4, 5, 6, 7, 8, 9, 10, 11, 12, 18, 24, 30, 36, 48, 60, 72, or 84 months. The dosing frequency of the inclusion complex may be adjusted over the course of the treatment based on the judgment of the administering physician. For example, a multiple daily dosage routine of the inclusion complex may be included.

The inclusion complexes described herein allow, in some embodiments, infusion of the complex to an individual over an infusion time that is shorter than about 24 hours. For example, in some embodiments, the inclusion complex is administered over an infusion period of less than any of about 24 hours, 12 hours, 8 hours, 5 hours, 3 hours, 2 hours, 1 hour, 30 minutes, 20 minutes, or 10 minutes. In some embodiments, the inclusion complex is administered over an infusion period of about 30 minutes.

Any of the inclusion complexes described herein (e.g., an inclusion complex comprising fulvestrant and a cyclodextrin) can be administered to an individual (such as human) via various routes, including, for example, intravenous, intra-arterial, intraperitoneal, intrapulmonary, oral, inhalation, intravesicular, intramuscular, intra-tracheal, subcutaneous, intraocular, intrathecal, transmucosal, intranasal, rectal, intravaginal and transdermal. In some embodiments, sustained continuous release formulation of the composition may be used. In one variation, inclusion complex is administered by any acceptable route including, but not limited to, orally, intramuscularly, transdermally, intravenously, intranasally, rectally, intravaginally through an inhaler or other air borne delivery systems and the like. Additional methods of administration are known in the art.

In some embodiments, the inclusion complexes described herein (e.g., an inclusion complex comprising fulvestrant cyclodextrin) are administered parenterally (e.g., intravenously). For example, in some embodiments are provided methods of treating a cancer in an individual (e.g., an adult) comprising intranasally administering an inclusion complex comprising fulvestrant and a cyclodextrin.

The physiochemical properties of the inclusion complexes described herein (e.g., an inclusion complex comprising fulvestrant and a cyclodextrin) may allow the complexes to be taken orally or sublingually. In some embodiments, the inclusion complexes or formulations comprising the complexes are suitable for oral or sublingual administration.

As described herein, the inclusion complexes may be administered with an additional therapeutic agent and/or an additional treatment modality. The dosing frequency of the inclusion complex and the additional pharmaceutical agent may be adjusted over the course of the treatment based on the judgment of the administering physician. When administered separately, the inclusion complex and the additional therapeutic agent can be administered at different dosing frequency or intervals. For example, the inclusion complex can be administered weekly, while the additional therapeutic agent can be administered more or less frequently. In some embodiments, sustained continuous release formulation of the inclusion complex and/or the additional therapeutic agent may be used. Various formulations and devices for achieving sustained release are known in the art. A combination of the administration configurations described herein can be used.

In some embodiments, the inclusion complex (e.g., the inclusion complex comprising fulvestrant and a cyclodextrin) can be administered daily and the additional therapeutic agent (e.g., FASLODEX®) can be administered monthly. In some embodiments, the inclusion complex (e.g., the inclusion complex comprising fulvestrant and a cyclodextrin) can be administered weekly and the additional therapeutic agent (e.g., FASLODEX®) can be administered monthly.

In some embodiments of any of the aspects of the inventions provided herein, the cyclodextrin is hydroxypropyl beta-cyclodextrin (HPBCD) or methyl beta-cyclodextrin (MBCD). In some embodiments, the cyclodextrin is hydroxypropyl beta-cyclodextrin (HPBCD) or methyl beta-cyclodextrin (MBCD), wherein HPBCD or MBCD is used in a formulation for intravascular administration. In some embodiments, the cyclodextrin is hydroxypropyl beta-cyclodextrin (HPBCD) or methyl beta-cyclodextrin (MBCD), wherein HPBCD or MBCD is used in a formulation for slow intravascular administration.

The commercial product (e.g., FASLODEX®) is to be stored under refrigerated conditions (2-8° C.), whilst the inventor has found that excellent stability at room temperature may be attained by the inclusion complex of the present invention: an inclusion complex of the invention has been found to be stable at temperatures of over 25° C. and at 40° C. for over 24 months.

The present invention will be understood more readily by reference to the following examples, which are provided by way of illustration and are not intended to be limiting of the present invention.

EXAMPLES

It is understood that the examples and embodiments described herein are for illustrative purposes only and that various modifications or changes in light thereof will be suggested to persons skilled in the art and are to be included within the spirit and purview of this application.

The fulvestrant used in the Examples was obtained from Hangzhou Hysen Pharma Co., Ltd., Hangzhou, China.

Example 1

Evaluation of Cyclodextrins for Fulvestrant Aqueous Solubility Enhancement

A comprehensive selection of pharmaceutically acceptable cyclodextrins was selected for the solubility enhancement evaluation with fulvestrant. The most relevant characteristics of these cyclodextrins are presented in Table 9.

TABLE 9

Characteristics summary of cyclodextrins used in fulvestrant aqueous solubility evaluation.

| Cyclodextrin Type | Trade Name | Number of Glucopyranose Units | Abbreviation | Molecular Weight | Water Solubility (25° C.) (mg/mL) |
|---|---|---|---|---|---|
| Alpha-cyclodextrin | CAVAMAX ® W6 Pharma | 6 | ACD | 973 | 145 |
| Beta-cyclodextrin | CAVAMAX ® W7 Pharma | 7 | BCD | 1135 | 18.5 |
| Methyl beta-cyclodextrin | CAVASOL ® W7 M Pharma | 7 | MBCD | 1310 | >750 |
| Hydroxypropyl beta-cyclodextrin | KLEPTOSE ® HPB Pharma | 7 | HPBCD | 1400 | >750 |
| Sulfobutylether beta-cyclodextrin | | 7 | SBEBCD | 2163 | >500 |
| Gamma-cyclodextrin | CAVAMAX ® W8 Pharma | 8 | GCD | 1297 | 232 |
| Hydroxypropyl gamma-cyclodextrin | CAVASOL ® W8 HP Pharma | 8 | HPGCD | 1574 | >750 |

HPLC Instrumentation and Chemicals

The HPLC system used for the chromatographic determination of fulvestrant consisted of a Waters 600E quaternary gradient pump, a Waters 717plus WISP auto-sampler and a Waters 2487 Dual A, Absorbance detector. Separation was performed using a Phenomenex Luna C18 column (250×4.6 mm; 5 urn) (Phenomenex, Torrance, Calif.) (supplied by Separations, South Africa) and a mobile phase consisting of 50% MeCN:22.5% ddH$_2$O :27.5% MeOH. The mobile phase was degassed and filtered prior to use. An injection volume of 50 uL was selected, together with a flow rate of 1.2 mL/min, which resulted in fulvestrant peak retention times of approximately 11.2 minutes. Sample run times were 15 minutes. The UV detector wavelength was set to 280 nm.

The fulvestrant used for preparation of standard solutions, was of pharmaceutical grade. The acetonitrile used as mobile phase was of HPLC grade (Merck Chemicals, South Africa). Double distilled water (ddH$_2$O) was used at all times during the assay.

Stock fulvestrant solution was prepared according to the following steps: 1) 10 mg of fulvestrant powder was accurately weighed into a 10 mL volumetric flask; 2) the fulvestrant powder was dissolved and made to volume in mobile phase; 3) this solution was then vortexed for at least 20 seconds to ensure complete dissolution of the analyte. A concentration range of 10-500 µg/mL fulvestrant was prepared in the mobile phase. Calibration data generated during the fulvestrant aqueous solubility study for one of the fulvestrant calibration plots is presented in Table 10, with the graphical presentation of the data presented in FIG. 1. The method, which produced a linear plot, is suitable for the evaluation of fulvestrant.

TABLE 10

Fulvestrant HPLC calibration data.

| Fulvestrant Concentration (µg/mL) | Peak Area |
|---|---|
| 10 | 6017.79 |
| 20 | 11356.84 |
| 50 | 29814.88 |
| 100 | 57946.34 |
| 200 | 114870.10 |
| 300 | 173177.22 |
| 400 | 229736.60 |
| 500 | 287091.62 |

Results a. Alpha-Cyclodextrin (ACD)

The aqueous solubility of fulvestrant was evaluated in the presence of increasing concentrations of ACD and the absence thereof.

Figure 2:
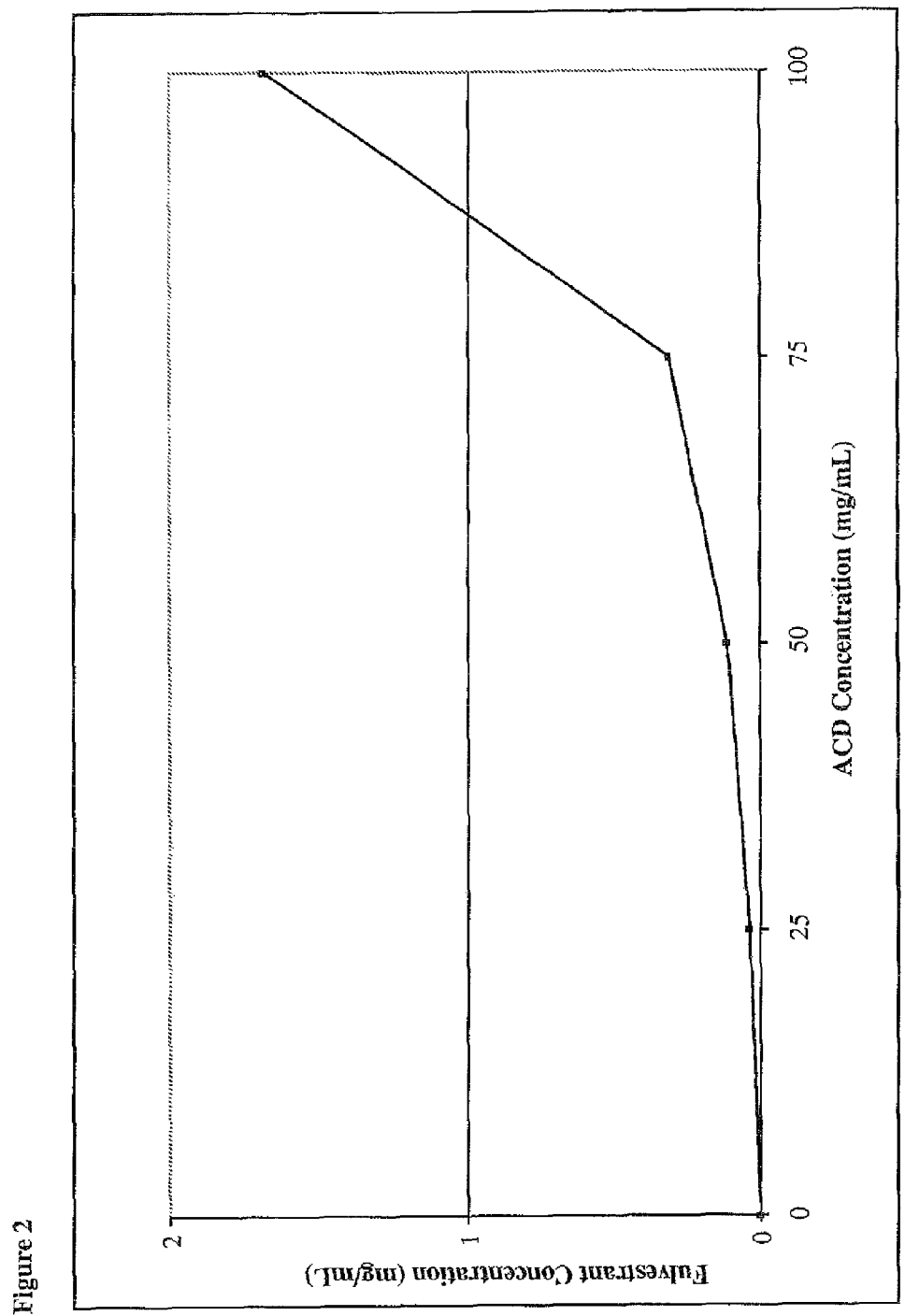
FIG. 2 shows a fulvestrant aqueous solubility data plot in the presence and absence of various concentrations of alpha-cyclodextrin (ACD).

1 mL of each of the following aqueous solutions was prepared containing 0; 25; 50; 75 and 100 mg/mL ACD in ddHiO. Excess fulvestrant was added to each of these solutions and the samples were shaken for 24 hours on an orbital shaker at 200 rpm and at 22° C. room temperature. Excess fulvestrant was present in all samples at all times. After 24-hours, the samples were filtered through 0.45 µm syringe tip filters, diluted according to requirements and assayed by HPLC. The fulvestrant aqueous solubility results are presented in Table 11 and FIG. 2.

TABLE 11

Fulvestrant aqueous solubility data in the presence and absence of various concentrations of ACD.

| Sample No. | ACD Concentration (mg/mL) | Quantity of Fulvestrant Diluted (µg/mL) Run1 | Quantity of Fulvestrant Diluted (µg/mL) Run 2 | Average Concentration (µg/mL) | True Fulvestrant Concentration (mg/mL) |
|---|---|---|---|---|---|
| 1 | 0 | <10.000 | <10.010 | <10.00 | <0.010 |
| 2 | 25 | 33.620 | 32.970 | 33.30 | 0.033 |
| 3 | 50 | 110.600 | 110.880 | 110.74 | 0.111 |
| 4 | 75 | 310.460 | 310.170 | 310.32 | 0.310 |
| 5 | 100 | 162.660 | 173.850 | 168.26 | 1.683 | b. Beta-Cyclodextrin (BCD)

Figure 3:
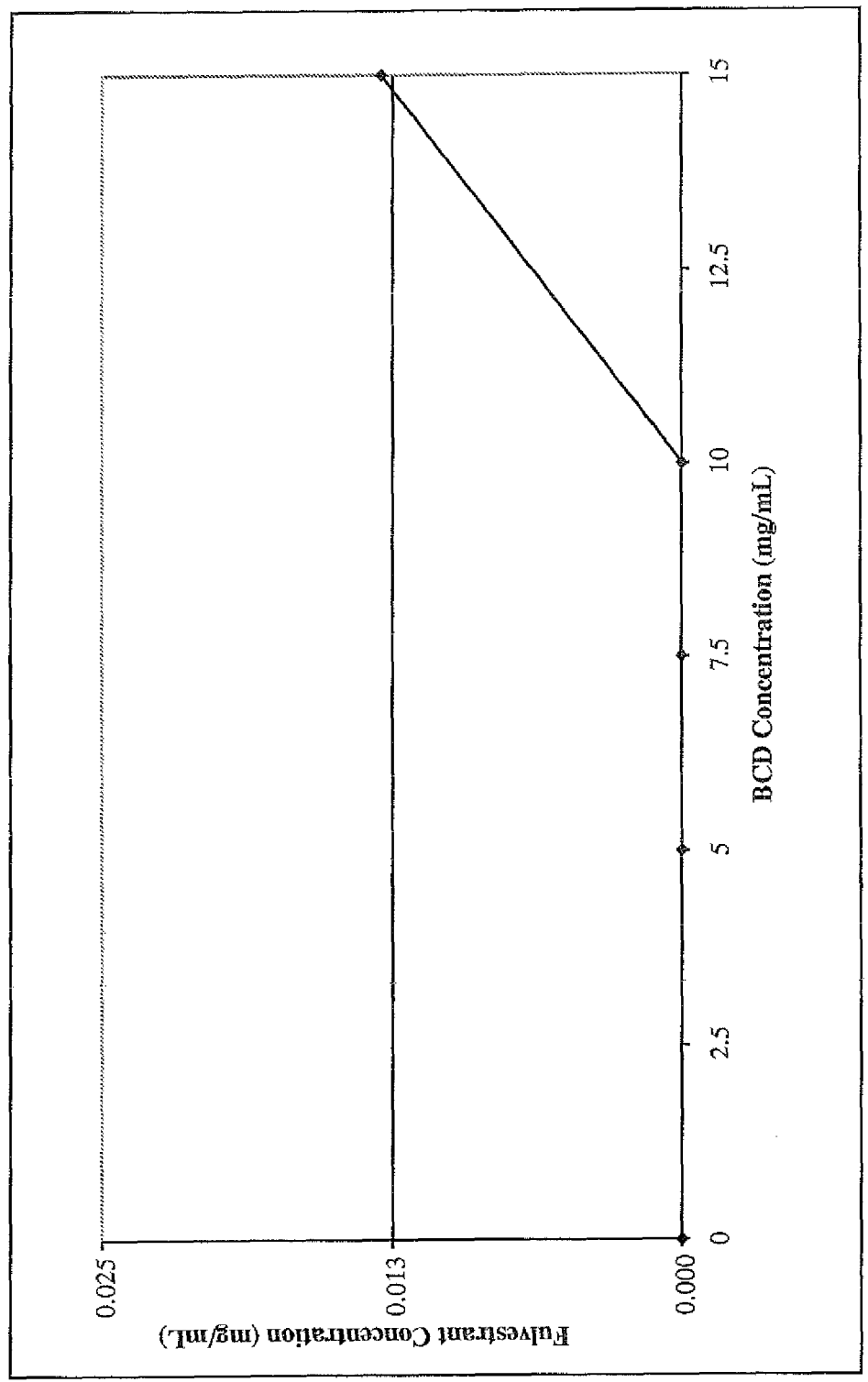
FIG. 3 shows a fulvestrant aqueous solubility data plot in the presence and absence of various concentrations of beta-cyclodextrin (BCD).

The aqueous solubility of fulvestrant was evaluated in the presence of increasing concentrations of BCD and the absence thereof 1 mL of each of the following aqueous solutions was prepared containing 0; 5; 7.5; 10 and 15 mg/mL BCD in ddH$_2$O. Excess fulvestrant was added to each of these solutions and the samples were shaken for 24 hours on an orbital shaker at 200 rpm and at 22° C. room temperature. Excess fulvestrant was present in all samples at all times. After 24-hours, the samples were filtered through 0.45 μm syringe tip filters, diluted according to requirements and assayed by HPLC. The fulvestrant aqueous solubility results are presented in Table 12 and FIG. 3.

TABLE 12

Fulvestrant aqueous solubility data in the presence and absence of various concentrations of BCD.

| Sample No. | BCD Concentration (mg/mL) | Quantity of Fulvestrant Diluted (μg/mL) Run 1 | Quantity of Fulvestrant Diluted (μg/mL) Run 2 | Average Concentration (μg/mL) | True Fulvestrant Concentration (mg/mL) |
|---|---|---|---|---|---|
| 1 | 0 | <10.000 | <10.000 | <10.00 | <0.010 |
| 2 | 5 | <10.000 | <10.000 | <10.00 | <0.010 |
| 3 | 7.5 | <10.000 | <10.000 | <10.00 | <0.010 |
| 4 | 10 | <10.000 | <10.000 | <10.00 | <0.010 |
| 5 | 15 | 13.060 | 12.940 | 13.00 | 0.013 | c. Methyl Beta-Cyclodextrin (MBCD)

The aqueous solubility of fulvestrant was evaluated in the presence of increasing concentrations of MBCD and the absence thereof.

Figure 4:
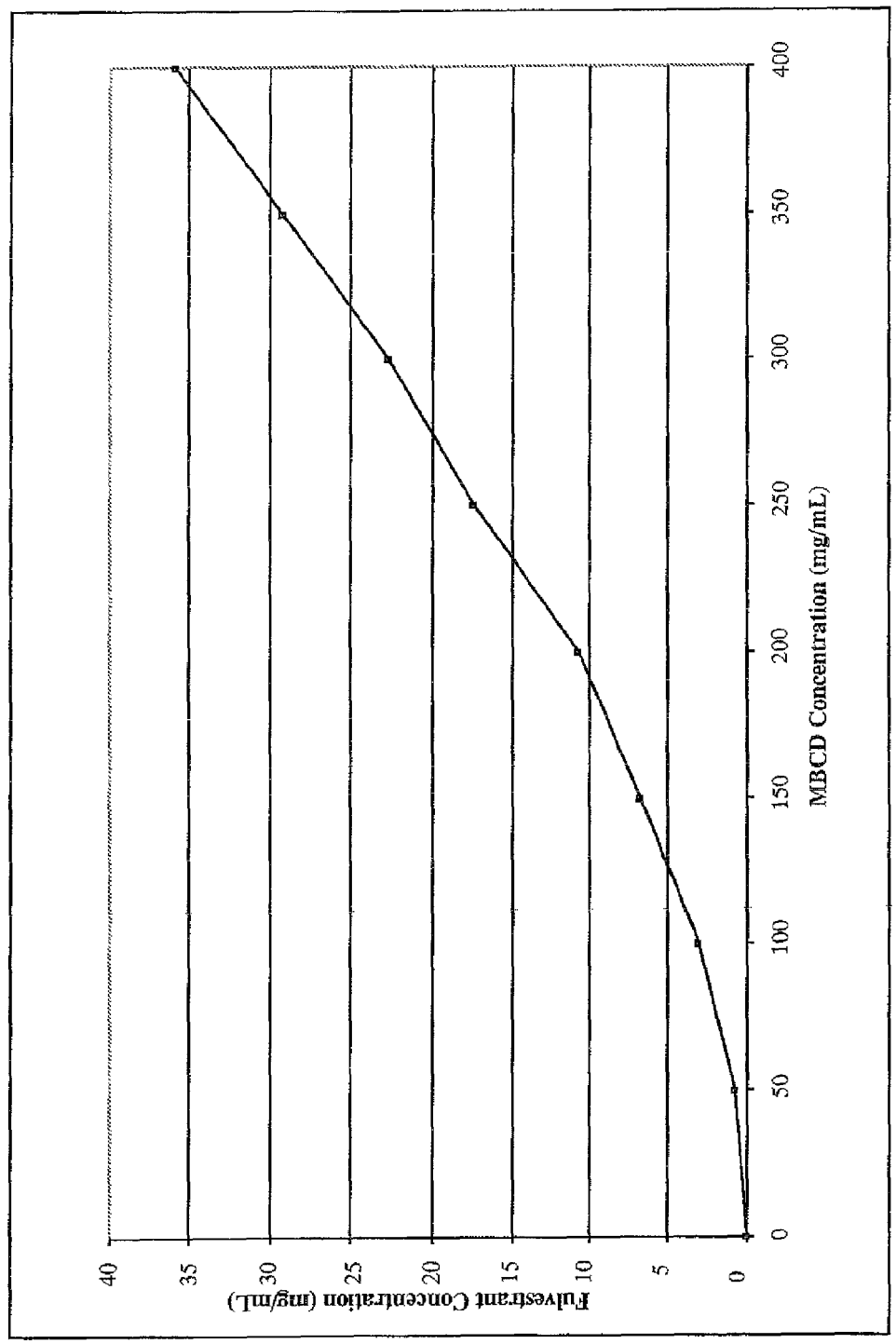
FIG. 4 shows a fulvestrant aqueous solubility data plot in the presence and absence of various concentrations of methyl beta-cyclodextrin (MBCD).

1 mL of each of the following aqueous solutions was prepared containing 0; 50; 100; 150; 200; 250; 300; 350 and 400 mg/mL MBCD in ddH$_2$O. Excess fulvestrant was added to each of these solutions and the samples were shaken for 24 hours on an orbital shaker at 200 rpm and at 22° C. room temperature. Excess fulvestrant was present in all samples at all times. After 24-hours, the samples were filtered through 0.45 μm syringe tip filters, diluted according to requirements and assayed by HPLC. The fulvestrant aqueous solubility results are presented in Table 13 and FIG. 4.

TABLE 13

Fulvestrant aqueous solubility data in the presence and absence of various concentrations of MBCD.

| Sample No. | MBCD Concentration (mg/mL) | Quantity of Fulvestrant Diluted (μg/mL) Run 1 | Quantity of Fulvestrant Diluted (μg/mL) Run 2 | Average Concentration (μg/mL) | True Fulvestrant Concentration (mg/mL) |
|---|---|---|---|---|---|
| 1 | 0 | <10.00 | <10.00 | <10.00 | <0.010 |
| 2 | 50 | 74.61 | 75.37 | 74.99 | 0.750 |
| 3 | 100 | 302.12 | 301.99 | 302.06 | 3.021 |
| 4 | 150 | 67.40 | 67.47 | 67.44 | 6.744 |
| 5 | 200 | 106.87 | 107.01 | 106.94 | 10.694 |
| 6 | 250 | 174.30 | 174.28 | 174.29 | 17.429 |
| 7 | 300 | 226.52 | 226.94 | 226.73 | 22.673 |
| 8 | 350 | 293.21 | 292.29 | 292.75 | 29.275 |
| 9 | 400 | 359.13 | 358.71 | 358.92 | 35.892 | d. Hydroxypropyl Beta-Cyclodextrin (HPBCD)

Figure 5:
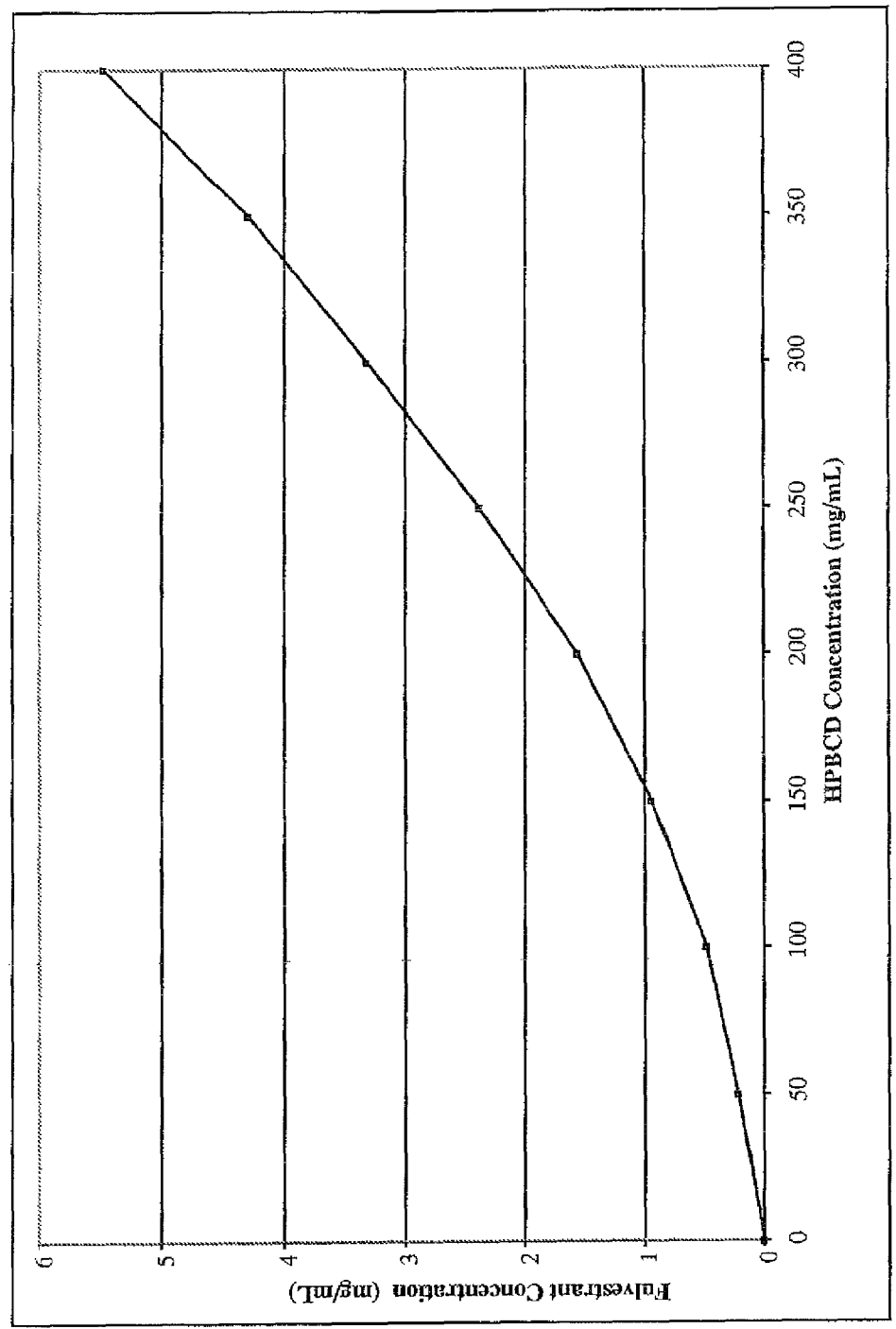
FIG. 5 shows a fulvestrant aqueous solubility data plot in the presence and absence of various concentrations of hydroxypropyl beta-cyclodextrin (HPBCD).

The aqueous solubility of fulvestrant was evaluated in the presence of increasing concentrations of HPBCD and the absence thereof 1 mL of each of the following aqueous solutions was prepared containing 0; 50; 100; 150; 200; 250; 300; 350 and 400 mg/mL HPBCD in ddH$_2$O. Excess fulvestrant was added to each of these solutions and the samples were shaken for 24 hours on an orbital shaker at 200 rpm and at 22° C. room temperature. Excess fulvestrant was present in all samples at all times. After 24-hours, the samples were filtered through 0.45 μm syringe tip filters, diluted according to requirements and assayed by HPLC. The fulvestrant aqueous solubility results are presented in Table 14 and FIG. 5.

TABLE 14

Fulvestrant aqueous solubility data in the presence
and absence of various concentrations of HPBCD.

| Sample No. | HPBCD Concentration (mg/mL) | Quantity of Fulvestrant Diluted (µg/mL) Run 1 | Quantity of Fulvestrant Diluted (µg/mL) Run 2 | Average Concentration (µg/mL) | True Fulvestrant Concentration (mg/mL) |
|---|---|---|---|---|---|
| 1 | 0 | <10.00 | <10.00 | <10.00 | <0.010 |
| 2 | 50 | 21.09 | 20.81 | 20.95 | 0.210 |
| 3 | 100 | 48.32 | 48.27 | 48.30 | 0.483 |
| 4 | 150 | 93.82 | 93.50 | 93.66 | 0.937 |
| 5 | 200 | 156.30 | 42.30 | 99.30 | 1.563 |
| 6 | 250 | 118.71 | 118.97 | 118.84 | 2.377 |
| 7 | 300 | 164.70 | 166.54 | 165.62 | 3.312 |
| 8 | 350 | 215.41 | 215.10 | 215.26 | 4.305 |
| 9 | 400 | 275.20 | 272.14 | 273.67 | 5.473 | e. Sulfobutylether Beta-Cyclodextrin (SBEBCD)

The aqueous solubility of fulvestrant was evaluated in the presence of increasing concentrations of SBEBCD and the absence thereof.

Figure 6:
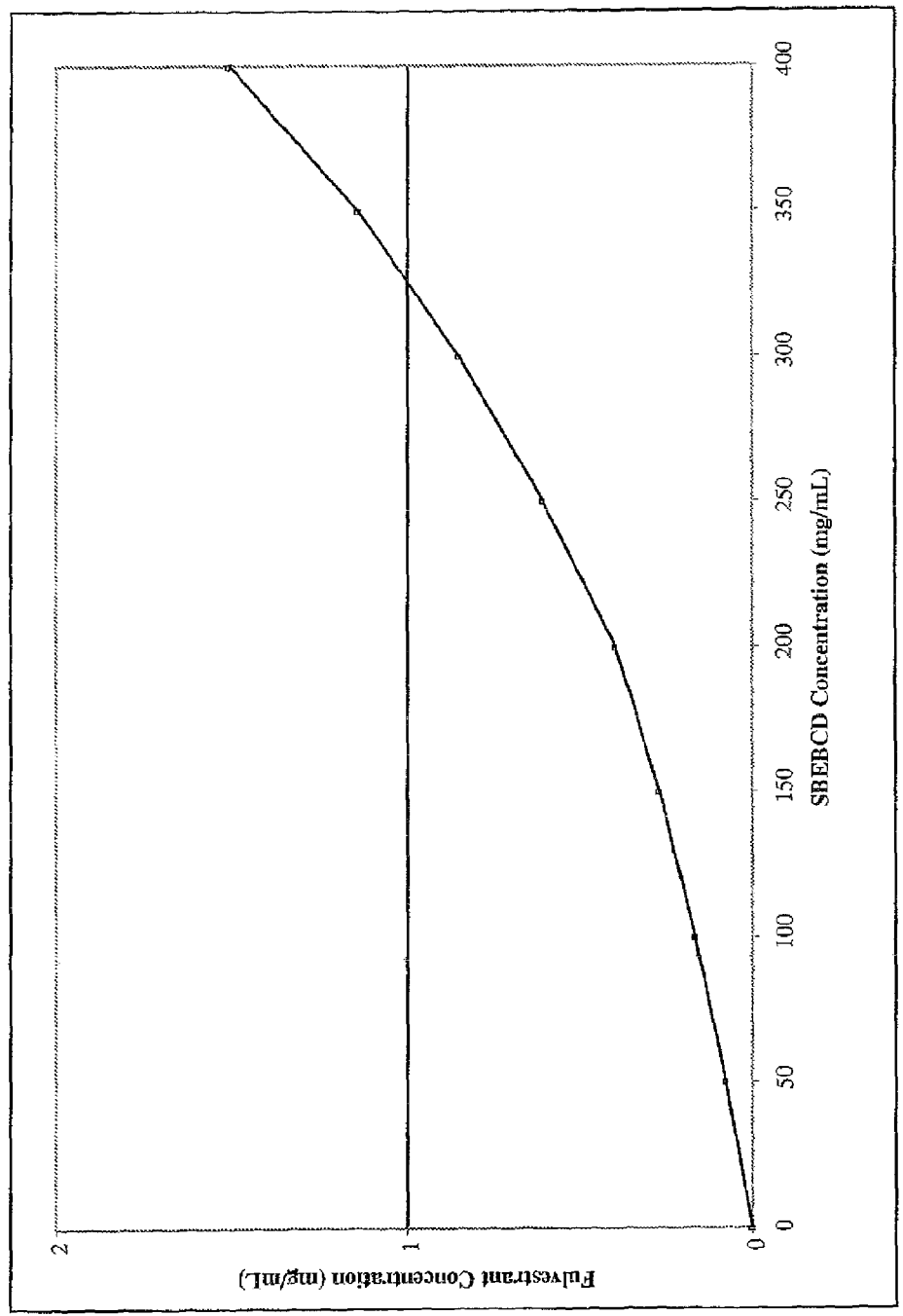
FIG. 6 shows a fulvestrant aqueous solubility data plot in the presence and absence of various concentrations of sulfobutylether beta-cyclodextrin (SBEBCD).

1 mL of each of the following aqueous solutions was prepared containing 0; 50; 100; 150; 200; 250; 300; 350 and 400 mg/mL SBEBCD in ddH$_2$O. Excess fulvestrant was added to each of these solutions and the samples were shaken for 24 hours on an orbital shaker at 200 rpm and at 22° C. room temperature. Excess fulvestrant was present in all samples at all times. After 24-hours, the samples were filtered through 0.45 µm syringe tip filters, diluted according to requirements and assayed by HPLC. The fulvestrant aqueous solubility results are presented in Table 15 and FIG. 6.

f. Gamma-Cyclodxtrin (GCD)

The aqueous solubility of fulvestrant was evaluated in the presence of increasing concentrations of GCD and the absence thereof.

Figure 7:
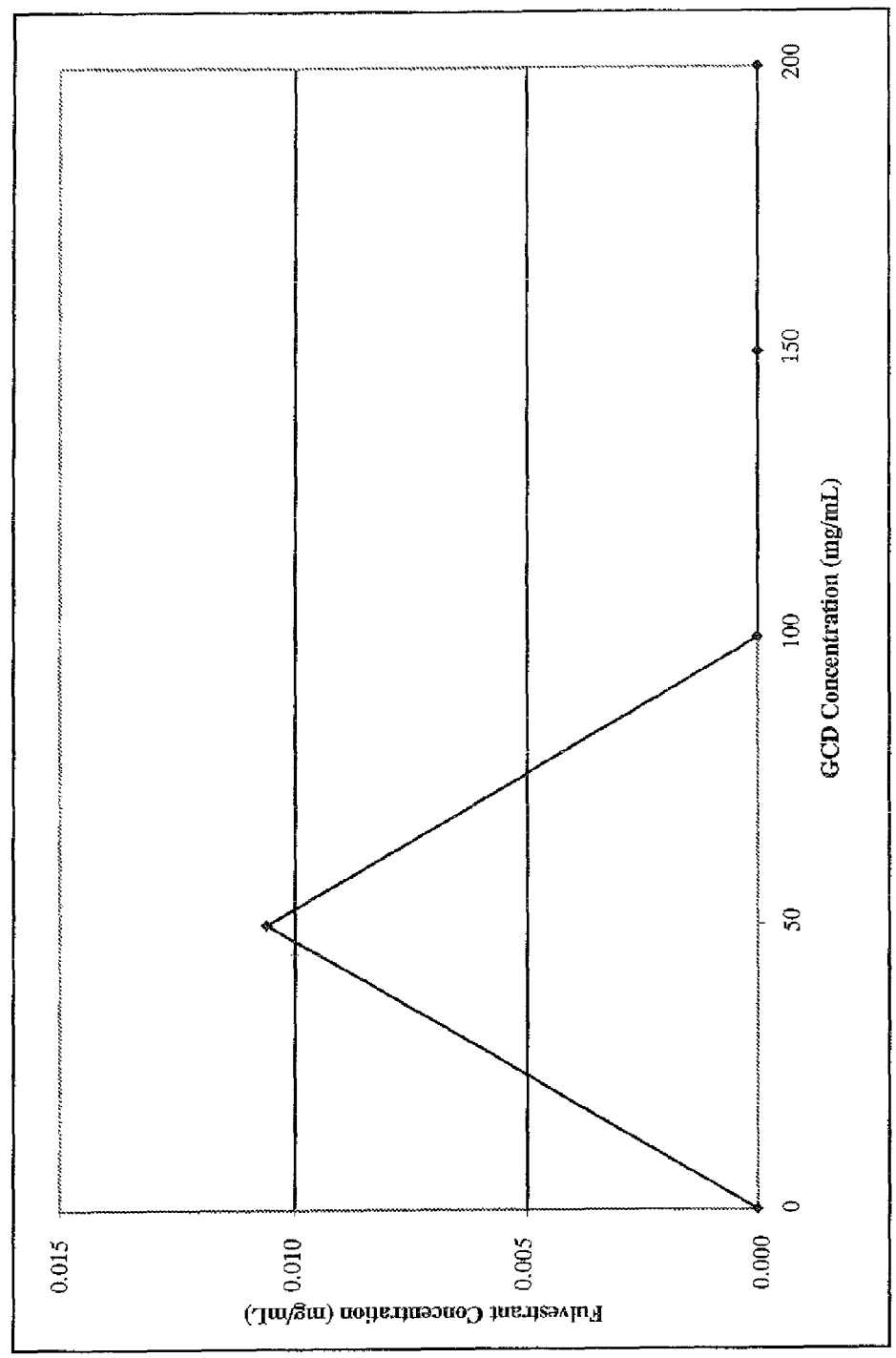
FIG. 7 shows a fulvestrant aqueous solubility data plot in the presence and absence of various concentrations of gamma-cyclodextrin (GCD).

1 mL of each of the following aqueous solutions was prepared containing 0; 50; 100; 150; and 200 mg/mL GCD in ddHO. Excess fulvestrant was added to each of these solutions and the samples were shaken for 24 hours on an orbital shaker at 200 rpm and at 22° C. room temperature. Excess fulvestrant was present in all samples at all times. After 24-hours, the samples were filtered through 0.45 µm syringe tip filters, diluted according to requirements and assayed by HPLC. The fulvestrant aqueous solubility results are presented in Table 16 and FIG. 7.

TABLE 15

Fulvestrant aqueous solubility data in the presence
and absence of various concentrations of SBEBCD.

| Sample No. | SBEBCD Concentration (mg/mL) | Quantity of Fulvestrant Diluted (µg/mL) Run 1 | Quantity of Fulvestrant Diluted (µg/mL) Run 2 | Average Concentration (µg/mL) | True Fulvestrant Concentration (mg/mL) |
|---|---|---|---|---|---|
| 1 | 0 | <10.00 | <10.00 | <10.00 | <0.010 |
| 2 | 50 | 76.98 | 77.61 | 77.30 | 0.077 |
| 3 | 100 | 167.7 | 166.49 | 167.10 | 0.167 |
| 4 | 150 | 273.01 | 272.83 | 272.92 | 0.273 |
| 5 | 200 | 398.52 | 399.09 | 398.81 | 0.399 |
| 6 | 250 | 304.32 | 305.15 | 304.74 | 0.609 |
| 7 | 300 | 425.82 | 425.96 | 425.89 | 0.852 |
| 8 | 350 | 382.24 | 377.67 | 379.96 | 1.140 |
| 9 | 400 | 503.13 | 501.21 | 502.17 | 1.507 |

TABLE 16

Fulvestrant aqueous solubility data in the presence
and absence of various concentrations of GCD.

| Sample No. | GCD Concentration (mg/mL) | Quantity of Fulvestrant Diluted (µg/mL) Run 1 | Quantity of Fulvestrant Diluted (µg/mL) Run 2 | Average Concentration (µg/mL) | True Fulvestrant Concentration (mg/mL) |
|---|---|---|---|---|---|
| 1 | 0 | <10.000 | <10.000 | <10.00 | <0.010 |
| 2 | 50 | 10.700 | 10.530 | 10.62 | 0.011 |
| 3 | 100 | <10.000 | <10.000 | <10.00 | <0.010 |
| 4 | 150 | <10.000 | <10.000 | <10.00 | <0.010 |
| 5 | 200 | <10.000 | <10.000 | <10.00 | <0.010 | g. Hydroxypropyl Gamma-Cyclodextrin (HPGCD)

The aqueous solubility of fulvestrant was evaluated in the presence of increasing concentrations of HPGCD and the absence thereof.

Figure 8:
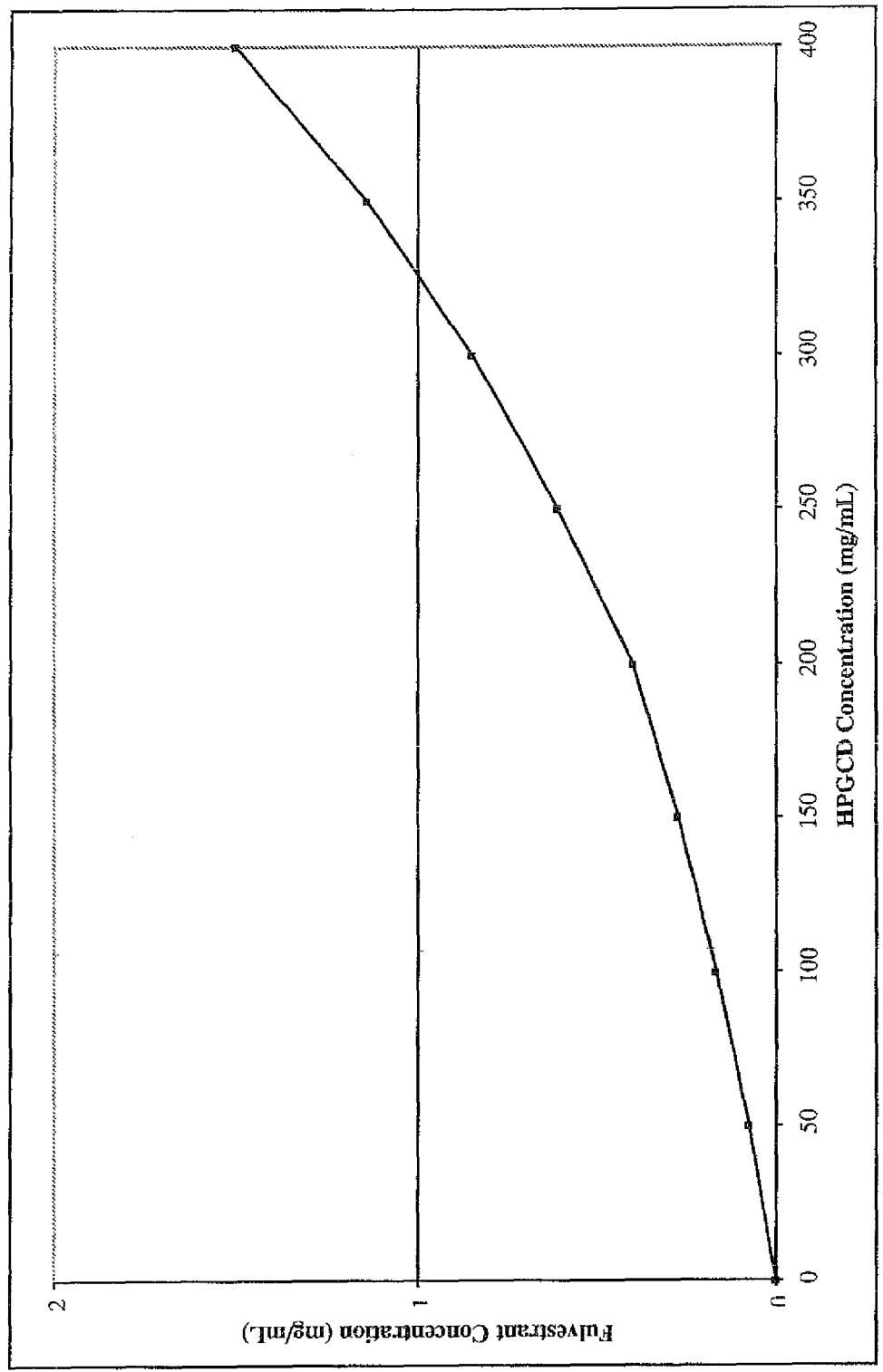
FIG. 8 shows a fulvestrant aqueous solubility data plot in the presence and absence of various concentrations of hydroxypropyl gamma-cyclodextrin (HPGCD).
Figure 9:
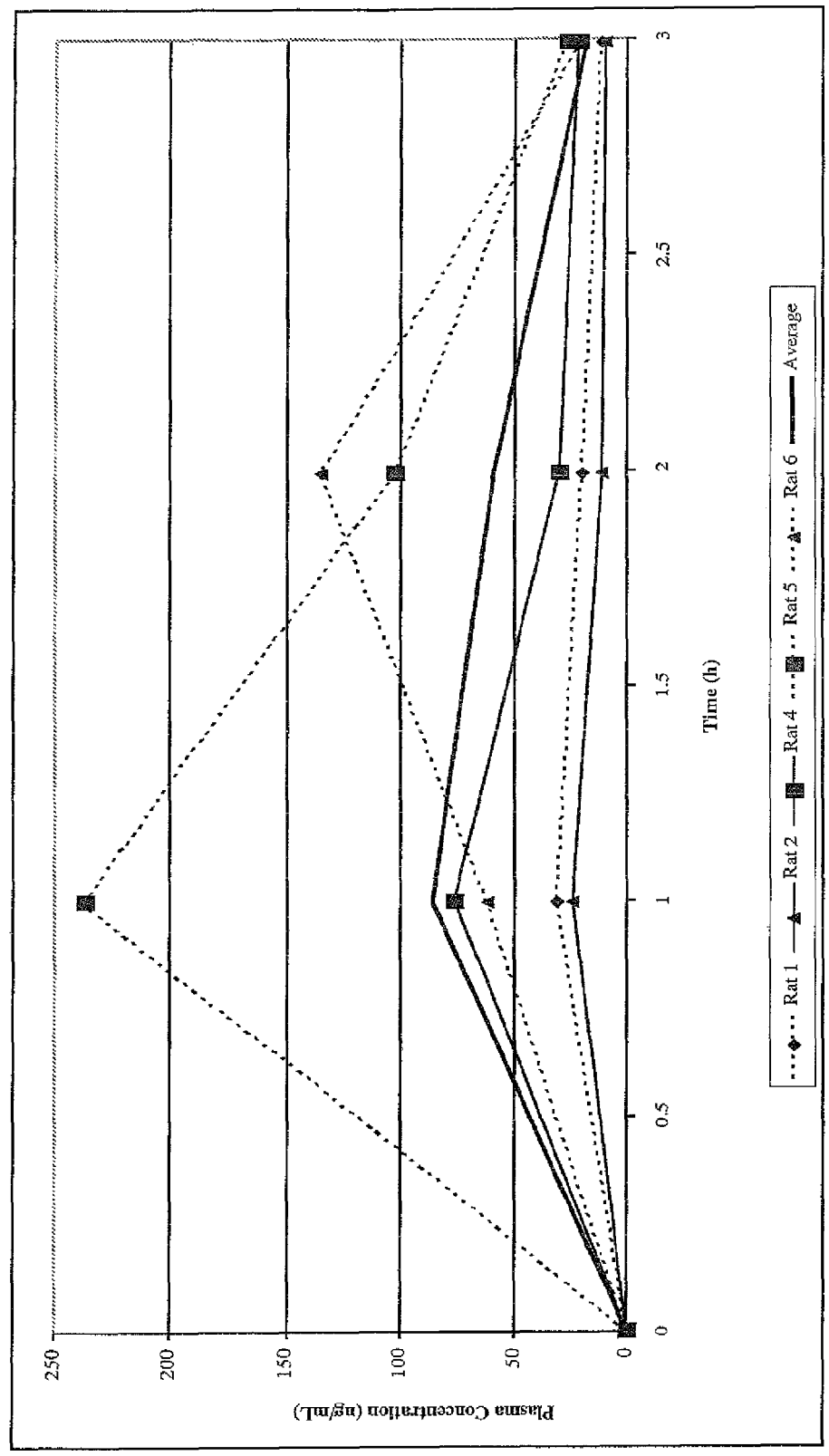
FIG. 9 shows a fulvestrant plasma concentration data plot generated for Experiment I (oral gavage of fulvestrant-HPBCD).
Figure 10:
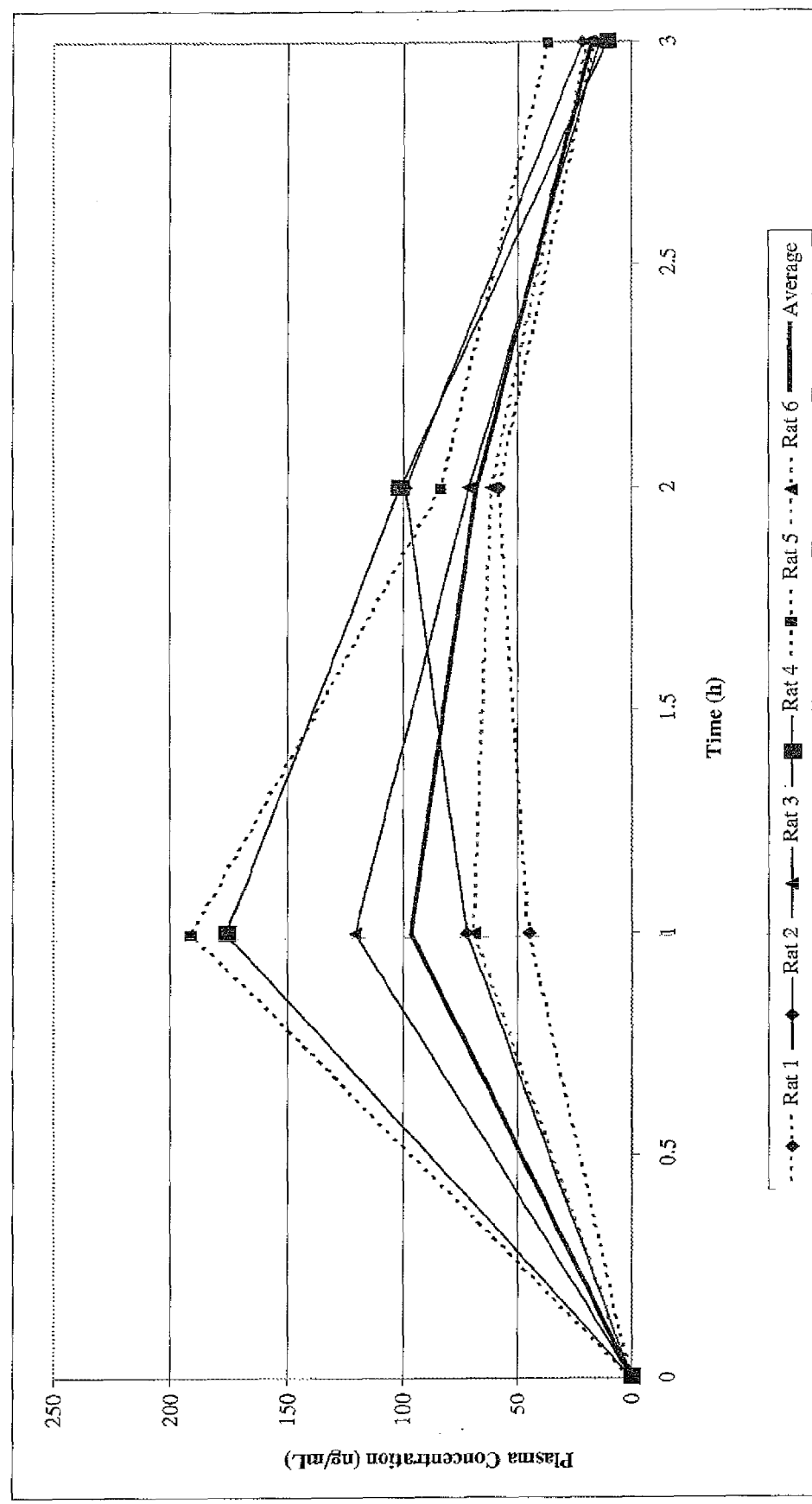
FIG. 10 shows a fulvestrant plasma concentration data plot generated for Experiment II (oral gavage of fulvestrant-MBCD).
Figure 11:
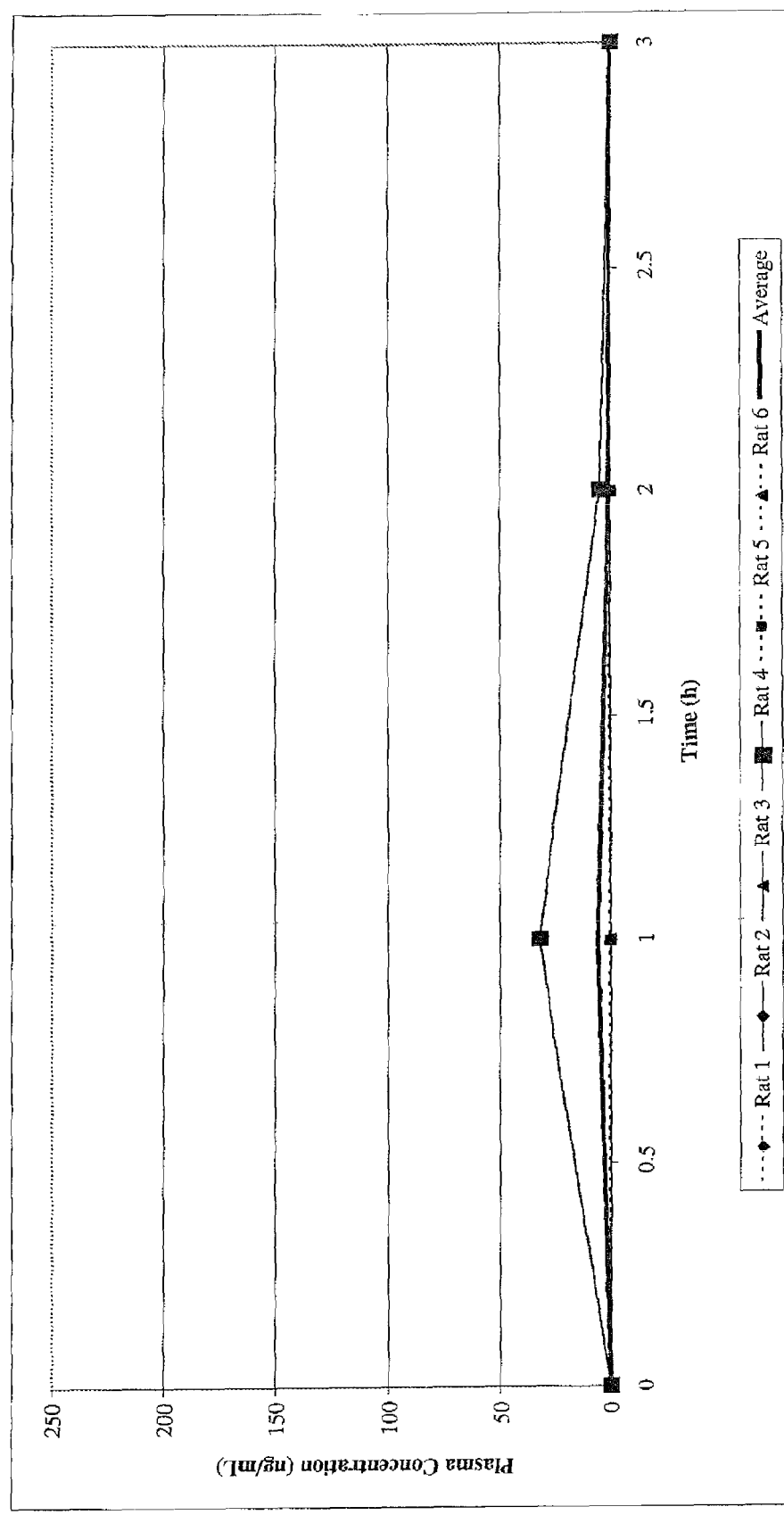
FIG. 11 shows a fulvestrant plasma concentration data plot generated for Experiment III (oral gavage without cyclodextrin (CD)).

1 mL of each of the following aqueous solutions was prepared containing 0; 50; 100; 150; 200; 250; 300; 350 and 400 mg/mL HPGCD in ddH$_2$O. Excess fulvestrant was added to each of these solutions and the samples were shaken for 24 hours on an orbital shaker at 200 rpm and at 22° C. room temperature. Excess fulvestrant was present in all samples at all times. After 24-hours, the samples were filtered through 0.45 µm syringe tip filters, diluted according to requirements and assayed by HPLC. The fulvestrant aqueous solubility results are presented in Table 17 and FIG. 8.

TABLE 17

Fulvestrant aqueous solubility data in the presence and absence of various concentrations of HPGCD.

| Sample No. | HPGCD Concentration (mg/mL) | Quantity of Fulvestrant Diluted (µg/mL) Run 1 | Quantity of Fulvestrant Diluted (µg/mL) Run 2 | Average Concentration (µg/mL) | True Fulvestrant Concentration (mg/mL) |
|---|---|---|---|---|---|
| 1 | 0 | <10.00 | <10.00 | <10.00 | <0.010 |
| 2 | 50 | 38.66 | 37.97 | 38.32 | 0.037 |
| 3 | 100 | 116.80 | 115.74 | 116.27 | 0.107 |
| 4 | 150 | 220.67 | 220.94 | 220.81 | 0.203 |
| 5 | 200 | 334.75 | 334.66 | 334.71 | 0.300 |
| 6 | 250 | 474.68 | 472.99 | 473.84 | 0.215 |
| 7 | 300 | 400.24 | 384.76 | 392.50 | 0.603 |
| 8 | 350 | 500.71 | 505.22 | 502.97 | 0.802 |
| 9 | 400 | 486.39 | 450.47 | 468.43 | 1.061 |

Discussion

From the results presented in Tables 11 to 17 and FIGS. 2 to 8, it is clear that fulvestrant forms inclusion complexes with cyclodextrins to greater and lesser extents, depending on the specific cyclodextrin. Fulvestrant aqueous solubility enhancements with ACD; SBEBCD and HPGCD yielded fulvestrant aqueous solubilities of between 1 to 2 mg/mL, which was a significant enhancement over the aqueous solubility of fulvestrant in the absence of these cyclodextrins. The aqueous solubility enhancements of fulvestrant with BCD and GCD were lower. The aqueous solubility of fulvestrant in the presence of HPBCD was enhanced from below 0.010 mg/mL to 5.5 mg/mL in 400 mg/mL HPBCD. The greatest aqueous solubility enhancement of fulvestrant was, however, achieved with MBCD, whereby the fulvestrant aqueous solubility was significantly enhanced from below 0.010 mg/mL to 35.9 mg/mL in 400 mg/mL MBCD.

Example 2

Oral Fulvestrant Absorption Study in Male Whistar Rats

The comparative oral absorption of two novel aqueous cyclodextrin based formulations of fulvestrant versus an uncomplexed fulvestrant aqueous suspension (without any cyclodextrins) following oral administrations of 10 mg/kg by gavage to adult male Whistar rats was assessed.

Materials and Methods

The study was conducted using eighteen male adult Whistar rats. Each rat partook in a single experiment. Fulvestrant was administered at a dose of 10 mg/kg by oral gavage to each animal, with blood concentrations measured hourly over a 3-hour period.

The test articles were considered to be >99% pure and contained 5 mg/mL of fulvestrant. The vehicles used to prepare the two novel batches comprised 400 mg/mL hydroxypropyl beta-cyclodextrin (HPBCD) (Batch 1) and 400 mg/mL methyl beta-cyclodextrin (MBCD) (Batch 2). The control fulvestrant formulation comprised of a 5 mg/mL fulvestrant suspension in ddH$_2$O (Batch 3). All animals were fasted for approximately 24 hours prior to dose administration. Water was available ad libitum. Pre-dose, and 1 h and 2 h post dose blood sampling was conducted by means of the tail snip procedure, whereby 0.5 mL was collected at each sampling point. Five minutes prior to the final (3 h) blood sampling point, rats were anaesthetized with 0.5 ml 6% sodium pentobarbitone and 5 mL blood was collected. Prior to drug administration by means of gavage, each of the rats was anaesthetized with halothane gas, following which a gavage tube was inserted through the mouth and through which the various solutions were administered. 0.5 mL saline was administered through the gavage tubes immediately following drug administration.

The information for Experiments I to III are summarized in Tables 18 to 20 respectively.

TABLE 18

Experiment I Information.

| Formulation | Rat No. | Dose | Dose volume | Rat Mass |
|---|---|---|---|---|
| Fulvestrant Batch 1 | 1 | 10 mg/kg | 0.58 mL | 0.290 kg |
| Fulvestrant Batch 1 | 2 | 10 mg/kg | 0.54 mL | 0.270 kg |
| Fulvestrant Batch 1 | 3 | 10 mg/kg | 0.51 mL | 0.254 kg |
| Fulvestrant Batch 1 | 4 | 10 mg/kg | 0.62 mL | 0.309 kg |
| Fulvestrant Batch 1 | 5 | 10 mg/kg | 0.53 mL | 0.264 kg |
| Fulvestrant Batch 1 | 6 | 10 mg/kg | 0.54 mL | 0.270 kg |

TABLE 19

Experiment II Information

| Formulation | Rat No. | Dose | Dose volume | Rat Mass |
|---|---|---|---|---|
| Fulvestrant Batch 2 | 1 | 10 mg/kg | 0.52 mL | 0.261 kg |
| Fulvestrant Batch 2 | 2 | 10 mg/kg | 0.54 mL | 0.271 kg |
| Fulvestrant Batch 2 | 3 | 10 mg/kg | 0.61 mL | 0.304 kg |
| Fulvestrant Batch 2 | 4 | 10 mg/kg | 0.57 mL | 0.287 kg |
| Fulvestrant Batch 2 | 5 | 10 mg/kg | 0.60 mL | 0.300 kg |
| Fulvestrant Batch 2 | 6 | 10 mg/kg | 0.57 mL | 0.284 kg |

TABLE 20

Experiment III information.

| Formulation | Rat No. | Dose | Dose volume | Rat Mass |
|---|---|---|---|---|
| Fulvestrant Batch 3 | 1 | 10 mg/kg | 0.56 mL | 0.278 kg |
| Fulvestrant Batch 3 | 2 | 10 mg/kg | 0.51 mL | 0.253 kg |
| Fulvestrant Batch 3 | 3 | 10 mg/kg | 0.54 mL | 0.271 kg |
| Fulvestrant Batch 3 | 4 | 10 mg/kg | 0.53 mL | 0.267 kg |
| Fulvestrant Batch 3 | 5 | 10 mg/kg | 0.53 mL | 0.265 kg |
| Fulvestrant Batch 3 | 6 | 10 mg/kg | 0.57 mL | 0.284 kg |

Blood Sampling and Bioanalytical Methods

All of the animals that were dosed by means of oral gavage were bled pre-dose, and at 1 hour (h) and 2 h post dose, with blood sampling having been conducted by means of the tail snip procedure, whereby 0.5 mL was collected at each sampling point. Five minutes prior to the terminal blood sampling point (3 h), rats were anaesthetized with 0.5 ml 6% sodium pentobarbitone and 5 mL blood was collected from each, after which the rats were sacrificed.

The tail snip blood was collected in 1 mL K3E ($K_3$EDTA) MINICOLLECT® (Greiner Bio-one; Lot 090319; Exp. 2010-08) blood collection tubes, with the terminal samples having been collected in 9 mL K3E ($K_3$EDTA) VACU-ETTE® (Greiner Bio-one; Lot A090602D; Exp. 2010-12) blood collection tubes. Following collection, the samples were placed on ice and then centrifuged at 4° C. for 15 minutes. 0.2 mL and 2 mL plasma aliquots were obtained from the tail snip and terminal sampling points respectively. These samples were frozen (−60° C. to −80° C.) prior to being shipped on dry ice to a facility for analysis of fulvestrant concentrations.

Bioanalytical Methodology and Calculation of Pharmacokinetic (PK) Parameters

The test article, fulvestrant, was measured in adult Whistar rat plasma via a liquid chromatography-mass spectroscopy (LC-MS) method, as described below.

A sensitive and selective LC-MS/MS method was developed and used to determine fulvestrant in rat plasma. Prior to assay, rat plasma samples were thawed at room temperature, briefly vortexed, after which 100 uL plasma was pipetted into 1.5 ml Eppendorf® Safe-Lock® microcentrifuge tubes. Samples were then precipitated with methanol (200 uL) containing the internal standard, doxepin (245 ng/mL). These samples were vortexed for 30 seconds and centrifuged for 5 minutes at 15 000 rpm. The supernatant (200 uL) was transferred to 96 well plates and 5 uL was injected onto the HPLC column. Calibration standards were prepared in rat plasma (anticoagulant lithium heparinate), whereby a stock solutions of fulvestrant in methanol was used to spike a pool of blank rat plasma which was serially diluted with blank rat plasma to attain the desired concentrations, spanning a range of 4.5 ng/mL to 1149 ng/mL (STD 1-STD 9).

Chromatography was performed on a Phenomenex, Luna Phenyl Hexyl, (150×2.1 mm, 5 um) analytical column. The mobile phase consisted of methanol and 5 mM ammonium formate (80:20 v/v) and was delivered at a constant flow rate of 0.3 mL/min for 7.5 minutes. An Agilent 1100 series autosampler injected 5 uL onto the HPLC column. The injection needle was rinsed with water methanol (50:50) for 10 seconds using the flush port wash station. Samples were cooled to ~5° C. while awaiting injection. Detection was performed on an API 4000 mass spectrometer (ESI in the positive ion mode, MRM) and the settings on the apparatus are summarized in tables below.

TABLE 21A

| ESI settings | |
|---|---|
| Curtain gas | 30 |
| Collision gas | 7 |
| Ionspray voltage (V) | 5500 |
| Source temperature (° C.) | 450 |
| Gas 1 (psi) | 30 |
| Gas 2 (psi) | 40 |

TABLE 21B

MS/MS settings

| | Fulvestrant | Internal standard |
|---|---|---|
| Q1 mass [M + H]+ | 607.3 | 279.9 |
| Q3 mass | 589.2 | 107.2 |
| Dwell time (ms) | 150 | 150 |
| Declustering potential (V) | 76 | 61 |
| Entrance potential (V) | 10 | 10 |
| Collision energy (V) | 23 | 31 |
| Collision cell exit potential (V) | 22 | 8 |
| Scan type | MRM | MRM |
| Polarity | positive | positive |
| Pause time (ms) | 5 | 5 |

Results a. Plasma Concentration-Time Profiles for Orally Administered Fulvestrant Individual fulvestrant plasma concentrations for Experiments I, I, and III are presented in Tables 22 to 24. Individual and mean plasma fulvestrant concentration-time profiles following oral administration by gavage for Experiments I, II, and III are presented in FIGS. 9 to 12.

TABLE 22

Fulvestrant plasma concentration data generated for Experiment I (HPBCD).

| | Plasma concentration (ng/mL) | | | |
|---|---|---|---|---|
| | 0 h | 1 h | 2 h | 3 h |
| Rat 1 | 0.00 | 30.90 | 20.10 | 11.20 |
| Rat 2 | 0.00 | 23.80 | 11.60 | 9.63 |
| *Rat 3** | *0.00* | *608.00* | *239.00* | *45.70* |
| Rat 4 | 0.00 | 76.70 | 30.30 | 21.80 |
| Rat 5 | 0.00 | 237.00 | 103.00 | 26.40 |
| Rat 6 | 0.00 | 62.00 | 135.00 | 20.50 |

*The data from rat 3 in Experiment I was regarded as being an outlier and as such, it was not included in the average data calculation.

TABLE 23

Fulvestrant plasma concentration data generated for Experiment II (MBCD).

| | Plasma concentration (ng/mL) | | | |
|---|---|---|---|---|
| | 0 h | 1 h | 2 h | 3 h |
| Rat 1 | 0.00 | 45.40 | 58.20 | 15.50 |
| Rat 2 | 0.00 | 72.10 | 98.90 | 21.30 |
| Rat 3 | 0.00 | 121.00 | 71.60 | 14.00 |
| Rat 4 | 0.00 | 177.00 | 102.00 | 10.60 |
| Rat 5 | 0.00 | 191.00 | 83.00 | 36.40 |
| Rat 6 | 0.00 | 68.90 | 61.60 | 18.80 |
| Average | 0.00 | 96.63 | 68.19 | 17.09 |

TABLE 24

Fulvestrant plasma concentration data generated for Experiment III (No CD).

| | Plasma concentration (ng/ml) | | | |
|---|---|---|---|---|
| | 0 h | L h | 2 h | 3 h |
| Rat 1 | 0.00 | 0.00 | 0.00 | 0.00 |
| Rat 2 | 0.00 | 0.00 | 0.00 | 0.00 |
| Rat 3 | 0.00 | 0.00 | 0.00 | 0.00 |
| Rat 4 | 0.00 | 32.40 | 4.75 | 0.00 |
| Rat 5 | 0.00 | 0.00 | 0.00 | 0.00 |
| Rat 6 | 0.00 | 0.00 | 0.00 | 0.00 |
| Average | 0.00 | 5.40 | 0.79 | 0.00 |

Figure 12:
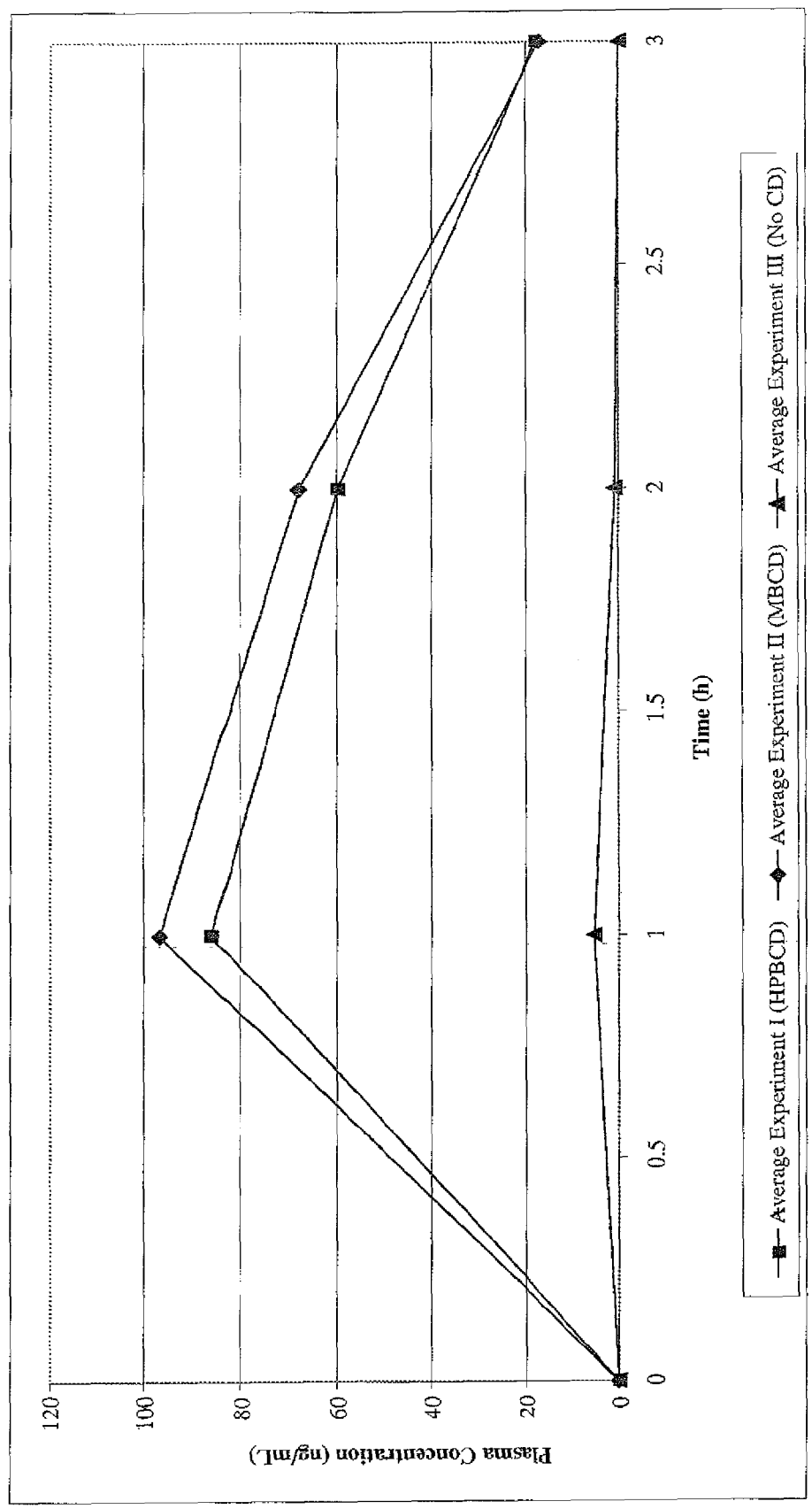
FIG. 12 shows average fulvestrant plasma concentration data plot generated for Experiments I, II, and III (oral gavage of HPBCD, MBCD or without CD).

From the data generated during this study, it is clear that very little to no oral absorption was observed for the control 5 mg/mL fulvestrant in ddH$_2$O suspension, which is in agreement with published literature, indicating that oral administration of fulvestrant presents with very poor bioavailability, thus rendering the compound unsuitable for oral formulation. In contrast to the control fulvestrant suspension formulation, both of the cyclodextrin based fulvestrant formulations (HPBCD and MBCD) presented with oral absorption. The HPBCD andvMBCD based formulations presented with similar absorption plots, as can be seen in FIG. 12, whereby the mean $C_{max}$ values for the HPBCD and MBCD were measured at 86.1 ng/mL and 96.6 ng/mL respectively and $T_{max}$ occurring for both formulations at the 1 hour sampling point. The data from rat 3 in the HPBCD group was not included in the pooled data, as its $C_{max}$ of 608.0 ng/mL is regarded as being an outlier Comparison of the data generated following the administration by oral gavage for the two novel cyclodextrin based fulvestrant formulations and the reference fulvestrant suspension formulation, revealed that very limited to no oral absorption was observed for the control 5 mg/mL fulvestrant in WFI suspension, whereby low fulvestrant concentrations were observed in two samples of rat 4 only. This observation is in agreement with published literature, indicating that oral administration of fulvestrant presents with very poor bioavailability, thus rendering the compound unsuitable for oral formulation. In contrast to the control fulvestrant suspension formulation, both of the cyclodextrin based fulvestrant formulations (HPBCD and MBCD) presented with fulvestrant being recovered from all post-dose samples collected from these two groups of animals, thus indicating that the two cyclodextrin based formulations do enhance oral bioavailability of fulvestrant significantly.

The HPBCD and MBCD based formulations presented with similar fulvestrant plasma concentrations over time, as may be evidenced by the data presented in FIG. 12, whereby the mean $C_{max}$ values for the HPBCD and MBCD formulations were measured at 86.1 ng/mL and 96.6 ng/mL respectively and $T_{max}$ occurring for both formulations at the 1 hour sampling point.

The data generated during the present study indicates that aqueous formulations of fulvestrant complexed with HPBCD or MBCD offer viable opportunities as oral formulations. Oral formulations present with distinct advantages over the currently marketed long acting IM fulvestrant formulations, which present with pain upon injection, owing to the 5 mL injection volume. In addition to the formulation related side effects, long acting IM fulvestrant (250 mg/5 mL), takes 3-6 months to achieve steady state. A viable oral formulation can achieve the desired plasma levels immediately, thus replacing the need for an IM formulation, or can be used together with the IM formulation as part of a loading-dose regimen.

Example 3

Oral Fulvestrant Absorption Study Using Fulvestrant and Hydroxypropyl Beta-Cyclodextrin (HPBCD) in Whistar Rats Fulvestrant was administered at a dose of 5 mg/kg by oral gavage to each animal, with blood concentrations measured hourly over a 4-hour period. The vehicle used to prepare the novel batch comprised 450 mg/mL hydroxypropyl beta-cyclodextrin (HPBCD) (Batch 7_4). All animals were fasted for approximately 24 hours prior to dose administration. Water was available ad libitum. Pre-dose, and 1, 2 and 3 hour post dose blood sampling for the oral gavage group was conducted by means of the tail snip procedure, whereby 0.5 mL was collected at each sampling point. Five minutes prior to the final (4-hour) blood sampling point, rats were anaesthetized with 0.5 ml 6% sodium pentobarbitone and 5 mL blood was collected. Prior to drug administration by means of gavage, each of the rats were anaesthetized with halothane gas, following which a gavage tube was inserted through the mouth and through which the various solutions were administered. 0.5 mL saline was administered through the gavage tubes immediately following drug administration. The information for this example is summarized in Table 25.

TABLE 25

Experiment information (HPBCD Oral)

| Formulation | Rat No. | Sex | Dose | Dose volume | Rat Mass |
|---|---|---|---|---|---|
| Fulvestrant Batch7_4 | 1 | Male | 5 mg/kg | 0.305 mL | 0.305 kg |
| Fulvestrant Batch7_4 | 2 | Male | 5 mg/kg | 0.325 mL | 0.325 kg |
| Fulvestrant Batch7_4 | 3 | Male | 5 mg/kg | 0.350 mL | 0.350 kg |
| Fulvestrant Batch7_4 | 4 | Male | 5 mg/kg | 0.335 mL | 0.335 kg |
| Fulvestrant Batch7_4 | 5 | Male | 5 mg/kg | 0.310 mL | 0.310 kg |
| Fulvestrant Batch7_4 | 6 | Male | 5 mg/kg | 0.274 mL | 0.274 kg |

Blood Sampling and Bioanalytical Methods

Figure 13:
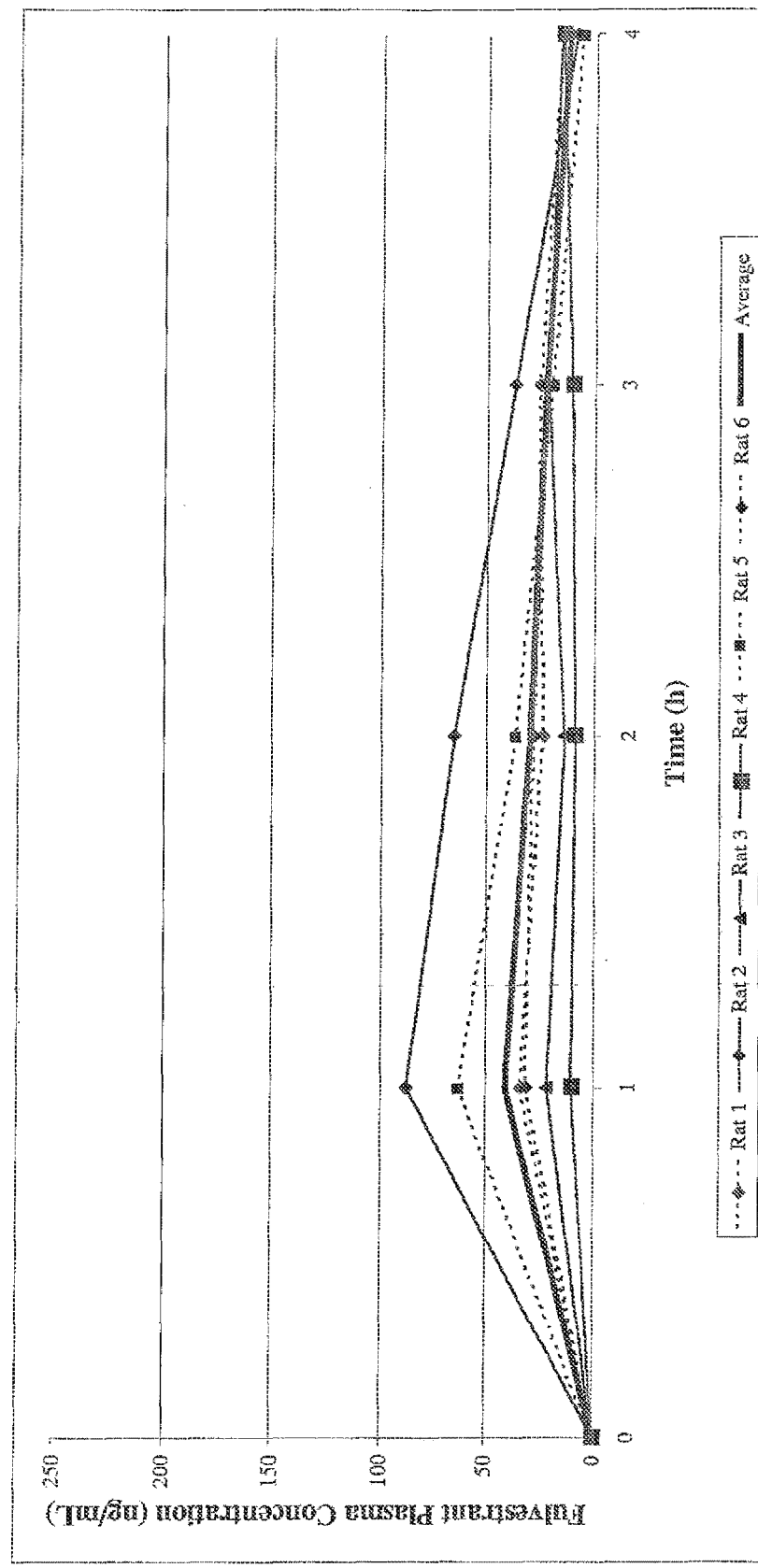
FIG. 13 shows fulvestrant plasma concentration data plot generated for oral gavage of fulvestrant-HPBCD at the dose of 5 mg/kg.

The tail snip blood was collected in 1 mL K3E (K$_3$EDTA) MINICOLLECT® (Greiner Bio-one; Lot 090319; Exp. 2010-08) blood collection tubes, with the terminal samples having been collected in 4 mL K3E (K$_3$EDTA) VACUETTE® (Greiner Bio-one; Lot L020902; Exp. 2010-08) blood collection tubes. Following collection, these samples were placed on ice and then centrifuged at 4° C. for 15 minutes. 0.2 mL and 2 mL plasma aliquots were obtained from the tail-snip and terminal sampling points respectively. These samples were frozen (−60° C. to −80° C.) prior to being shipped on dry ice to a facility for analysis of fulvestrant concentrations. The test article, fulvestrant, was measured in adult Whistar rat plasma by via an LC-MS method. Individual and mean plasma fulvestrant concentration-time profiles following oral administration by gavage in this example are presented in FIG. 13 and Table 26.

TABLE 26

Fulvestrant plasma concentration (ng/mL) data
generated for oral fulvestrant-HPBCD (5 mg/kg)

| Time (h) | 0 | 1 | 2 | 3 | 4 |
|---|---|---|---|---|---|
| Rat 1 | 0.0 | 33.6 | 24.3 | 25.6 | 15.4 |
| Rat 2 | 0.0 | 87.5 | 65.0 | 37.0 | 9.2 |
| Rat 3 | 0.0 | 22.1 | 14.3 | 22.0 | 16.1 |
| Rat 4 | 0.0 | 10.9 | 9.4 | 11.1 | 15.7 |
| Rat 5 | 0.0 | 62.4 | 36.7 | 19.7 | 5.6 |
| Rat 6 | 0.0 | 31.3 | 28.2 | 22.9 | 12.2 |
| Average | 0.0 | 41.3 | 29.7 | 23.1 | 12.4 |

Example 4

Oral Fulvestrant Dose-Ranging Absorption Study in Male and Female Beagle

The purpose of the study was to investigate the pharmacokinetics of a novel fulvestrant-hydroxypropyl-beta-cyclodextrin (fulvestrant-HPBCD) solution following oral administration at various dose levels, to that of a short acting (SA) fulvestrant intramuscular formulation in fasted male and female beagle dogs (n=6).

Materials and Methods

The study was conducted using three male and three female adult beagle dogs for a total sample size of n=6. Each dog participated in each of the five experiments. Experiments began with the lowest oral dose and progressed to the highest oral dose, with the study concluding with the Short Acting (SA) IM formulation. Animals were fasted for 12 hours prior to each study with access to ad libitum water. A minimum washout-period of 48-hours was allowed between experiments. Oral drug administration comprised the use of oro-gastric tubes for the administration of the fulvestrant-HPBCD solution (5 mg/mL fulvestrant), with the IM administration into the buttock. The following dosages of fulvestrant were administered for the various experiments:

1. Experiment 1: 2.5 mg/kg fulvestrant (5 mg/mL fulvestrant; 450 mg/mL HPBCD)
2. Experiment 2: 5 mg/kg fulvestrant (5 mg/mL fulvestrant; 450 mg/mL HPBCD)
3. Experiment 3: 10 mg/kg fulvestrant (5 mg/mL fulvestrant; 450 mg/mL HPBCD)
4. Experiment 4: 15 mg/kg fulvestrant (5 mg/mL fulvestrant; 450 mg/mL HPBCD)
5. Experiment 5: 2.5 mg/kg fulvestrant (Short Acting (SA) IM fulvestrant injection)

The oral fulvestrant solutions contained 5 mg/mL of fulvestrant in 450 mg/mL HPBCD. The fulvestrant SA IM control fulvestrant formulation was a short acting formulation, developed, described and used by AstraZeneca (20 mg/mL fulvestrant).

Venous blood samples (1 ml) were obtained from each animal at pre-dose and the following times post-dose (in minutes): 15, 30, 45, 60, 75, 90, 105, 120, 135, 150, 165, 180, 210, 240, 300, 360, 480, 720, 1080 and 1440. Samples were collected via implanted vascular ports in the jugular veins of the dogs and into tubes containing $K_2EDTA$ anticoagulant. Following collection, the blood samples were placed on ice and then centrifuged for 15 minutes. The plasma was harvested and approximately 0.5 mL aliquots were stored frozen (−18° C.) prior to being shipped on dry ice to a contract laboratory for the determination of fulvestrant in the plasma samples. The same liquid chromatography-mass spectroscopy (LC-MS) analytical method was employed as that described in Example 3.

Results

Figure 14:
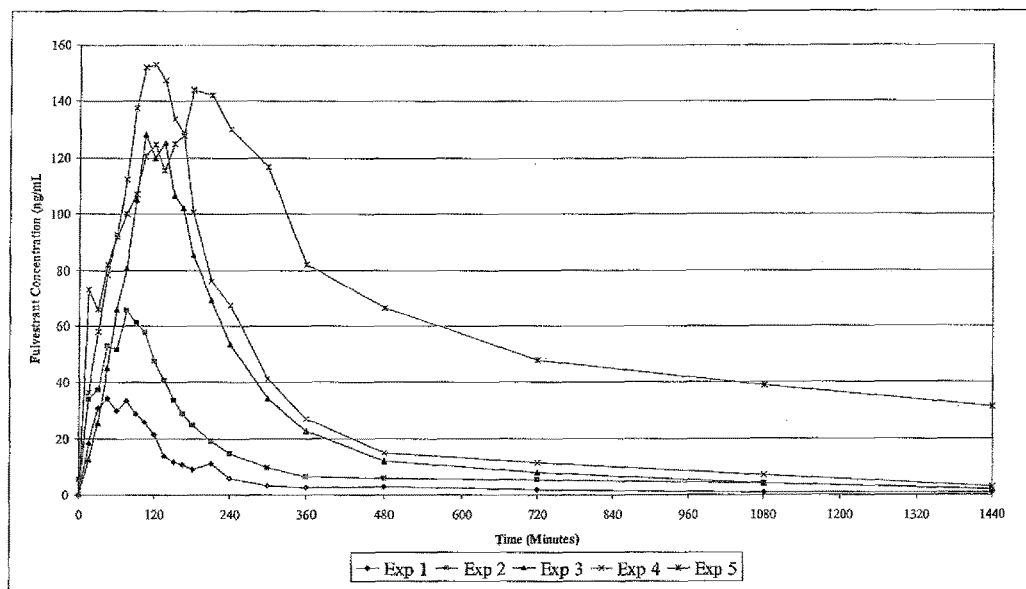
FIG. 14 shows a plot of the mean fulvestrant plasma concentrations over time.

Results generated during this study demonstrated that absorption, following oral ingestion, was rapid and followed a first order process, with fulvestrant present in all of the first post-dose blood samples (T=15 min). A plot of the mean fulvestrant plasma concentrations over time is presented in FIG. 14 (Exp 1=2.5 mg/kg oral; Exp 2=5 mg/kg oral; Exp 3=10 mg/kg oral; Exp 4=15 mg/kg oral and Exp 5=2.5 mg/kg IM).

The consistency of the pharmacokinetic parameters, following oral administration, over a six-fold dose range, suggests that the pharmacokinetics of fulvestrant-HPBCD is linear. These parameters include $T_{max}$; absorption and elimination halftimes; clearance and mean residence times. As the pharmacokinetics derived from oral administration did not differ statistically between the various doses, a more accurate estimation of the pharmacokinetics of the new fulvestrant formulation administered orally to dogs can be obtained by averaging and comparing the pharmacokinetic parameters of each individual subject. Mean values for these parameters are: Absorption halftime—19 min; Estimated bioavailability—6.5% (relative to and assuming 100% bioavailability for the LA IM fulvestrant formulation); $T_{max}$—74 min; MRT—258 min; elimination halftime—55 min.

Absorption from the gastro-intestinal tract occurs more rapidly than from the site of IM injection, as evidenced by the prolonged mean absorption halftime of the latter (77 min) and longer $T_{max}$ (223 min). Mean elimination halftimes calculated from IM dosing were considerably longer (467 min), as was the mean MRT (801 min), than those obtained following oral administration. Bioavailability for the IM administration was assumed to be complete. The $C_{max}$ attained following the IM administration at a dose of 2.5 mg/kg, was as great as those values that were achieved by the 10 mg/kg and 15 mg/kg oral doses. IM administration resulted in a mean $AUC_{0-t}$ that was significantly greater those values that resulted from all oral doses.

Figure 15:
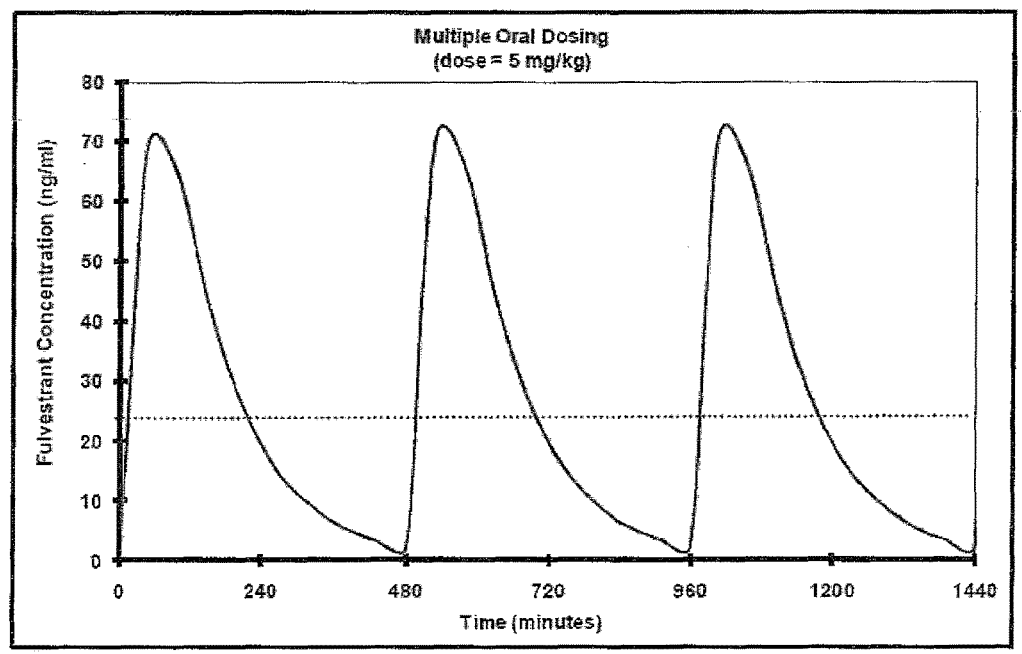
FIG. 15 shows a simulation of blood concentrations resulting from oral dosing of fulvestrant-HPBCD 5 mg/kg 8-hourly to an "average dog" (Average concentration at steady state based on exponentials=26 ng/mL. A dotted line is drawn at the level of the purported therapeutic target concentration).
Figure 16:
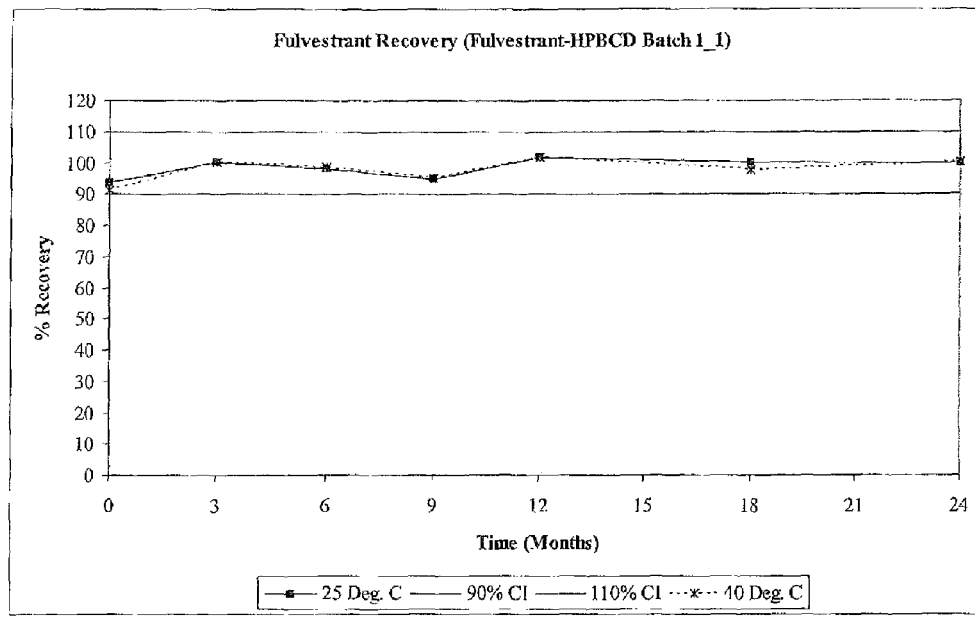
FIG. 16 shows a plot of Fulvestrant-HPBCD stability data (Batch 1_1 stored at 25° C. and 40° C.; T=0 to T=24 months).
Figure 17:
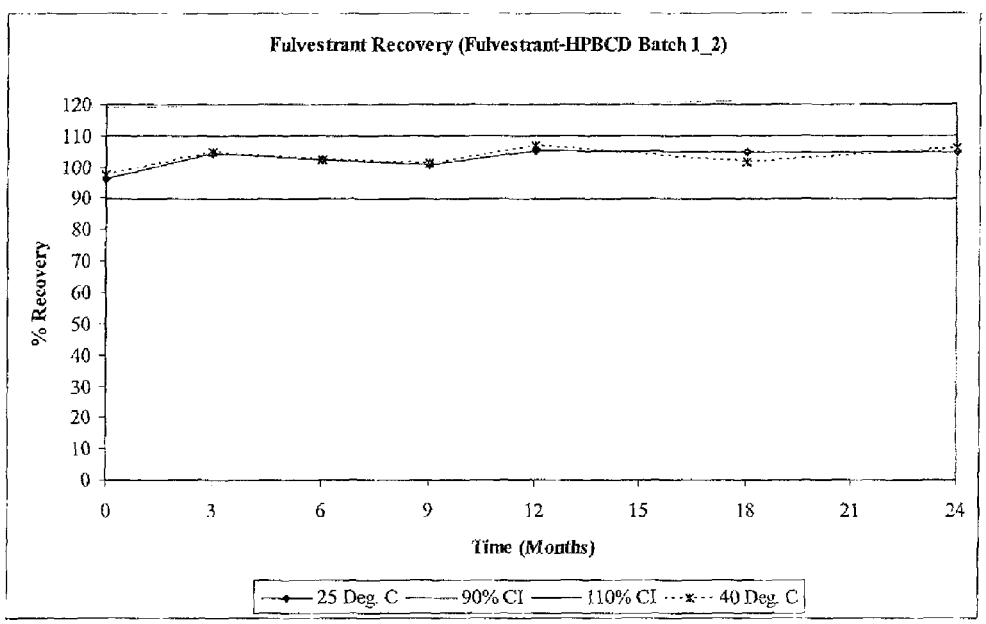
FIG. 17 shows a plot of Fulvestrant-HPBCD stability data (Batch 1_2 stored at 25° C. and 40° C.; T=0 to T=24 months).
Figure 18:
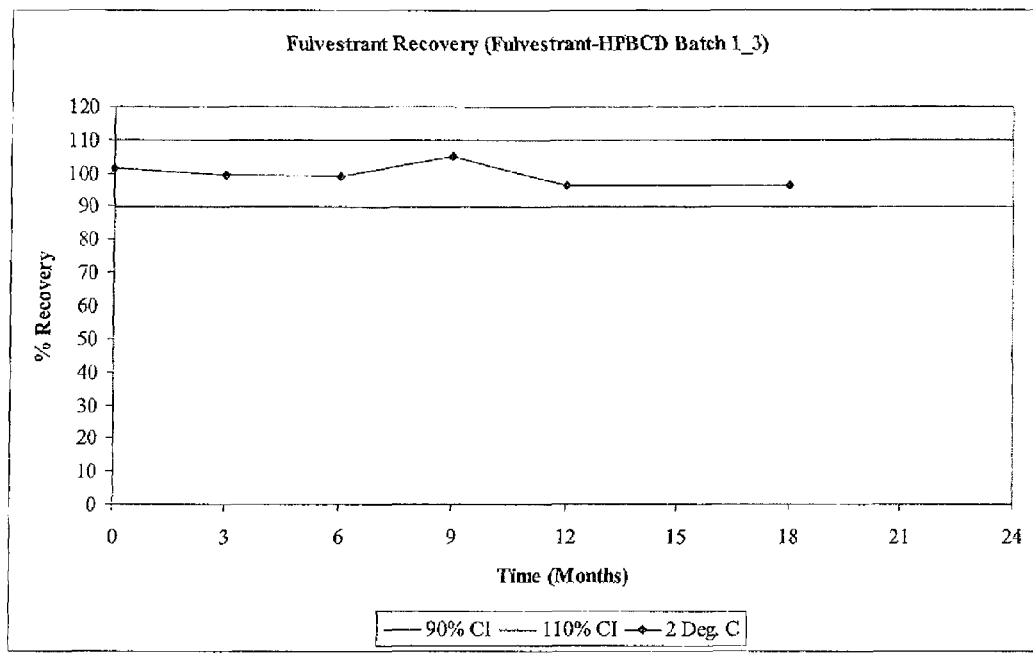
FIG. 18 shows a plot of Fulvestrant-HPBCD stability data (Batch 1_3 stored at 2° C.; T=0 to T=18 months).
Figure 19:
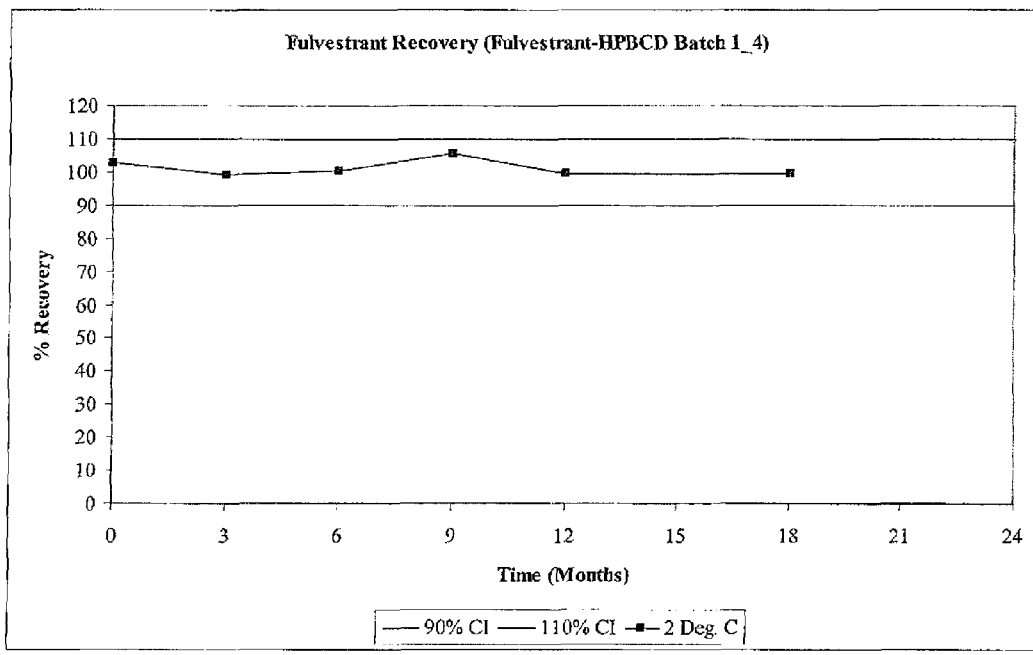
FIG. 19 shows a plot of Fulvestrant-HPBCD stability data (Batch 1_4 stored at 2° C.; T=0 to T=18 months).
Figure 20:
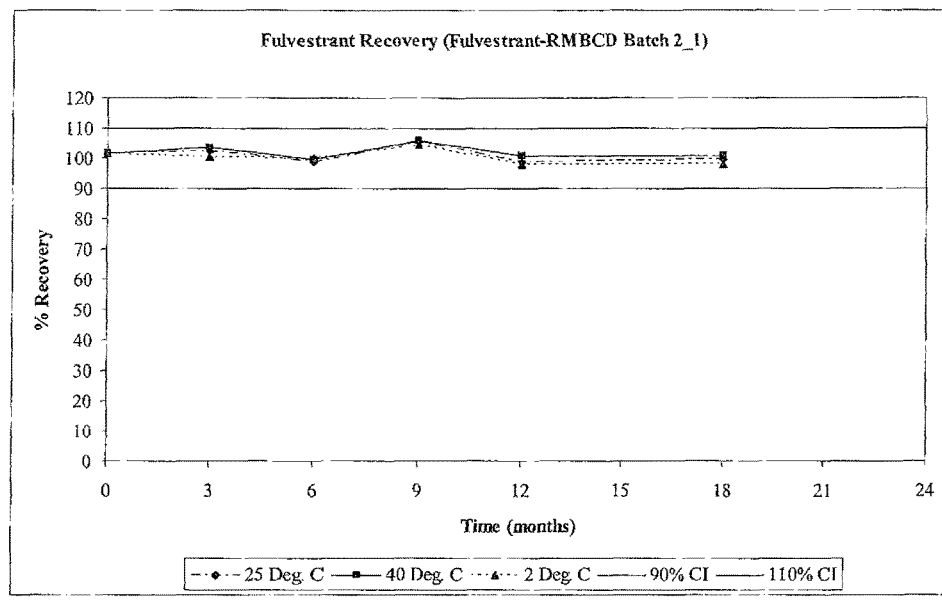
FIG. 20 shows a plot of Fulvestrant-RAMEB stability data (Batch 2_1 stored at 2° C.; 25° C. and 40° C.; T=0 to T=18 months).
Figure 21:
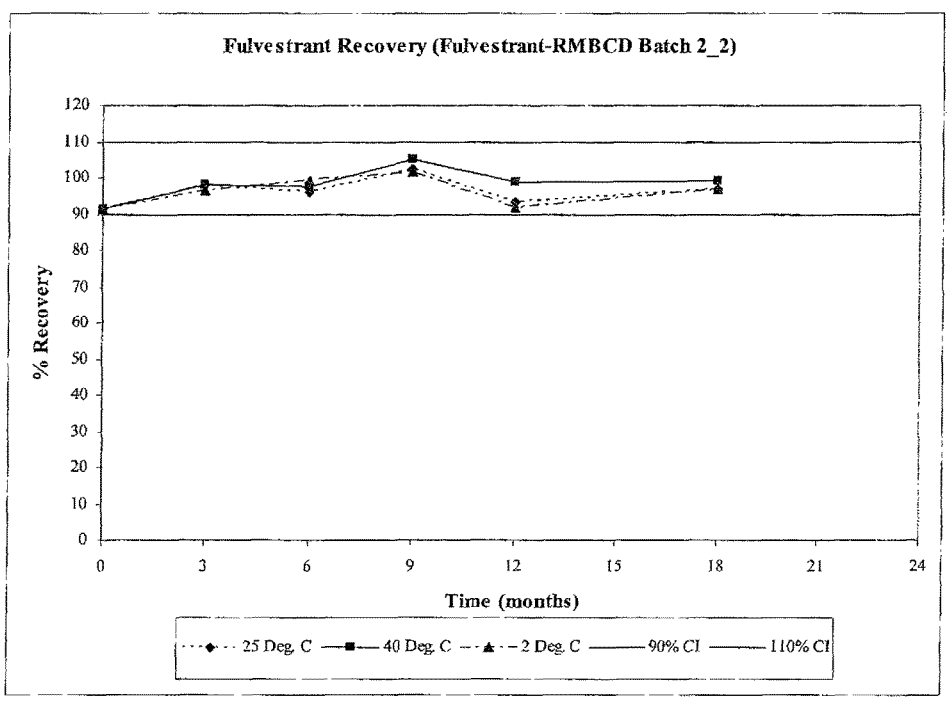
FIG. 21 shows a plot of Fulvestrant-RAMEB stability data (Batch 2__2 stored at 2° C.; 25° C. and 40° C.; T=0 to T=18 months).

Whilst the oral administration of fulvestrant-HPBCD presented with low oral bioavailability (approximately 6.5%), clinically effective concentrations of fulvestrant are systemically absorbed, due to the absorption halftime (20 min) being significantly shorter than the elimination halftime (55 minutes). During the study, systemic fulvestrant concentrations in excess of purported therapeutic levels (approximately 23 ng/mL) were achieved using the lowest administered oral dose of 2.5 mg/kg. Simulations suggest that eight-hour dosing to dogs (5 mg/kg) would achieve average concentrations (26 ng/mL) that are in excess of the proposed therapeutic levels. FIG. 15 illustrates a simulation of oral dosing to an "average" beagle dog, employing a regimen of 5 mg/kg every eight hours for 24 hours. It is postulated that similar rapid absorption may be achieved in humans.

Example 5

Stability Batches and Data

In total, six stability batches of fulvestrant in the presence of cyclodextrins were produced to evaluate different fulvestrant concentrations with different cyclodextrins exposed to 2° C.; 25° C.; 40° C. over 24-months.

The batch details are summarized in Table 27 below:

TABLE 27

Fulvestrant-HPBCD stability study batch summaries.

| Batch No. | Fulvestrant Conc. (mg/mL) | CD Type | CD Conc. | Batch size (mL) | Complexation Time (h) | Complexation temperature (° C.) | Storage volume (mL) | Vials per storage condition | Storage Temperatures |
|---|---|---|---|---|---|---|---|---|---|
| 1_1 | 5.0 | HPBCD | 400 | 40 | 24 | RT | 0.8 | 25 | 25° C.; 40° C. |
| 1_2 | 2.5 | HPBCD | 350 | 40 | 24 | RT | 0.8 | 25 | 25° C.; 40° C. |
| 1_3 | 5.0 | HPBCD | 400 | 60 | 24 | RT | 1.0 | 30 | 2° C. |
| 1_4 | 2.5 | HPBCD | 350 | 60 | 24 | RT | 1.0 | 30 | 2° C. |
| 2_1 | 10 | RAMEB | 350 | 70 | 1.5 | 60° C. | 1.0 | 23 | 2° C.; 25° C.; 40° C. |
| 2_2 | 25 | RAMEB | 350 | 70 | 1.5 | 60° C. | 1.0 | 23 | 2° C.; 25° C.; 40° C. |

RT = Room temperature ~25° C.

Each of the batches were produced, whereby the pre-weighed cyclodextrin quantity was dissolved in ~80% final volume double distilled water at ambient temperature (~25° C.). Pre-weighed fulvestrant API was then added to the cyclodextrin solution with vigorous stirring. The stirring was conducted for 24-hours for batches 1_1; 1_2; 1_3 and 1_4 under ambient conditions. Complexation was optimized for batches 2_1 and 2_2, whereby complexation duration was reduced to 1.5 hours with heating to 60° C. Following complexation, all batches were made to volume with double distilled water and filtered through 0.45 μm syringe filters, prior to being filled into storage vials. Samples were assayed via HPLC for fulvestrant content following manufacture and at each evaluation point (3; 6; 9; 12; 18 and 24-months post manufacture). The HPLC method used was also specific to the detection of the presence of the principle fulvestrant degradation product, fulvestrant sulphone. The HPLC method employed is the same as that described in Example 1. At each sampling point, three vials were selected for fulvestrant quantification; evaluation for the presence of fulvestrant sulphone and pH determination.

Summary plots for the average recoveries of the various batches and storage conditions are presented in FIGS. 16-21.

HPLC analysis of all stability samples of all batches indicated that all evaluated samples are stable, with none falling outside the 90-110% fulvestrant recovery range during the 18-24-month evaluation period at 2° C.; 25° C. and 40° C. There was no visible precipitation present, nor any increase in the presence of the principle fulvestrant degradation product, fulvestrant sulphone.

The disclosures of all publications, patents, patent applications and other references referred to herein are hereby incorporated herein by reference in their entireties.

What is claimed is:

1. An inclusion complex in aerosolized form comprising a) hydroxypropyl beta-cyclodextrin; b) a compound of the formula (I):

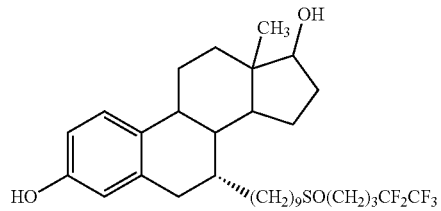

or a salt thereof or hydrate of the foregoing in a concentration between about 0.1 mg per about 25 mg hydroxypropyl beta-cyclodextrin/mL to about 5 mg per 400 mg hydroxypropyl beta-cyclodextrin/mL; and c) an aqueous or non-aqueous, isotonic sterile solution.

2. A unit dosage form comprising the inclusion complex of claim 1.

3. The inclusion complex of claim 1, in combination with one or more anti-cancer agents other than uncomplexed fulvestrant.

4. The inclusion complex of claim 1, wherein the one or more anti-cancer agents other than uncomplexed fulvestrant is configured for simultaneous or sequential administration via a similar route or a different route as that of the inclusion complex.

5. A method of treating breast cancer in an individual in need thereof, comprising administering to the individual an effective amount of the inclusion complex of claim 1.

6. The method of claim 5, wherein the method further comprises administering one other anti-cancer agent.

7. The method of claim 5, wherein the breast cancer is hormone receptor positive metastatic breast cancer in a postmenopausal woman following hormone therapy.

8. The method of claim 6, wherein the one other anti-cancer agent is administered simultaneous or sequential via a similar route or a different route as that of the inclusion complex.

* * * * *

UNITED STATES PATENT AND TRADEMARK OFFICE
CERTIFICATE OF CORRECTION

PATENT NO. : 9,724,355 B2  
APPLICATION NO. : 13/823078  
DATED : August 8, 2017  
INVENTOR(S) : Henk Swart Page 1 of 1

It is certified that error appears in the above-identified patent and that said Letters Patent is hereby corrected as shown below:

On the Title Page

Item (57) Abstract, please change Line 4 to:
lupus erythematosus. Also provided are methods of produc- Signed and Sealed this
Nineteenth Day of September, 2017

Joseph Matal
*Performing the Functions and Duties of the*
*Under Secretary of Commerce for Intellectual Property and*
*Director of the United States Patent and Trademark Office*